US012774347B2

(12) United States Patent
Tamada et al.

(10) Patent No.: US 12,774,347 B2
(45) Date of Patent: Oct. 27, 2026

(54) ISOLATED IMMUNE CELL EXPRESSING A RECEPTOR, INTERLEUKIN-7, AND CHEMOKINE (C-C MOTIF) LIGAND 19

(71) Applicant: NOILE-IMMUNE BIOTECH, INC., Tokyo (JP)

(72) Inventors: Koji Tamada, Ube (JP); Yukimi Sakoda, Ube (JP); Hidenobu Ishizaki, Tokyo (JP)

(73) Assignee: NOILE-IMMUNE BIOTECH, INC., Tokyo (JP)

( * ) Notice: Subject to any disclaimer, the term of this patent is extended or adjusted under 35 U.S.C. 154(b) by 0 days.

(21) Appl. No.: 19/193,454

(22) Filed: Apr. 29, 2025

(65) Prior Publication Data

US 2025/0268942 A1 Aug. 28, 2025

Related U.S. Application Data

(63) Continuation of application No. 18/737,778, filed on Jun. 7, 2024, now abandoned, which is a continuation-in-part of application No. 16/497,291, filed as application No. PCT/JP2018/012194 on Mar. 26, 2018, now abandoned.

(30) Foreign Application Priority Data

Mar. 27, 2017 (JP) ................................ 2017-061461

(51) Int. Cl.

| | |
|---|---|
| ***A61P 35/00*** | (2006.01) |
| ***A61K 40/11*** | (2025.01) |
| ***A61K 40/31*** | (2025.01) |
| ***A61K 40/42*** | (2025.01) |
| ***C07K 14/52*** | (2006.01) |
| ***C07K 14/54*** | (2006.01) |
| ***C07K 16/30*** | (2006.01) |
| ***C12N 5/0783*** | (2010.01) |

(52) U.S. Cl.

CPC .......... *C07K 16/3084* (2013.01); *A61K 40/11* (2025.01); *A61K 40/31* (2025.01); *A61K 40/4236* (2025.01); *A61K 40/4258* (2025.01); *A61P 35/00* (2018.01); *C07K 14/52* (2013.01); *C07K 14/5418* (2013.01); *C12N 5/0636* (2013.01); *A61K 2239/31* (2023.05); *A61K 2239/38* (2023.05); *C07K 2317/622* (2013.01); *C07K 2319/03* (2013.01); *C12N 2510/00* (2013.01)

(58) Field of Classification Search

CPC ........................... C07K 16/3084; C07K 14/52; C07K 14/5418; C07K 2319/03; C07K 14/521; C07K 14/705; A61K 40/11; A61K 40/31; A61K 40/4236; A61K 40/4258; A61K 35/17; C12N 5/0636; C12N 2510/00; C12N 2501/2307; C12N 2502/30; C12N 15/63

See application file for complete search history.

(56) References Cited

U.S. PATENT DOCUMENTS

| | | | | |
|---|---|---|---|---|
| 11,337,997 B2 * | 5/2022 | Tamada | C12N 5/0636 | |
| 11,931,381 B2 * | 3/2024 | Tamada | C07K 14/7051 | |
| 2009/0028877 A1 * | 1/2009 | Iida | A61P 31/00 | 435/69.6 |
| 2011/0236374 A1 * | 9/2011 | Shitara | A61P 35/00 | 536/23.53 |
| 2014/0220003 A1 * | 8/2014 | Yano | A61K 39/3955 | 424/133.1 |

FOREIGN PATENT DOCUMENTS

WO 2017/189959 A1 11/2017

OTHER PUBLICATIONS

Office Action issued in corresponding European Patent Application No. 24209637.8, dated May 4, 2026.

* cited by examiner

*Primary Examiner* — Brian Whiteman
*Assistant Examiner* — Khaleda B Hasan
(74) *Attorney, Agent, or Firm* — Morgan, Lewis & Bockius LLP

(57) ABSTRACT

The present disclosure provides an isolated immune cell which expresses a receptor, interleukin-7, and chemokine (C—C motif) ligand 19.

19 Claims, 15 Drawing Sheets

Specification includes a Sequence Listing.

ISOLATED IMMUNE CELL EXPRESSING A RECEPTOR, INTERLEUKIN-7, AND CHEMOKINE (C-C MOTIF) LIGAND 19

TECHNICAL FIELD

Priority is claimed on Japanese Patent Application No. 2017-061461, filed Mar. 27, 2017, the content of which is incorporated herein by reference.

SEQUENCE LISTING SUBMISSION VIA PATENT CENTER

A computer readable text file, entitled "132281-5002-US-02_SequenceListing.xml", created on Jun. 7, 2024, with a file size of 115,352 bytes contains the sequence listing for this application and is hereby incorporated by reference in its entirety.

BACKGROUND ART

A chimeric antigen receptor (hereinafter, also referred to as "CAR") is an artificial chimeric protein in which a single-stranded antibody that recognizes a cell surface antigen of a cancer cell is fused with a signal transduction region that induces T cell activation. For example, by introducing a gene encoding a CAR into normal peripheral blood T cells having no tumor reactivity (peripheral blood T lymphocytes), it is possible to produce a large amount of CAR-expressing T cells (hereinafter also referred to as "CAR-T cells") capable of expressing a CAR. Such CAR-T cells have tumor reactivity, and thus can allow cancer cells to be impaired without relying on interaction with the major histocompatibility complex (MHC).

Regarding cancer immunotherapy by administration of CAR-T cells, more specifically, a therapy in which T cells are collected from a patient, a gene encoding a CAR is introduced into such T cells, and the gene is amplified to be retransferred into the patient, clinical trials are currently in progress all over the world, and results showing efficacy in hematopoietic malignancies such as leukemia and lymphoma, and the like have been obtained.

However, in cancer immunotherapy using CAR-T cells, the current situation is that effective results are obtained only for hematopoietic malignancies, and effective results are not obtained for solid tumors. In order to develop an effective CAR for solid tumors, selection of target antigens is important, and searches for target antigens applicable to solid tumors are required.

Meanwhile, as factors in a case where CAR-T cell therapy is not effective against solid tumors, a low survival ratio of CAR-T cells in vivo, a low level of accumulation thereof in local tumors, activity inhibition thereof by immunosuppressive factors secreted by tumor cells and the like, and the like are conceivable. As a method for solving such a problem, a method has been reported in which a nucleic acid encoding an immune function-promoting factor of T cells is introduced into T cells together with a nucleic acid encoding a CAR (Patent Literature 1).

CITATION LIST

Patent Literature

[Patent Literature 1]
PCT International Publication No. WO2016/056228

SUMMARY OF INVENTION

Technical Problem

Since effects of CAR-T cells targeting an antigen expressed in a human solid tumor have not been confirmed in Patent Literature 1, CAR-T cells showing efficacy against such an antigen are required.

An objective of the present invention is to provide a novel CAR that targets a solid tumor antigen as a target antigen, and a CAR-T cell that is effective against solid tumors.

Solution to Problem

The present disclosure includes the following aspects.

(1) A chimeric antigen receptor including a target antigen-binding region; a transmembrane region; and a T cell activation signal transduction region, in which the target antigen is ganglioside GM2.

(2) The chimeric antigen receptor according to (1), in which the target antigen-binding region includes a heavy-chain variable region and a light-chain variable region of an anti-ganglioside GM2 antibody.

(3) The chimeric antigen receptor according to (2), in which the anti-ganglioside GM2 antibody is an antibody selected from the group consisting of the following (a) to (c):

(a) an antibody that includes a heavy-chain variable region including CDR1, CDR2, and CDR3 of a heavy-chain variable region consisting of an amino acid sequence set forth in SEQ ID NO: 2, and a light-chain variable region including CDR1, CDR2, and CDR3 of a light-chain variable region consisting of an amino acid sequence set forth in SEQ ID NO: 4, and that has a binding ability to ganglioside GM2;

(b) an antibody that includes a heavy-chain variable region consisting of an amino acid sequence in which one or several amino acids are mutated in the amino acid sequence set forth in SEQ ID NO: 2, and a light-chain variable region consisting of an amino acid sequence in which one or several amino acids are mutated in the amino acid sequence set forth in SEQ ID NO: 4, and that has a binding ability to ganglioside GM2; and (c) an antibody that includes a heavy-chain variable region consisting of an amino acid sequence having 70% or more sequence identity to the amino acid sequence set forth in SEQ ID NO: 2, and a light-chain variable region consisting of an amino acid sequence having 70% or more sequence identity to the amino acid sequence set forth in SEQ ID NO: 4, and that has a binding ability to ganglioside GM2.

(4) The chimeric antigen receptor according to (3), in which the heavy-chain variable region includes the amino acid sequence set forth in SEQ ID NO: 2, and the light-chain variable region includes the amino acid sequence set forth in SEQ ID NO: 4.

(5) The chimeric antigen receptor according to any one of (2) to (4), in which the anti-ganglioside GM2 antibody is a single-stranded antibody (scFv).

(6) The chimeric antigen receptor according to (5), in which the scFv is a polypeptide selected from the group consisting of the following (a) to (c):

(a) a polypeptide that includes an amino acid sequence selected from the group consisting of SEQ ID NOs: 10, 12, 14, and 16;

(b) a polypeptide that consists of an amino acid sequence having 70% or more sequence identity to an amino acid sequence selected from the group consisting of SEQ ID NOs: 10, 12, 14, and 16, and that has a binding ability to ganglioside GM2; and (c) a polypeptide that consists of an amino acid sequence in which one or several amino acids are mutated in an amino acid sequence selected from the group consisting of SEQ ID NOs: 10, 12, 14, and 16, and that has a binding ability to ganglioside GM2.

(7) The chimeric antigen receptor according to any one of (1) to (6), in which the transmembrane region is a transmembrane region of CD8.

(8) The chimeric antigen receptor according to (7), in which the transmembrane region of CD8 includes a polypeptide selected from the group consisting of the following (a) to (c):

(a) a polypeptide that includes an amino acid sequence set forth in SEQ ID NO: 20;

(b) a polypeptide that consists of an amino acid sequence having 70% or more sequence identity to the amino acid sequence set forth in SEQ ID NO: 20, and that has a transmembrane ability; and (c) a polypeptide that consists of an amino acid sequence in which one or several amino acids are mutated in the amino acid sequence set forth in SEQ ID NO: 20, and that has a transmembrane ability.

(9) The chimeric antigen receptor according to any one of (1) to (8), in which the T cell activation signal transduction region is a T cell activation signal transduction region of CD3ζ.

(10) The chimeric antigen receptor according to (9), in which the T cell activation signal transduction region of CD3ζ includes a polypeptide selected from the group consisting of the following (a) to (c):

(a) a polypeptide that includes an amino acid sequence set forth in SEQ ID NO: 28;

(b) a polypeptide that consists of an amino acid sequence having 70% or more sequence identity (homology) to the amino acid sequence set forth in SEQ ID NO: 28, and that has a T cell activation signal transduction ability; and (c) a polypeptide that consists of an amino acid sequence in which one or several amino acids are mutated in the amino acid sequence set forth in SEQ ID NO: 28, and that has a T cell activation signal transduction region ability.

(11) The chimeric antigen receptor according to (9) or (10), in which the T cell activation signal transduction region further includes at least one of a T cell activation signal transduction region of CD28 and a T cell activation signal transduction region of 4-1BB.

(12) The chimeric antigen receptor according to (11), in which the T cell activation signal transduction region of CD28 includes a polypeptide selected from the group consisting of the following (a) to (c):

(a) a polypeptide that includes an amino acid sequence set forth in SEQ ID NO: 24;

(b) a polypeptide that consists of an amino acid sequence having 70% or more sequence identity (homology) to the amino acid sequence set forth in SEQ ID NO: 24, and that has a T cell activation signal transduction ability; and (c) a polypeptide that consists of an amino acid sequence in which one or several amino acids are mutated in the amino acid sequence set forth in SEQ ID NO: 24, and that has a T cell activation signal transduction region ability.

(13) The chimeric antigen receptor according to (11), in which the T cell activation signal transduction region of 4-1BB includes a polypeptide selected from the group consisting of the following (a) to (c):

(a) a polypeptide that includes an amino acid sequence set forth in SEQ ID NO: 26;

(b) a polypeptide that consists of an amino acid sequence having 70% or more sequence identity (homology) to the amino acid sequence set forth in SEQ ID NO: 26, and that has a T cell activation signal transduction ability; and (c) a polypeptide that consists of an amino acid sequence in which one or several amino acids are mutated in the amino acid sequence set forth in SEQ ID NO: 26, and that has a T cell activation signal transduction region ability.

(14) The chimeric antigen receptor according to any one of (11) to (13), in which the T cell activation signal transduction region includes the T cell activation signal transduction regions of CD28, 4-1BB, and CD3ζ and is located in the order of CD28, 4-1BB, and CD3ζ from an N-terminal side.

(15) A cell which expresses the chimeric antigen receptor according to any one of (1) to (14).

(16) The cell according to (15), which further expresses at least one of IL-7 or CCL19.

(17) The cell according to (16), which expresses both IL-7 and CCL19.

(18) The cell according to (16) or (17), in which the IL-7 includes a polypeptide selected from the group consisting of the following (a) to (c):

(a) a polypeptide that includes an amino acid sequence set forth in SEQ ID NO: 59;

(b) a polypeptide that consists of an amino acid sequence having 70% or more sequence identity to the amino acid sequence set forth in SEQ ID NO: 59, and that has a T cell-immune-function-promoting function; and (c) a polypeptide that consists of an amino acid sequence in which one or several amino acids are mutated in the amino acid sequence set forth in SEQ ID NO: 59, and that has a T cell-immune-function-promoting function.

(19) The cell according to any one of (16) to (18), in which the CCL19 includes a polypeptide selected from the group consisting of the following (a) to (c):

(a) a polypeptide that includes an amino acid sequence set forth in SEQ ID NO: 61;

(b) a polypeptide that consists of an amino acid sequence having 70% or more sequence identity to the amino acid sequence set forth in SEQ ID NO: 61, and that has a T cell-immune-function-promoting function; and (c) a polypeptide that consists of an amino acid sequence in which one or several amino acids are mutated in the amino acid sequence set forth in SEQ ID NO: 61, and that has a T cell-immune-function-promoting function.

(20) The cell according to any one of (15) to (19), in which the cell is an immune cell.

(21) The cell according to (20), in which the immune cell is a T cell.

(22) A polynucleotide including a base sequence that encodes the chimeric antigen receptor according to any one of (1) to (14).

(23) The polynucleotide according to (22), further including at least one of a base sequence that encodes IL-7 or a base sequence that encodes CCL19.

(24) The polynucleotide according to (23), including both the base sequence that encodes IL-7 and a base sequence that encodes CCL19.

(25) A vector including a base sequence that encodes the chimeric antigen receptor according to any one of (1) to (14).

(26) The vector according to (25), further including at least one of a base sequence that encodes IL-7 or a base sequence that encodes CCL19.

(27) The vector according to (26), including both the base sequence that encodes IL-7 and a base sequence that encodes CCL19.

(28) A method for producing a cell expressing a chimeric antigen receptor, including introducing a polynucleotide or a vector that includes a base sequence encoding the chimeric antigen receptor according to any one of (1) to (14) into the cell.

(29) The method for producing a cell expressing a chimeric antigen receptor according to (28), further including introducing a polynucleotide or a vector that includes at least one of a base sequence encoding IL-7 or a base sequence encoding CCL19 into the cell.

(30) The method for producing a cell expressing a chimeric antigen receptor according to (29), further including introducing a polynucleotide or a vector that includes both a base sequence encoding IL-7 and a base sequence encoding CCL19 into the cell.

(31) A pharmaceutical composition comprising the cell according to any one of (15) to (20).

(32) The pharmaceutical composition according to (31), which is a pharmaceutical composition for treating or preventing a tumor.

Advantageous Effects of Invention

According to one embodiment of the present invention, a novel CAR that targets a solid tumor antigen as a target antigen, and a CAR-T cell that is effective against solid tumors are provided.

BRIEF DESCRIPTION OF DRAWINGS

FIG. 5A shows results of the assay in which malignant mesothelioma cell lines (Y-meso8A and MSTO211H) are used as target cells. In the graphs, each of "VL15VH," "VL25VH," "VH15VL," and "VH25VL" represents results with the anti-GM2 CAR-IL-7/CCL19-expressing T cells including the corresponding sequences as scFv sequences of anti-GM2 CAR (the same applies in the subsequent graphs).

FIG. 5B shows results of the assay in which myeloma cell lines (KMS-11 and KMS-28PE) are used as target cells.

FIG. 6A shows results of the assay in which a malignant mesothelioma cell line (Y-meso8A) is used as a target cell. In the graphs, "FITC CAR-T" represents anti-FITC CAR-T cells used as a negative control (the same applies in the subsequent graphs).

FIG. 6B shows results of the assay in which a myeloma cell line (KMS11) is used as a target cell.

FIG. 6C shows results of the assay in which a colon cancer cell line (SW480) is used as a target cell.

DESCRIPTION OF EMBODIMENTS

Figure 1A:
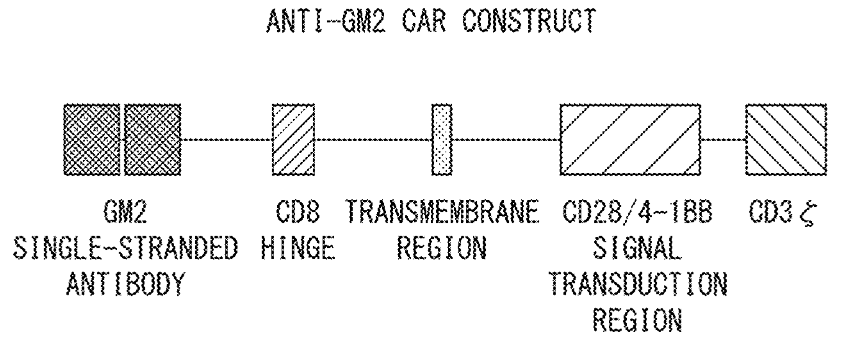
FIG. 1A is a schematic view showing an anti-GM2 CAR construct.

Polypeptides, polynucleotides, vectors, and cells provided by the present invention may be in an isolated state. In other words, polypeptides, polynucleotides, vectors, and cells described in the present specification may be isolated polypeptides, isolated polynucleotides, isolated vectors, and isolated cells.

[Chimeric Antigen Receptor (Anti-GM2 CAR)]

In one embodiment, the present invention provides a chimeric antigen receptor including a target antigen-binding region; a transmembrane region; and a T cell activation signal transduction region, in which the target antigen is ganglioside GM2.

In the present specification, the term "chimeric antigen receptor (CAR)" means a chimeric protein including a target antigen-binding region, a transmembrane region, and a T cell activation signal transduction region. The chimeric protein means a protein including a sequence derived from two or more kinds of heterologous proteins. A CAR is not limited to a CAR including only the above three regions, and includes a CAR including other regions.

<Target Antigen-Binding Region>

The CAR of the present embodiment includes a target antigen-binding region in which the target antigen is ganglioside GM2 (hereinafter also referred to as "GM2").

The term "target antigen-binding region" means an extracellular region that binds to a target antigen extracellularly when a CAR is expressed in a T cell. A CAR expressed in a CAR-T cell transfers to a cell membrane to be in a state in which a target antigen-binding region located extracellularly and a T cell activation signal transduction region located intracellularly are connected through a transmembrane region that penetrates the cell membrane. When the CAR-T cell comes into contact with a cell having the target antigen as a membrane antigen, the target antigen-binding region binds to the target antigen, whereby the T cell activation signal is transmitted from the T cell activation signal transduction region to the inside of the T cell to activate the T cell.

In the CAR of the present embodiment, the target antigen to which the target antigen-binding region binds is GM2.

GM2 is a type of ganglioside that is a glycolipid having a sialic acid. A ganglioside is a molecule that constitutes a cell membrane of an animal, and is composed of a sugar chain that is a hydrophilic side chain, and sphingosine and a fatty acid which are hydrophobic side chains. Gangliosides are classified according to the binding type and number of bonds with sialic acid, and the presence or absence of binding of N-acetylgalactosamine (GalNAc) and galactose (Gal) which bind to a non-reducing end. GM2 is one of gangliosides having a sugar chain structure of GalNAcβ1-4 (SAα2-3) Galβ1-4Glcβ1-1 Ceramide.

The type and expression level of gangliosides vary depending on the cell type, organ type, animal type, and the like. It is known that expression of gangliosides changes quantitatively and qualitatively in the process of cancerous change of cells (Cancer Res 45: 2405-14 (1985)). It has been reported that hardly any GM2 can be recognized as being expressed in normal cells, but can be expressed in tumors such as in lung cancer, neuroblastoma, glioma, melanoma, malignant mesothelioma, and myeloma (Cancer Res 45: 2405-14 (1985); Cancer Res 50: 7444-9 (1990); Cancer Sci vol. 102 no. 12: 2157-2163; Cancer Sci vol. 106 no. 1: 102-107 (2015)).

The target antigen-binding region is not particularly limited as long as it can specifically bind to GM2, but preferably includes an antigen-binding region of a monoclonal antibody (hereinafter also referred to as an "anti-GM2 antibody") capable of specifically binding to GM2. The "antigen-binding region" of an antibody refers to a region involved in binding to an antigen in an antibody, and specifically refers to a region including a complementarity determining region (CDR). The antigen-binding region of an antibody includes at least one CDR of the antibody. In a preferred embodiment, the antigen-binding region of an antibody includes all six CDRs of the antibody. CDRs can be determined by any definition known for definition of CDRs, and it is possible to use, for example, the definition by Kabat, Chothia, AbM, cotact, and the like. Preferred examples of CDRs include CDRs defined by Kabat.

An anti-GM2 antibody that can be used for the target antigen-binding region is not particularly limited, and may be a known antibody or a newly produced antibody. When newly producing an anti-GM2 antibody, production of the anti-GM2 antibody may be performed by a known method. For example, it is possible to use a method of immunizing an animal with GM2 to obtain a hybridoma, a phage display method, or the like.

An organism from which the anti-GM2 antibody is derived is not particularly limited, but a human antibody is preferable. Examples of human anti-GM2 antibodies include an antibody having an amino acid sequence set forth in SEQ ID NO: 2 as a heavy-chain variable (VH) region and an amino acid sequence set forth in SEQ ID NO: 4 as a light-chain variable (VL) region, and the like. Amino acid sequences of CDRs 1 to 3 according to the definition of Kabat of the VH region consisting of the amino acid sequence set forth in SEQ ID NO: 2 are respectively shown as SEQ ID NOs: 63 to 65. In addition, amino acid sequences of CDRs 1 to 3 according to the definition of Kabat of the VL region consisting of the amino acid sequence set forth in SEQ ID NO: 4 are respectively shown as SEQ ID NOs: 66 to 68.

In a preferred embodiment, the target antigen-binding region can include the VH region and the VL region of the anti-GM2 antibody. For example, a polypeptide including a single-stranded antibody (scFv) having the VH region and the VL region of the anti-GM2 antibody is a suitable example of the target antigen-binding region. The scFv is a polypeptide in which a VH region and a VL region of an antibody are linked via a peptide linker, and is generally used as a target antigen-binding region of a CAR.

In a case of using scFv, a peptide linker for linking the VH region and the VL region is not particularly limited, and peptide linkers generally used for scFv may be used. Examples of peptide linkers include a linker 15 (SEQ ID NO: 6), a linker 25 (SEQ ID NO: 8), and the like, but examples are not limited thereto.

The VH region and the VL region of the anti-GM2 antibody may be used as a VH region and a VL region used for scFv. Preferred examples of anti-GM2 antibodies are as described above. In addition, a part of the sequence may be modified in the VH region and the VL region used for scFv as long as a binding ability to GM2 is retained. For example, as scFv, the following examples can be preferably used.

(1a) scFv that includes a VH region including CDRs 1 to 3 of the VH region consisting of the amino acid sequence set forth in SEQ ID NO: 2 and a VL region including CDRs 1 to 3 of the VL region consisting of the amino acid sequence set forth in SEQ ID NO: 4, and that has a binding ability to GM2.

(1b) scFv that includes the VH region consisting of the amino acid sequence set forth in SEQ ID NO: 2 and the VL region consisting of the amino acid sequence set forth in SEQ ID NO: 4, and that has a binding ability to GM2.

(1c) scFv that includes a VH region consisting of an amino acid sequence in which one or several amino acids are mutated in the amino acid sequence set forth in SEQ ID NO: 2, and a VL region consisting of an amino acid sequence in which one or several amino acids are mutated in the amino acid sequence set forth in SEQ ID NO: 4, and that has a binding ability to GM2.

(1d) scFv that includes a VH region consisting of an amino acid sequence having 70% or more sequence identity (homology) to the amino acid sequence set forth in SEQ ID NO: 2, and a VL region consisting of an amino acid sequence having 70% or more sequence identity (homology) to the amino acid sequence set forth in SEQ ID NO: 4, and that has a binding ability to GM2.

In the above (1a), as sequences (framework sequences) other than CDRs, it is preferable to use framework sequences of known human antibodies. For example, it is possible to select sequences from framework sequences of amino acid sequences of human antibodies registered in known sequence databases such as GenBank, amino acid sequences selected from consensus sequences derived from each subgroup of human antibodies (Human Most Homologous Consensus Sequence; Sequences of Proteins of Immunological Interest by Kabat, E. A. et al., US Dept. Health and Human Services, 1991), and the like.

In the above (1c), the term "several" may refer to, for example, 2 to 30, preferably refers to 2 to 20, more preferably refers to 2 to 10, and still more preferably refers to 2 to 5. In addition, the term "mutated" may refer to any of deletion, substitution, addition, and insertion, or a combination thereof. Furthermore, a location of mutation is preferably a region other than CDRs 1 to 3 (that is, a framework region).

In the above (1d), the sequence identity is not particularly limited as long as it is 70% or more, but is preferably 80% or more, is more preferably 85% or more, is even more preferably 90% or more, is still more preferably 95% or more, and is particularly preferably 6% or more, 97% or more, 98% or more, or 99% or more. A sequence identity (or homology) between amino acid sequences is obtained as a proportion of matching amino acids to the entire amino acid sequence excluding gaps in the obtained alignment by juxtaposing two amino acid sequences while inputting gaps in portions corresponding to insertions and deletions so that the corresponding amino acids match most closely. The sequence identity between amino acid sequences can be obtained using various types of homology search software known in the technical field. For example, a value of sequence identity of amino acid sequences can be obtained by calculation based on an alignment obtained by the known homology search software BLASTP.

Specific examples of scFv's include, for example, a polypeptide that includes an amino acid sequence selected from the group consisting of SEQ ID NOs: 10, 12, 14, and 16; a polypeptide that consists of an amino acid sequence selected from the group consisting of SEQ ID NOs: 10, 12, 14, and 16; a polypeptide that consists of an amino acid sequence in which one or several amino acids are mutated in an amino acid sequence selected from the group consisting of SEQ ID NOs: 10, 12, 14, and 16, and that has a binding ability to GM2; a polypeptide that consists of an amino acid sequence having 70% or more sequence identity (homology) to an amino acid sequence selected from the group consisting of SEQ ID NOs: 10, 12, 14, and 16, and that has a binding ability to GM2; and the like. Regarding the term "several" and the term "mutated," the same applies as described above. In addition, regarding the term "sequence identity," the same applies as described above.

<Transmembrane Region>

The term "transmembrane region" means a region that is present by penetrating a cell membrane and is linked to an extracellular region and an intracellular region when a CAR is expressed in a T cell. The transmembrane region is not particularly limited as long as it is a polypeptide having a function of penetrating a cell membrane. The transmembrane region may be derived from a natural protein or may be artificially designed. A transmembrane region derived from a natural protein can be obtained from any membrane-binding protein or transmembrane protein. In a preferred embodiment, the transmembrane region can transmit an activation signal to the T cell activation signal transduction region in response to binding of the target antigen to the target antigen-binding region.

Examples of transmembrane regions include transmembrane regions of an α chain and a β chain of a T cell receptor, CD3ζ, CD28, CD3ε, CD45, CD4, CD5, CD8, CD9, CD16, CD22, CD33, CD37, CD64, CD80, CD86, CD134, CD137, ICOS, CD154, GITR, and the like. Preferred examples include a transmembrane region of CD8. An organism from which these proteins are derived is not particularly limited, but is preferably human. Amino acid sequences of these proteins are available from known sequence databases such as GenBank. Examples of amino acid sequences of human CD8 include an amino acid sequence registered as GenBank No: NM_001768.6, and the like, and examples of amino acid sequences of the transmembrane region include an amino acid sequence set forth in SEQ ID NO: 20.

In addition, the transmembrane region may be a mutant of the above-mentioned transmembrane region derived from a natural protein. Examples of mutants of a transmembrane region derived from a natural protein include the following.

(2a) A polypeptide that consists of an amino acid sequence having 70% or more sequence identity (homology) to an amino acid sequence (for example, SEQ ID NO: 20) of a transmembrane region derived from a natural protein, and that has a transmembrane ability.

(2b) A polypeptide that consists of an amino acid sequence in which one or several amino acids are mutated in the amino acid sequence (for example, SEQ ID NO: 20) of a transmembrane region derived from a natural protein, and has a transmembrane ability.

In the above (2a), the sequence identity is not particularly limited as long as it is 70% or more, but is preferably 80% or more, is more preferably 85% or more, is even more preferably 90% or more, and is particularly preferably 95% or more.

In the above (2b), the term "several" may refer to, for example, 2 to 10, preferably refers to 2 to 5, more preferably refers to 2 to 4, and still more preferably refers to 2 or 3. In addition, the term "mutated" may refer to any of deletion, substitution, addition, and insertion, or a combination thereof.

<T Cell Activation Signal Transduction Region>

The term "T cell activation signal transduction region" means a region that is located intracellularly and transmits a T cell activation signal to the inside of the T cell when a CAR is expressed in the T cell. In a T cell, when an MHC-peptide complex binds to a T cell receptor (TCR), a T cell activation signal is transmitted to the inside of the cell via a TCR-CD3 complex, and various phosphorylation signals are triggered (primary signal transduction). In addition, it is known that costimulatory molecules expressed on a cell surface of a T cell transmit costimulatory signals to the inside of the cell and support activation of the T cell by binding of each costimulatory molecule expressed on a cell surface of an antigen presenting cell to a specific ligand (secondary signal transduction).

In the present specification, the term "T cell activation signal transduction" includes both the primary signal transduction and the secondary signal transduction mentioned above. The term "T cell activation signal transduction region" means an intracellular region involved in signal transduction of a protein involved in the primary signal transduction and the secondary signal transduction.

The T cell activation signal transduction region is not particularly limited as long as it is a T cell activation signal transduction region of a protein involved in T cell activation signal transduction. For example, an immunoreceptor tyrosine-based activation motif (ITAM) is known to be involved in primary signal transduction. Accordingly, examples of T cell activation signal transduction regions include a T cell activation signal transduction region of a protein having an ITAM. Examples of proteins having an ITAM include CD3ζ, FcRγ, FcRβ, CD3γ, CD3δ, CD3ε, CD5, CD22, CD79a, CD79b, CD66d, and the like. A T cell activation signal transduction region including an ITAM of these proteins is a preferred example of the T cell activation signal transduction region used for a CAR. More preferred examples thereof include a T cell activation signal transduction region of CD3ζ or the like.

In addition, costimulatory molecules are involved in secondary signal transduction as described above. Accordingly, examples of T cell activation signal transduction regions also include a signal transduction region of costimulatory molecules. Examples of costimulatory molecules include CD2, CD4, CD5, CD8, CD27, CD28, OXO40 (CD134), 4-1BB (CD137), ICOS, CD154, HVEM, GITR, Fc Receptor-associated γ chain, and the like. A T cell activation signal transduction region of these proteins is also a preferred example of the T cell activation signal transduction region used for a CAR. More preferred examples thereof include a T cell activation signal transduction region of CD28, 4-1BB, or the like.

An organism from which the above-mentioned proteins are derived is not particularly limited, but is preferably human. Amino acid sequences of these proteins are available from known sequence databases such as GenBank. Examples of amino acid sequences of human CD3ζ include an amino acid sequence registered as GenBank No: NM_000734.3, and the like, and examples of amino acid sequences of the T cell activation signal transduction region include an amino acid sequence set forth in SEQ ID NO: 28. In addition, examples of amino acid sequences of human CD28 include an amino acid sequence registered as GenBank No: NM_006139.2, and the like, and examples of amino acid sequences of the T cell activation signal transduction region include an amino acid sequence set forth in SEQ ID NO: 24. Furthermore, examples of amino acid sequences of human 4-1BB include an amino acid sequence registered as GenBank No: NM_001561.5, and the like, and examples of amino acid sequences of the T cell activation signal transduction region include an amino acid sequence set forth in SEQ ID NO: 26.

Furthermore, a T cell activation signal transduction region may be a mutant of the T cell activation signal transduction region derived from a natural protein as described above. Examples of mutants of an activation signal transduction region derived from a natural protein include the following.

(3a) A polypeptide that consists of an amino acid sequence having 70% or more sequence identity (homology) to an amino acid sequence (for example, SEQ ID NOs: 24, 26, or 28) of a T cell activation signal transduction region derived from a natural protein, and that has a T cell activation signal transduction ability.

(3b) A polypeptide that consists of an amino acid sequence in which one or several amino acids are mutated in the amino acid sequence (for example, SEQ ID NOs: 24, 26, or 28) of a T cell activation signal transduction region derived from a natural protein, and has a T cell activation signal transduction ability.

In the above (3a), the sequence identity is not particularly limited as long as it is 70% or more, but is preferably 80% or more, is more preferably 85% or more, is even more preferably 90% or more, and is particularly preferably 95% or more.

In the above (3b), in a case of using a region of a protein involved in primary signal transduction, the term "several" may refer to, for example, 2 to 30, preferably refers to 2 to 20, more preferably refers to 2 to 10, and still more preferably refers to 2 to 5. In addition, in a case of using a region of a costimulatory molecule, the term "several" may refer to, for example, 2 to 15, preferably refers to 2 to 10, more preferably refers to 2 to 5, and still more preferably refers to 2 or 3. In addition, the term "mutated" may refer to any of deletion, substitution, addition, and insertion, or a combination thereof.

The number of T cell activation signal transduction regions included in the CAR of the present embodiment is not limited to one, and plural T cell activation signal transduction regions can be included. In this case, plural T cell activation signal transduction regions may be the same as or different with each other. In a preferred embodiment, the CAR includes two or more T cell activation signal transduction regions. In this case, the T cell activation signal transduction regions included in the CAR are preferably a combination of a T cell activation signal transduction region involved in primary signal transduction and a T cell activation signal transduction region involved in secondary signal transduction. Specific examples thereof include a combination of T cell activation signal transduction regions of CD3ζ and CD28, a combination of T cell activation signal transduction regions of CD3ζ and 4-1BB, a combination of T cell activation signal transduction regions of CD3ζ, CD28, and 4-1BB, and the like.

In a case of combining the T cell activation signal transduction region involved in primary signal transduction with the T cell activation signal transduction region involved in secondary signal transduction, the T cell activation signal transduction region involved in primary signal transduction is preferably located at a C-terminal side. In the above-mentioned specific examples, it is preferable that the T cell activation signal transduction region of CD3ζ be located on the C-terminal side of the T cell activation signal transduction region of CD28 or 4-1BB. In a case where both CD28 and 4-1BB are used, the regions may be located in any order, but examples of location include location in the order of CD28 and 4-1BB from an N terminal side.

In a case where only one T cell activation signal transduction region is used, it is preferable to use a T cell activation signal transduction region involved in primary signal transduction, and it is more preferable to use a T cell activation signal transduction region of CD3ζ.

<Other Regions>

The CAR of the present embodiment may include other regions in addition to the above regions. Examples of other regions include an extracellular hinge region, a cytoplasmic region, a spacer region, a signal peptide, and the like.

(Extracellular Hinge Region)

The term "extracellular hinge region" means a region linking an extracellular target antigen-binding region and a transmembrane region. In a preferred embodiment, the CAR of the present embodiment includes an extracellular hinge region.

The extracellular hinge region is not particularly limited as long as it can link a target antigen-binding region and a transmembrane region. The extracellular hinge region may be derived from a natural protein or may be artificially designed. The extracellular hinge region can be composed of, for example, about 1 to 100 amino acids, and preferably about 10 to 70 amino acids. The extracellular hinge region is preferably a region that does not interfere with a binding ability to GM2 of the target antigen-binding region and does not interfere with signal transduction by the T cell activation signal transduction region.

Examples of extracellular hinge regions include extracellular hinge regions of CD8, CD28, CD4, and the like. In addition, a hinge region of an immunoglobulin (for example, IgG4 and the like) may be used. Preferred examples include an extracellular hinge region of CD8.

An organism from which the above-mentioned proteins are derived is not particularly limited, but is preferably human. Amino acid sequences of these proteins are available from known sequence databases such as GenBank. Examples of amino acid sequences of human CD8 include amino acid sequences described above, and examples of amino acid sequences of the extracellular hinge region include an amino acid sequence set forth in SEQ ID NO: 18.

In addition, the extracellular hinge region may be a mutant of the above-mentioned extracellular hinge region derived from a natural protein. Examples of mutants of an extracellular hinge region derived from a natural protein include the following.

(4a) A polypeptide that consists of an amino acid sequence having 70% or more sequence identity (homology) to an amino acid sequence (for example, SEQ ID NO: 18) of an extracellular hinge region derived from a natural protein.

(4b) A polypeptide that consists of an amino acid sequence in which one or several amino acids are mutated in the amino acid sequence (for example, SEQ ID NO: 18) of an extracellular hinge region derived from a natural protein.

In the above (4a), the sequence identity is not particularly limited as long as it is 70% or more, but is preferably 80% or more, is more preferably 85% or more, is even more preferably 90% or more, and is particularly preferably 95% or more.

In the above (4b), the term "several" may refer to, for example, 2 to 20, preferably refers to 2 to 15, more preferably refers to 2 to 10, and still more preferably refers to 2 to 5. In addition, the term "mutated" may refer to any of deletion, substitution, addition, and insertion, or a combination thereof.

(Cytoplasmic Region)

A "cytoplasmic region" is a region adjacent to a cytoplasmic end of a transmembrane region in a transmembrane protein, and is a region consisting of about 3 to 50 amino acids. In a preferred embodiment, the CAR of the present embodiment includes a cytoplasmic region. The cytoplasmic region is not particularly limited as long as it is a region adjacent to a cytoplasmic side of the transmembrane region of the transmembrane protein. By linking the transmembrane region to the T cell activation signal transduction region via the cytoplasmic region, a structure of the transmembrane region can be stabilized. The cytoplasmic region may be derived from a natural protein or may be artificially designed. The cytoplasmic region may be composed of, for example, about 3 to 50 amino acids, preferably about 4 to 20 amino acids, and more preferably about 5 to 10 amino acids. The cytoplasmic region is preferably a region derived from the same protein as the case of the transmembrane region. By using the cytoplasmic region derived from the same protein as the case of the transmembrane region, the structure of the transmembrane region can be kept more stable.

Examples of cytoplasmic regions include a cytoplasmic region of the proteins mentioned in the transmembrane region described above. Preferred examples include a cytoplasmic region of CD8. An organism from which these proteins are derived is not particularly limited, but is preferably human. Examples of amino acid sequences of the cytoplasmic region include an amino acid sequence set forth in SEQ ID NO: 22.

In addition, the cytoplasmic region may be a mutant of the above-mentioned cytoplasmic region derived from a natural protein. Examples of mutants of a cytoplasmic region derived from a natural protein include the following.

(5a) A polypeptide that consists of an amino acid sequence having 70% or more sequence identity (homology) to an amino acid sequence (for example, SEQ ID NO: 22) of a cytoplasmic region derived from a natural protein, and that has a transmembrane region-stabling ability.

(5b) A polypeptide that consists of an amino acid sequence in which one or several amino acids are mutated in the amino acid sequence (for example, SEQ ID NO: 22) of a cytoplasmic region derived from a natural protein, and has a transmembrane region-stabling ability.

In the above (5a), the sequence identity is not particularly limited as long as it is 70% or more, but is preferably 80% or more, is more preferably 85% or more, is even more preferably 90% or more, and is particularly preferably 95% or more.

In the above (5b), the term "several" may refer to, for example, 2 to 5, preferably refers to 2 to 4, and more preferably refers to 2 or 3. In addition, the term "mutated" may refer to any of deletion, substitution, addition, and insertion, or a combination thereof.

(Spacer Region)

A "spacer region" is a short peptide that links two functional regions (domains) of a protein. In one aspect, in the CAR of the present embodiment, each of the target antigen-binding region, the transmembrane region, the T cell activation signal transduction region, and the like described above may be linked via a spacer region. The spacer region is not particularly limited, and a spacer region generally used for producing a chimeric protein may be used. A length of the spacer region may be 1 to 100 amino acids, and is preferably 10 to 50 amino acids. Examples of spacer regions include glycine-serine continuous sequences and the like.

(Signal Peptide)

A "signal peptide" is a peptide that directs localization of a membrane protein or a secreted protein. In one aspect, the CAR of the present embodiment may include a signal peptide. The signal peptide is generally a peptide consisting of about 5 to 60 amino acids present at an N terminal of a membrane protein, and is removed in a matured protein which has been completely localized.

The signal peptide used for the CAR of the present embodiment is preferably a signal peptide that directs localization of a protein to a cell membrane, and is preferably a signal peptide of a membrane protein. Examples of signal peptides include signal peptides of α chain and a β chain of a T cell receptor, CD3ζ, CD28, CD3ε, CD45, CD4, CD5, CD8, CD9, CD16, CD22, CD33, CD37, CD64, CD80, CD86, CD134, CD137, ICOS, CD154, GITR, an immunoglobulin heavy chain, an immunoglobulin light chain, and the like. Specific examples of amino acid sequences of the signal peptide include an amino acid sequence set forth in SEQ ID NO: 57.

In the CAR of the present embodiment, each of the above-mentioned regions can be located in the order of the target antigen-binding region, the transmembrane region, and the T cell activation signal transduction region from the N terminal. Each of these regions may be directly linked to each other, or may be linked via another region, a spacer sequence, or the like.

In a case where the CAR of the present embodiment includes an extracellular hinge region, the extracellular hinge region is located between the target antigen-binding region and the transmembrane region. In addition, in a case where the CAR of the present embodiment includes a cytoplasmic region, the cytoplasmic region is located between the transmembrane region and the T cell activation signal transduction region.

Furthermore, in a case where the CAR of the present embodiment includes a signal peptide, the signal peptide is located at the N terminal of the CAR.

Specific examples of the CAR of the present embodiment include a CAR including a target antigen-binding region including scFv of an anti-GM2 antibody, a transmembrane region of CD8 (or a mutant thereof), a T cell activation signal transduction region of CD28 (or a mutant thereof), a T cell activation signal transduction region of 4-1BB (or a mutant thereof), and a T cell activation signal transduction region of CD3ζ (or a mutant thereof). More preferred examples thereof include a CAR including a target antigen-binding region including scFv of an anti-GM2 antibody, an extracellular hinge region of CD8 (or a mutant thereof), a transmembrane region of CD8 (or a mutant thereof), a cytoplasmic region of CD8 (or a mutant thereof), a T cell activation signal transduction region of CD28 (or a mutant thereof), a T cell activation signal transduction region of 4-1BB (or a mutant thereof), and a T cell activation signal transduction region of CD3ζ (or a mutant thereof).

Examples of such a CAR include a CAR including an amino acid sequence selected from the group consisting of SEQ ID NOs: 40, 42, 44, and 46. In the amino acid sequences set forth in SEQ ID NOs: 40, 42, 44, and 46, the sequences at positions 1 to 19 correspond to signal peptides. Accordingly, each of matured CARs in the above-mentioned examples includes the amino acid sequence at positions 20 to 874 of the amino acid sequence set forth in SEQ ID NO: 40, the amino acid sequence at positions 20 to 884 of the amino acid sequence set forth in SEQ ID NO: 42, the amino acid sequence at positions 20 to 874 of the amino acid sequence set forth in SEQ ID NO: 44, or the amino acid sequence at positions 20 to 884 of the amino acid sequence set forth in SEQ ID NO: 46.

In a preferred embodiment, the CAR of the present embodiment consists of an amino acid sequence selected from the group consisting of SEQ ID NOs: 40, 42, 44, and 46. In addition, a matured CAR consists of an amino acid sequence selected from the group consisting of the amino acid sequence at positions 20 to 874 of the amino acid sequence set forth in SEQ ID NO: 40, the amino acid sequence at positions 20 to 884 of the amino acid sequence set forth in SEQ ID NO: 42, the amino acid sequence at positions 20 to 874 of the amino acid sequence set forth in SEQ ID NO: 44, and the amino acid sequence at positions 20 to 884 of the amino acid sequence set forth in SEQ ID NO: 46.

[Cell Expressing Anti-GM2 CAR (Anti-GM2 CAR-Expressing Cell)]

In one embodiment, the present invention provides a cell that expresses the CAR of the above embodiments.

The cell of the present embodiment expresses the CAR of the above embodiment (hereinafter also referred to as "anti-GM2 CAR"), and has the CAR on a cell surface. In GM2-expressing cells, GM2 is abundantly present on a cell surface. When the cell of the present embodiment comes into contact with a GM2-expressing cell, the cell binds to GM2 on the surface of the GM2-expressing cell via the target antigen-binding region of the anti-GM2 CAR. Accordingly, the cell of the present embodiment is activated, and thereby release of cytolytic granules and production of cytokines are caused. These cytolytic granules and cytokines destroy the GM2-expressing cell.

The cell of the present embodiment is preferably a mammalian cell, and may be, for example, a human cell or a cell of non-human mammalians such as mice, rats, cattle, sheep, horses, dogs, pigs, and monkeys, and is more preferably a human cell. The type of cells is not particularly limited, and examples include cells collected from blood, bone marrow fluid, spleen, thymus, lymph nodes, and the like; immune cells infiltrating cancer tissues such as primary tumors, metastatic tumors, and cancerous ascites; and the like. Preferable examples thereof include immune cells, and peripheral blood mononuclear cells separated from peripheral blood, and the like can be preferably used. Among the cells contained in the peripheral blood mononuclear cells, effector cells are preferable, and T cells and their precursor cells are particularly preferred cells. The type of T cells is not particularly limited, and T cells may be any T cells among αβ T cells, γδ T cells, CD8-positive T cells, cytotoxic T cells, CD4-positive T cells, helper T cells, memory T cells, naive T cells, tumor infiltrating T cells, natural killer T cells, and the like. Among these, CD8-positive T cells or cytotoxic T cells are more preferable.

It is preferable that, in addition to the anti-GM2 CAR, the cell of the present embodiment further express at least one of interleukin (IL)-7 or a chemokine (C—C motif) ligand 19 (CCL 19). In a preferred embodiment, the cell of the present embodiment is a cell that expresses (i) the anti-GM2 CAR, and (ii) at least one of IL-7 or CCL19. More preferably, the cell of the present embodiment is a cell that expresses the anti-GM2 CAR, IL-7, and CCL19.

IL-7 is a cytokine essential for survival of T cells, and is produced by non-hematopoietic cells such as stromal cells in bone marrow, thymus, and lymphoid organs and tissues, but production thereof by T cells is hardly recognized.

Meanwhile, CCL19 is mainly produced from dendritic cells and macrophages in lymph nodes, and has a function of causing migration of T cells and B cell, and mature dendritic cells via its receptor, which is a CC chemokine receptor 7 (Chemokine (C—C motif) Receptor 7: CCR7).

An organism from which IL-7 and CCL19 are derived is not particularly limited, but is preferably human. Amino acid sequences of these proteins are available from known sequence databases such as GenBank. For example, examples of amino acid sequences of human IL-7 include an amino acid sequence registered as GenBank No: NM_000880.3 (SEQ ID NO: 59), and the like. In addition, examples of amino acid sequences of human CCL19 include an amino acid sequence registered as GenBank No: NM_006274.2 (SEQ ID NO: 61), and the like. IL-7 and CCL19 have a signal peptide, and the signal peptide is removed from mature proteins. For example, in the amino acid sequence set forth in SEQ ID NO: 59 of human IL-7, the sequence at positions 1 to 25 correspond to a signal peptide. Furthermore, for example, in the amino acid sequence set forth in SEQ ID NO: 61 of human CCL19, the sequence at positions 1 to 21 correspond to a signal peptide.

Furthermore, IL-7 and CCL19 may be mutants of the natural proteins described above. Examples of mutants of IL-7 include the following.

(6a) A polypeptide that consists of an amino acid sequence having 70% or more sequence identity (homology) to an amino acid sequence of natural IL-7 (for example, SEQ ID NO: 59), and that has a T cell-immune-function-promoting function.

(6b) A polypeptide that consists of an amino acid sequence in which one or several amino acids are mutated in the amino acid sequence of natural IL-7 (for example, SEQ ID NO: 59), and that has the T cell-immune-function-promoting function.

In addition, examples of mutants of CCL19 include the following.

(7a) A polypeptide that consists of an amino acid sequence having 70% or more sequence identity (homology) to an amino acid sequence of natural CCL19 (for example, SEQ ID NO: 61), and that has the T cell-immune-function-promoting function.

(7b) A polypeptide that consists of an amino acid sequence in which one or several amino acids are mutated in the amino acid sequence of natural CCL19 (for example, SEQ ID NO: 61), and that has the T cell-immune-function-promoting function.

The term “T cell-immune-function-promoting function” means a function to maintain or promote survival, growth, cytotoxic activity, migration activity, infiltration activity to tumor tissue, and the like of T cells.

In the above (6a) and (7a), the sequence identity is not particularly limited as long as it is 70% or more, but is preferably 80% or more, is more preferably 85% or more, is even more preferably 90% or more, and is particularly preferably 95% or more.

In addition, in the above (6b) and (7b), the term “several” may refer to, for example, 2 to 30, preferably refers to 2 to 20, more preferably refers to 2 to 10, and still more preferably refers to 2 to 5. In addition, the term “mutated” may refer to any of deletion, substitution, addition, and insertion, or a combination thereof.

In addition, mutants of IL-7 and CCL19 may be a mutant in which a signal peptide of these proteins is changed to another signal peptide, or may be a mutant in which a signal peptide is removed. Preferably, mutants of IL-7 and CCL 19 have a signal peptide of secreted proteins and are secreted extracellularly.

In a case where the cell of the present embodiment is an isolated T cell, expression of at least one of IL-7 or CCL19 together with the anti-GM2 CAR promotes the immune function of the T cell, and thereby the T cell becomes excellent in cytotoxic activity against GM2-expressing cells, invasion to tumor tissue, and survival ability in a tumor microenvironment.

In addition, the cell of the present embodiment may express a suicide gene in addition to the anti-GM2 CAR. Expression of the suicide gene in the cell of the present embodiment enables induction of apoptosis in the cell of the present embodiment as necessary. The suicide gene is not particularly limited, and a known suicide gene can be used. Examples of suicide genes include a thymidine kinase (HSV-TK) gene of herpes simplex virus, an inducible caspase 9 gene, and the like. Cells expressing HSV-TK can induce cell death by coexistence with ganciclovir. In addition, cells expressing inducible caspase 9 can induce cell death by coexistence with a chemical induction of dimerization (CID) such as AP1903. Amino acid sequences of the suicide genes are available from known sequence databases such as GenBank. In addition, sequences of commercially available vectors including a suicide gene, and the like can also be used.

The cell of the present embodiment can also be said to be a cell (preferably a T cell) including the anti-GM2 CAR. Preferred examples of the cell of the present embodiment can be said to be a cell (preferably a T cell) including the anti-GM2 CAR, and at least one of IL-7 or CCL19. More preferred examples of the cell of the present embodiment can be said to be a cell (preferably a T cell) including the anti-GM2 CAR, IL-7, and CCL19. Even more preferred examples of the cell of the present embodiment can be said to be a cell (preferably a T cell) including the anti-GM2 CAR, IL-7, CCL19, and a suicide gene.

The cell of the present embodiment can be obtained by introducing a polynucleotide or a vector including a base sequence encoding the anti-GM2 CAR which will be described later into a cell.

[Polynucleotide Including Base Sequence Encoding the Anti-GM2 CAR]

In one embodiment, the present invention provides a polynucleotide including a base sequence that encodes the anti-GM2 CAR.

The polynucleotide of the present embodiment is not particularly limited as long as it includes a base sequence encoding the anti-GM2 CAR. The anti-GM2 CAR is as described above in the section of [Chimeric antigen receptor (anti-GM2 CAR)]. The polynucleotide of the present embodiment preferably includes a base sequence encoding the amino acid sequence of the anti-GM2 CAR exemplified in the section of [Chimeric antigen receptor (anti-GM2 CAR)] described above.

Example of base sequences encoding a target antigen-binding region include a base sequence encoding scFv of an anti-GM2 antibody. More specifically, a polynucleotide including a base sequence encoding the amino acid sequence set forth in SEQ ID NO: 2 and a base sequence encoding the amino acid sequence set forth in SEQ ID NO: 4 can be exemplified. As the base sequence encoding the amino acid sequence set forth in SEQ ID NO: 2, a base sequence set forth in SEQ ID NOs: 1, 49, 51, or 53 can be exemplified. In addition, as the base sequence encoding the amino acid sequence set forth in SEQ ID NO: 4, a base sequence set forth in SEQ ID NO: 3, 50, 52, or 54 can be exemplified.

These base sequences are preferably linked by a base sequence encoding a linker. The linker is as described in the section of "Chimeric antigen receptor" described above. For example, as a base sequence encoding the linker 15 described above, a base sequence set forth in SEQ ID NO: 5 or 55 can be exemplified. In addition, as a base sequence encoding the linker 25, a base sequence set forth in SEQ ID NO: 7 or 56 can be exemplified.

Specific examples of base sequences encoding scFv of an anti-GM2 antibody include a base sequence set forth in SEQ ID NO: 9, 11, 13, or 15, and the like.

A base sequence encoding the target antigen-binding region is preferably a codon-optimized base sequence according to the species of cells to be introduced, and in a case of introduction into human cells, a human-codon-optimized base sequence is preferred.

In addition, base sequences encoding a transmembrane region and a T cell activation signal transduction region are available from known sequence databases such as GenBank. Furthermore, in a case where GM2 CAR includes other regions such as an extracellular hinge region, base sequences encoding the other regions are also available from known sequence databases such as GenBank.

For example, in a case where a transmembrane region of human CD8 is used as the transmembrane region, examples of base sequences encoding human CD8 include a base sequence registered as GenBank No: NM_001768.6, and the like. As base sequences encoding the transmembrane region, a base sequence set forth in SEQ ID NO: 19 can be exemplified.

Furthermore, for example, in a case where a T cell activation signal transduction region of human CD3ζ, human CD28, or human 4-1BB is used as the T cell activation signal transduction region, examples of base sequences encoding human CD3ζ human CD28, and human 4-1BB respectively include base sequences registered as GenBank Nos: NM_000734.3, NM_006139.2, and NM_001561.5, and the like. As respective base sequences encoding the T cell activation signal transduction regions of human CD3ζ, human CD28, and human 4-1BB, base sequences set forth in SEQ ID NOs: 27, 23, and 25 can be exemplified.

Furthermore, for example, in a case where an extracellular hinge region of human CD8 is used as the extracellular hinge region, a base sequence set forth in SEQ ID NO: 17 can be exemplified as a base sequence encoding the extracellular hinge region.

Furthermore, for example, in a case where a cytoplasmic region of human CD8 is used as the cytoplasmic region, a base sequence set forth in SEQ ID NO: 21 can be exemplified as a base sequence encoding the cytoplasmic region.

The base sequence encoding each of the above regions is not limited to known base sequences, and any sequence may be used as long as it is a base sequence encoding each of the above regions. Due to degeneracy of the genetic code, a plurality of codons corresponding to one amino acid are present. Accordingly, many base sequences encoding the same amino acid sequence are present. The base sequence encoding each of the above regions may be any of plural base sequences generated by degeneracy of the genetic code, as long as it is a base sequence encoding these regions.

A base sequence encoding each of the above-mentioned regions is preferably a codon-optimized base sequence according to the species of cells to be introduced, and in a case of introduction into human cells, a human-codon-optimized base sequence is preferred.

In addition, the base sequence encoding each of the above-mentioned regions may be a base sequence encoding a mutant of each region derived from a natural protein. Mutants of each region are as described above in the section of [Chimeric antigen receptor (anti-GM2 CAR)].

Respective base sequence encoding each region of the anti-GM2 CAR is preferably located in the order of the target antigen-binding region, the transmembrane region, and the T cell activation signal transduction region from the 5' side. In a case of using a signal peptide, an extracellular hinge region, or the like, it is preferable that the signal peptide be located at the 5' side of the target antigen-binding region, and the extracellular hinge region be located between the target antigen-binding region and the transmembrane region. The base sequences encoding these regions may be directly linked, or may be linked via a base sequence encoding a spacer region. The spacer region is as described above in the section [Chimeric antigen receptor (anti-GM2 CAR)].

Specific examples of base sequences encoding the anti-GM2 CAR include a base sequence selected from the group consisting of SEQ ID NOs: 39, 41, 43, and 45, and the like.

The polynucleotide of the present embodiment can be obtained by linking polynucleotides consisting of a base sequence encoding each region of the anti-GM2 CAR directly or via a spacer sequence. The polynucleotides encoding each region of the anti-GM2 CAR may be obtained by chemical synthesis with a known method according to the base sequence of each region. In addition, by PCR, isothermal amplification, and the like using DNA extracted from T cells or the like, and cDNA obtained by reverse transcribing RNA extracted from T cells or the like as a template, polynucleotides encoding each region may be amplified and obtained. The polynucleotides encoding each region thus obtained may be subjected to modification such as substitution, deletion, addition, and insertion within a range not losing functions of each region after translation.

The polynucleotide of the present embodiment may include, in addition to the base sequence encoding the anti-GM2 CAR, regulatory sequences such as a promoter, an enhancer, a poly A addition signal, and a terminator, base sequences encoding other proteins, and the like.

Examples of other proteins include IL-7 and CCL19. Base sequences encoding these proteins are available from known sequence databases such as GenBank. For example, in a case where human IL-7 is used, examples of base sequences encoding human IL-7 include a base sequence registered as GenBank No: NM_002190.2 (SEQ ID NO: 58), and the like. In addition, in a case where human CCL19 is used, examples of base sequences encoding human CCL19 include a base sequence registered as GenBank No: NM_006274.2 (SEQ ID NO: 60), and the like.

Furthermore, the base sequences encoding these proteins are not limited to known base sequences, and any sequences may be used as long as they are base sequences encoding these proteins, and any of plural base sequences generated by degeneracy of the genetic code may be used. The base sequences encoding these proteins are preferably a codon-optimized base sequence according to the species of cells to be introduced, and in a case of introduction into human cells, a human-codon-optimized base sequence is preferred.

Furthermore, the base sequences encoding these proteins may encode mutants of natural IL-7 and natural CCL19. These mutants are as described above in the section
[Cell Expressing Anti-GM2 CAR (Anti-GM2 CAR-Expressing Cell)]

Examples of other proteins include a suicide gene. The suicide gene is as described above in the section [Cell expressing anti-GM2 CAR (anti-GM2 CAR-expressing cell)]. A base sequence encoding the suicide gene is available from known sequence databases such as GenBank. In addition, sequences of commercially available vectors including a suicide gene can also be used.

In a case where the polynucleotide of the present embodiment includes a base sequence encoding another protein, a base sequence encoding a self-cleaving type peptide such as 2A peptide, an internal ribozyme entry site (IRES) sequence, and the like may be interposed between the base sequence encoding the anti-GM2 CAR and the base sequence encoding another protein. In addition, in a case where two or more other proteins are present, a self-cleaving type peptide, an IRES, and the like may be interposed between the other proteins. By interposing these sequences, plural proteins can be expressed independently from one promoter.

Examples of 2A peptides include 2A peptides of picornavirus, rotavirus, insect virus, aphthovirus, trypanosoma virus, and the like. As a specific example, an amino acid sequence of 2A peptide (F2A) of picornavirus is shown in SEQ ID NO: 62. A base sequence encoding 2A peptide is preferably a codon-optimized base sequence according to the species of cells to be introduced, and in a case of introduction into human cells, a human-codon-optimized base sequence is preferred.

In addition, the polynucleotide of the present embodiment may be a polynucleotide having regulatory sequences such as a promoter, an enhancer, a poly A addition signal, and a terminator for each of protein-coding sequences of the base sequence encoding the anti-GM2 CAR and the base sequence encoding other proteins. Furthermore, the polynucleotide may be a polynucleotide in which some protein-coding sequences independently have regulatory sequences, and the other-protein-coding sequences linked via 2A peptide, IRES, or the like have common regulatory sequences.

[Vector Including Base Sequence Encoding Anti-GM2 CAR]

In one embodiment, the present invention provides a vector including a base sequence that encodes the anti-GM2 CAR.

The polynucleotide of the embodiment may be in a form of a vector. The type of vector is not particularly limited, and a commonly used expression vectors and the like can be used. The vector may be linear or circular, and may be a non-viral vector such as a plasmid, may be a viral vector, or may be a transposon vector. Examples of vectors include viral vectors, plasmid vectors, episomal vectors, artificial chromosome vectors, and the like.

Examples of viral vectors include Sendai virus vectors, retrovirus (including lentivirus) vectors, Adenovirus vectors, adeno-associated virus vectors, herpes virus vectors, vaccinia virus vectors, pox virus vectors, polio virus vectors, sindbis virus vectors, rhabdovirus vectors, paramyxovirus vectors, orthomyxovirus vectors, and the like.

Examples of plasmid vectors include plasmid vectors for animal cell expression, such as pA1-11, pXT1, pRc/CMV, pRc/RSV, and pcDNAI/Neo.

An episomal vector is a vector capable of extrachromosomal autonomous replication. Examples of episomal vectors include vectors containing sequences which are necessary for autonomous replication and are derived from EBV, SV40, and the like as vector elements. Specific examples of vector elements necessary for autonomous replication include a replication start point, and a gene encoding a protein that binds to a vector at the replication start point to control replication. Examples thereof include oriP, which is a replication start point, and EBNA-1 gene in a case of EBV, and ori, which is a replication start point, and a SV40LT gene in a case of SV40.

Examples of artificial chromosome vectors include Yeast artificial chromosome (YAC) vectors, Bacterial artificial chromosome (BAC) vectors, P1-derived artificial chromosome (PAC) vectors, and the like.

Preferred examples of the vector of the present embodiment include viral vectors, and more preferred examples thereof include retrovirus vectors. Examples of the retrovirus vectors include a pMSGV1 vector (Tamada k et al., Clin Cancer Res 18: 6436-6445 (2012)) and a pMSCV vector (manufactured by Takara Bio Inc.). By using a retrovirus vector, a gene in the vector is incorporated into the genome of a host cell, and thereby the gene can be stably expressed in the host cell for a long time.

In addition to the base sequences described above in the section [Polynucleotide including base sequence encoding anti-GM2 CAR], the vector of the present embodiment may include a replication start point; a base sequence encoding a protein that binds to the vector at the replication start point to control replication; a base sequence encoding a marker gene such as a drug resistance gene and a reporter gene; and the like.

The base sequence encoding the anti-GM2 CAR is preferably located within the vector so as to be expressed under the control of an appropriate promoter. In addition, in a case where the base sequences encoding other proteins are included, these base sequences are preferably located within the vector so as to be expressed under the control of an appropriate promoter. Examples of promoters include an SRα promoter, an SV40 early stage promoter, an LTR of retrovirus, a cytomegalovirus (CMV) promoter, a Rous sarcoma virus (RSV) promoter, a herpes simplex virus thymidine kinase (HSV-TK) promoter, an EF1α promoter, a metallothionein promoter, a heat shock promoter, and the like. In addition, an enhancer of an IE gene of human CMV may be used together with the promoter. As an example, a CAG promoter (including a cytomegalovirus enhancer, a chicken β-actin promoter, and a poly A signal site of a β-globin gene), and the like can be mentioned. Furthermore, as described above in [Polynucleotide including base sequence encoding anti-GM2 CAR], transcriptions thereof may be performed under control of a common promoter by locating a base sequence encoding a self-cleaving type peptide or an IRES between each of protein-coding sequences.

In a preferred embodiment, in addition to the base sequence encoding the anti-GM2 CAR, the vector of the present embodiment further includes at least one of a base sequence encoding IL-7 and a base sequence encoding CCL19. In a more preferred embodiment, in addition to the base sequence encoding anti-GM2 CAR, the vector of the present embodiment further includes a base sequence encoding IL-7 and a base sequence encoding CCL19.

The vector of the present embodiment preferably includes a base sequence encoding the anti-GM2 CAR functionally linked to an appropriate promoter. More preferably, the vector of the present embodiment includes a base sequence in which the base sequence encoding the anti-GM2 CAR, the base sequence encoding IL-7, and the base sequence encoding CCL19 are linked via a base sequence encoding a self-cleaving type peptide or an IRES. The base sequence is functionally linked to an appropriate promoter. The phrase "functionally linked to a promoter" means that a base sequence is linked downstream of a promoter so as to be expressed under the control of the promoter. In the above example, location order of the base sequence encoding the anti-GM2 CAR, the base sequence encoding IL-7, and the base sequence encoding CCL19 is not particularly limited, and may be any location order.

[Method for Producing Cell Expressing Anti-GM2 CAR]

In one embodiment, the present invention provides a method for producing a cell expressing the anti-GM2 CAR, the method including introducing a polynucleotide or vector including a base sequence encoding the anti-GM2 CAR into a cell.

The cell expressing the anti-GM2 CAR of the above embodiment (hereinafter also referred to as "anti-GM2 CAR-expressing cell") can be obtained by introducing a polynucleotide or a vector including the base sequence encoding the anti-GM2 CAR of the above embodiment into a cell. The polynucleotide or the vector introduced into a cell is retained in the cell in a state capable of expressing the anti-GM2 CAR. The phrase "state capable of expressing" means a state in which the base sequence encoding the anti-GM2 CAR can be transcribed and translated.

A method for introducing a polynucleotide or a vector into a cell is not particularly limited, and known methods can be used. Examples thereof include a viral infection method, a lipofection method, a microinjection method, a calcium phosphate method, a DEAE-dextran method, an electroporation method, a method using transposon, a particle gun method, and the like.

In addition, in a case where the vector is a retrovirus vector, appropriate packaging cells may be selected based on LTR sequences and packaging signal sequences included in the vector, and retrovirus particles may be prepared by using the same. Examples of packaging cells include PG13, PA317, GP+E-86, GP+envAm-12, Psi-Crip, and the like. In addition, 293 cells or 293T cells with high transfection efficiency can be used as packaging cells. Since various retrovirus vectors and packaging cells that can be used for packaging the vector are widely commercially available, these commercially available products may be used. For example, it is possible to use GP2-293 cells (manufactured by Takara Bio Inc.), Plat-GP cells (manufactured by Cosmo Bio Co., Ltd.), PG13 cells (CRL-10686 manufactured by ATCC), PA317 cells (CRL-9078 manufactured by ATCC), and the like, and a commercially available kit such as Retrovirus packaging Kit Eco (manufactured by Takara Bio Inc.) may be used.

In a case where other foreign proteins such as IL-7, CCL19, and a suicide gene are expressed in the anti-GM2 CAR-expressing cells, base sequences encoding these other proteins may be incorporated into a vector including a base sequence encoding the anti-GM2 CAR, or may be incorporated into another vector. In a case where base sequences encoding other proteins are included in the other vector, the vector can be introduced into a cell simultaneously or separately with the vector including the base sequence encoding the anti-GM2 CAR.

In addition, the anti-GM2 CAR-expressing cell may be produced by incorporating a polynucleotide including the base sequence encoding the anti-GM2 CAR in the genome of a cell so that the polynucleotide can be expressed under the control of an appropriate promoter, by using known gene-editing techniques and the like. Examples of gene-editing techniques include techniques using endonucleases such as zinc finger nuclease, transcription activation-like effector nuclease (TALEN), Clustered Regularly Interspaced Short Palindromic Repeat (CRISPR)-Cas system, and pentatricopeptide repeat (PPR). In a case where other foreign proteins are expressed in the anti-GM2 CAR-expressing cell, similarly, a polynucleotide including the base sequence encoding the other foreign protein may be incorporated into the genome of the cell so that the polynucleotide can be expressed under the control of an appropriate promoter, by using gene-editing techniques and the like. For example, a method of incorporating a polynucleotide including a base sequence encoding the anti-GM2 CAR (or other proteins) functionally linked to an appropriate promoter into a non-coding region and the like in a cell genome; a method of incorporating a polynucleotide including a base sequence encoding the anti-GM2 CAR (or other proteins) downstream of an endogenous promoter in a cell genome; and the like are exemplified. Examples of endogenous promoters include promoters of TCRα and TCRβ, and the like.

After introducing a polynucleotide or a vector including a base sequence encoding the anti-GM2 CAR into a cell, expression of the anti-GM2 CAR in the cell can be confirmed by a known method such as flow cytometry, RT-PCR, Northern blotting, Western blotting, ELISA, and fluorescent immunostaining. In addition, expression of other foreign proteins such as IL-7 and CCL19 can also be similarly confirmed by known methods.

[Pharmaceutical Composition Including Anti-GM2 CAR-Expressing Cell]

In one embodiment, the present invention provides a pharmaceutical composition including the anti-GM2 CAR-expressing cell.

The anti-GM2 CAR-expressing cell show specific cytotoxic activity against GM2-expressing cells. Accordingly, the anti-GM2 CAR-expressing cell can be used to treat or prevent a disease involving a GM2-expressing cell. Since GM2 is expressed in a wide range of tumor cells including lung cancer, neuroblastoma, glioma, melanoma, malignant mesothelioma, myeloma, and the like, the pharmaceutical composition including the anti-GM2 CAR-expressing cell can be used as a pharmaceutical composition for treating or preventing tumors. The tumor may be a tumor generated from any of bone tissue, cartilage tissue, fat tissue, muscle tissue, vascular tissue, and hematopoietic tissue. Examples of tumors include cancer such as glioma, melanoma, malignant mesothelioma, lung cancer, pancreatic cancer, head and neck cancer, liver cancer, uterine cancer, bladder cancer, biliary cancer, esophageal cancer, testicular tumor, thyroid cancer, brain cancer, prostate cancer, colon cancer, kidney cancer, ovarian cancer, breast cancer, adenocarcinoma, squamous cell carcinoma, adenosquamous cell carcinoma, anaplastic cancer, large cell cancer, small cell cancer, skin cancer, vaginal cancer, neck cancer, spleen cancer, trachea cancer, bronchial cancer, small intestine cancer, stomach cancer, gallbladder cancer, and testicular cancer; sarcoma such as osteosarcoma, chondrosarcoma, Ewing sarcoma, malignant hemangioendothelioma, malignant schwannoma, and soft tissue sarcoma; blastoma such as neuroblastoma, hepatoblastoma, medulloblastoma, nephroblastoma, pancreatoblastoma, pleuropulmonary blastoma, and retinoblastoma; germ cell tumor; blood cancer such as lymphoma, leukemia, and myeloma; and the like, but examples are not limited thereto. In particular, the pharmaceutical composition of the present embodiment is suitable as a pharmaceutical composition for treating or preventing tumors expressing GM2. Examples of tumors expressing GM2 include lung cancer, neuroblastoma, glioma, melanoma, malignant mesothelioma, myeloma, and the like, but examples are not limited thereto. Whether or not a tumor expresses GM2 can be confirmed by, for example, a known method using an anti-GM2 antibody or the like. Examples of known methods include flow cytometry, ELISA, immunostaining, fluorescent immunostaining, and the like. Cells (preferably T cells) that express any one or both of IL-7 and CCL19 in addition to the anti-GM2 CAR exert strong cytotoxic activity against even solid tumors as long as they are tumors expressing GM2. For this reason, the pharmaceutical composition of the present embodiment including cells (preferably T cells) expressing the anti-GM2 CAR, and any one or both of IL-7 and CCL19 can be particularly preferably used for solid tumors expressing GM2. Accordingly, the pharmaceutical composition for treating or preventing solid tumors, which includes a cell (preferably T cell) expressing the anti-GM2 CAR, and any one or both of IL-7 and CCL19, is a preferred example of the pharmaceutical composition of the present embodiment. The term "solid tumor" means a tumor other than blood cancer arising from hematopoietic tissues, and includes epithelial cell cancers and non-epithelial cell cancers.

The pharmaceutical composition of the present embodiment may include other components such as a pharmaceutically acceptable carrier, in addition to the anti-GM2 CAR-expressing cell. Examples of other components include, in addition to a pharmaceutically acceptable carrier, a T cell activating factor such as cytokines, an immunostimulant, an immune checkpoint inhibitor, cells expressing other CAR, an anti-inflammatory agent, and the like, but examples are not limited thereto. Examples of pharmaceutically acceptable carriers include a cell culture medium, a physiological salt solution, a phosphate buffer solution, a citrate buffer solution, and the like.

The pharmaceutical composition of the present embodiment can be administered by a known method, but preferably can be administered to a patient by injection or infusion. An administration route is preferably intravenous administration, but is not limited thereto, and administration may be performed by injection into a tumor, or the like.

The pharmaceutical composition of the present embodiment may include a therapeutically effective amount of the anti-GM2 CAR-expressing cells. The term "therapeutically effective amount" means an amount of an agent effective for treating or preventing a disease. The therapeutically effective amount may vary depending on a disease state, age, sex, body weight, and the like of a subject for administration. In the pharmaceutical composition of the present embodiment, the above-mentioned therapeutically effective amount of the anti-GM2 CAR-expressing cells may be, for example, an amount that enables the anti-GM2 CAR-expressing cells to suppress growth of tumors.

A dose and an administration interval of the pharmaceutical composition of the present embodiment can be appropriately selected depending on age, sex, body weight, and the like of a subject for administration; the type, degree of progression, symptoms, and the like of a disease; an administration method; and the like. As a dose, a therapeutically effective amount can be administered, and examples thereof include $1\times10^4$ to $1\times10^{10}$ cells, preferably $1\times10^5$ to $1\times10^9$ cells, and more preferably $5\times10^6$ to $5\times10^8$ cells as the number of cells to be administered per administration.

An administration interval of the pharmaceutical composition of the present embodiment may be, for example, every week, every 10 to 30 days, every month, every 3 to 6 months, every year, or the like. In addition, since the anti-GM2 CAR-expressing cells can be autonomously proliferated in the body of a subject for administration, they may be administered only once. Alternatively, the number of the anti-GM2 CAR-expressing cells in a body may be monitored after administration, and an administration period may be determined according to the result.

In addition, the pharmaceutical composition of the present embodiment can be used in combination with other anticancer agents. Examples of other anticancer agents include alkylating drugs such as cyclophosphamide, antimetabolites such as pentostatin, molecularly targeted drugs such as rituximab, kinase inhibitors such as imatinib, proteasome inhibitors such as bortezomib, calcineurin inhibitors such as cyclosporin, anti-cancer antibiotics such as idarubicin, plant alkaloids such as irinotecan, platinum preparations such as cisplatin, hormone therapy drugs such as tamoxifen, immunoregulatory drugs such as nivolumab and pembrolizumab, and the like, but examples are not limited thereto.

In addition, in other aspects, the present invention provides 1) use of the anti-GM2 CAR-expressing cell in production of a pharmaceutical composition for treating or preventing a tumor; 2) a method for treating or preventing a GM2-expressing tumor, the method including administering the anti-GM2 CAR-expressing cell to a subject (for example, a patient suffering from a tumor expressing GM2, a patient who has undergone surgical removal of a tumor, and the like); 3) the anti-GM2 CAR-expressing cell for use in treatment or prevention of a tumor; and 4) use of the anti-GM2 CAR-expressing cell for treating or preventing a tumor.

Furthermore, in another aspect, the present invention provides a kit for producing the anti-GM2 CAR-expressing cell, the kit including the vector of the above-described embodiment. The kit is not particularly limited as long as it includes the vector of the above-described embodiment, and the kit may include instructions for producing the anti-GM2 CAR-expressing cell, a reagent used to introduce the vector into a cell, and the like.

EXAMPLES

Hereinafter, the present invention will be described by examples, but the present invention is not limited by the following examples.

[Example 1] Preparation of Anti-GM2 CAR-Expressing T Cells Expressing IL-7 and CCL 19 (Selection of T Cell Immune Function-Promoting Factor)

At least hundreds of molecules capable of controlling T cell function are present in a living body. The inventors of the present invention have selected IL-7 and CCL19 among a vast number of combinations as an immune function-promoting factor for enhancing an antitumor effect in CAR-T cells.

The above-mentioned IL-7 is a cytokine essential for survival of T cells, and is produced by non-hematopoietic cells such as stromal cells present in bone marrow, thymus, lymph organs and tissues, and the like. Meanwhile, an ability to produce IL-7 is hardly recognized in T cells.

In addition, the above-mentioned CCL19 is mainly produced from dendritic cells and macrophages in lymph nodes, and has a function of causing migration of T cells and B cell, and mature dendritic cells via its receptor, CCR7.

(ScFv Sequences of Anti-GM2 CAR)

Sequences of anti-GM2 scFvs were designed based on sequences of known GM2 antibodies. In order to compare the order of VL and VH and types of linkers, each DNA fragment of VL-linker 15-VH (SEQ ID NO: 9: VL15VH), VL-linker 25-VH (SEQ ID NO: 11: VL25VH), VH-linker 15-VL (SEQ ID NO: 13: VH15VL), and VH-linker 25-VL (SEQ ID NO: 15: VH 25VL) was synthesized. In the following examples, VL15 VH was used as the anti-GM2 scFv sequence, unless otherwise specified.

(Preparation of Anti-GM2 CAR-Expressing Vector Expressing IL-7 and CCL19)

Figure 1B:
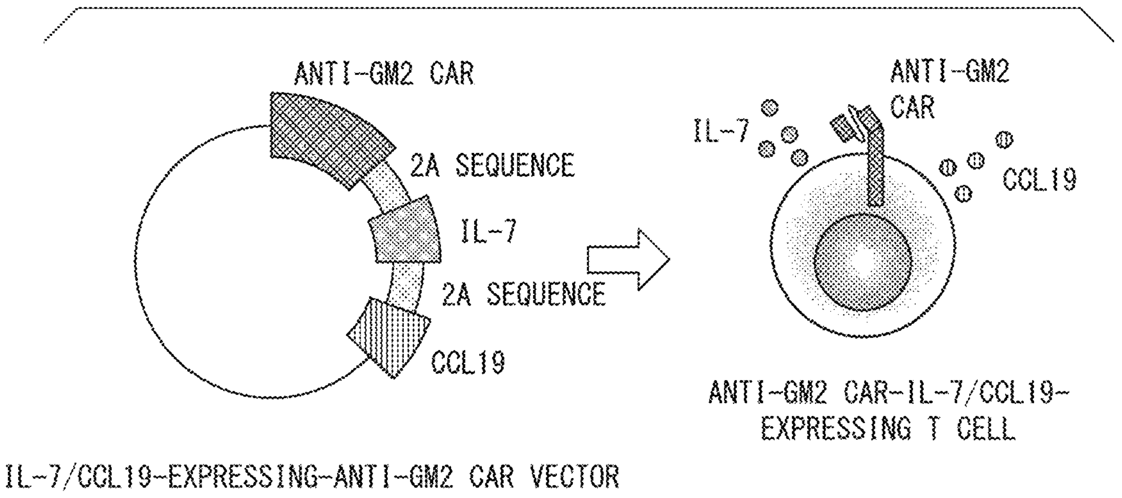
FIG. 1B is a schematic view showing an IL-7/CCL19-expressing-anti-GM2 CAR vector and an anti-GM2 CAR-IL-7/CCL19-expressing T cell into which the vector has been introduced.

First, chemical synthesis was performed on a DNA fragment of IL-7-F2A-CCL19 (SEQ ID NO: 33: IL-7-F2A-CCL19) encoding human IL-7 (no stop codon), and subsequent F2A and human CCL19. Next, using the existing mouse anti-CD20 CAR-IL-7/CCL19 vector obtained by inserting a construct consisting of a mouse anti-CD20 scFv, a mouse CD8 transmembrane region, a mouse CD28-4-1BB-CD3ζ intracellular signal motif, and a mouse IL-7-F2A-mouse CCL19 into a pMSGV1 retrovirus expression vector (Tamada k et al., Clin Cancer Res 18:6436-6445 (2012)), a region of the mouse IL-7-F2A-CCL19 in the vector was replaced with the synthesized human IL-7-F2A-CCL19 DNA fragment (SEQ ID NO: 33) by restriction enzyme (NsiI and SalI) treatment and ligation. Furthermore, chemical synthesis was performed on a human anti-CD20 CAR DNA fragment (SEQ ID NO: 37: anti-CD20 CAR) consisting of a human anti-CD20 scFv, a human CD8 transmembrane region, and a human CD28-4-1BB-CD3ζ intracellular signal motif, and a mouse anti-CD20 CAR region in the vector was replaced with this DNA fragment by restriction enzyme (NcoI and EcoI) treatment and ligation. Finally, the DNA fragments (SEQ ID NOs: 9, 11, 13, and 15) encoding human anti-GM2 scFv were chemically synthesized, and the anti-CD20 scFv in the vector was replaced with this DNA fragment by restriction enzyme (NcoI and NotI) treatment and ligation. The construct of the anti-GM2 CAR DNA fragment is shown in FIG. 1A, and a location drawing of the obtained vector is shown in FIG. 1B.

(Preparation of Anti-GM2 CAR-Expressing Vector Expressing IL-7/CCL19 and HSV-tk)

In CAR-T cell therapy, a strong immune response to a target antigen may cause systemic side effects such as cytokine release syndrome. In order to cope with such a problem, a CAR construct was produced in which a herpes virus-derived thymidine kinase gene, HSV-tk, was introduced as a suicide gene. When this construct was transfected and the HSV-tk was expressed in CAR-T cells, addition of ganciclovir, which is a cytomegalovirus therapeutic drug, induces apoptosis of the CAR-T cells to kill them, and ganciclovir administration allows control of CAR-T cells in the body.

First, IL-7-F2A-CCL19-F2A-HSV-tk DNA fragment (SEQ ID NO: 35: IL-7-F2A-CCL19-HSV-tk) was chemically synthesized. Next, the region of IL-7-F2A-CCL19 in the anti-GM2 CAR-expressing vector (SEQ ID NO: 39) expressing IL-7 and CCL19 was replaced with the synthesized IL-7-F2A-CCL19-HSV-tk DNA fragment (SEQ ID NO: 35) by restriction enzyme (NsiI and SalI) treatment and ligation, and thereby an anti-GM2 CAR expression vector (SEQ ID NO: 47) expressing IL-7/CCL19 and HSV-tk was produced.

(Production of Retrovirus into which IL-7/CCL19 Expressing-Anti-GM2 CAR Vector had been Introduced)

A retrovirus was produced for gene transfection into T cells. Using LIPOFECTAMINE™ 3000 (transfection reagent) (manufactured by Life Technology Inc.), the above-mentioned IL-7/CCL19 expression-anti-GM2 CAR vector and p-Ampho plasmid (manufactured by Takara Bio Inc.) was transfected into a GP2-293 packaging cell line (manufactured by Takara Bio Inc.), and thereby a retrovirus into which the IL-7/CCL19 expressing-anti-GM2 CAR vector had been introduced was produced. The supernatant containing the retrovirus was recovered 48 hours after the transfection.

As a culture solution of the GP2-293 cells, DMEM to which 10% FCS, 100 U/ml penicillin, and 100 mg/ml streptomycin were added was used. In addition, as a culture solution of T cells used in Examples to be described later, GT-T 551 containing 2.0% human AB type serum (manufactured by Sigma), 1% Penicillin-Streptomycin (manufactured by Wako Pure Chemical Industries, Ltd.), and 2.5 μg/ml amphotericin B (manufactured by Bristol-Myers Squibb) was used.

(Genetic Transduction of T Cells)

Peripheral blood mononuclear cells were collected from the blood of healthy donors, and were cultured with $2\times10^6$ IL-2 (200 IU/ml: manufactured by Peprotech) in a 5% $CO_2$ incubator at 37° C. for 3 days on a plate on which an anti-CD3 monoclonal antibody (5 μg/ml) and RETRONECTIN® (transduction enhancer for retroviral gene transfer) (registered trademark: manufactured by Takara Bio Inc., 25 μg/ml) were layered to activate T cells. On the second day after the start of culture, 500 μl/well of the supernatant containing the retrovirus into which the IL-7/CCL19 expressing-anti-GM2 CAR vector produced above was introduced was added to a surface-untreated 24-well plate that was coated in advance with 25 μg/ml of RETRONECTIN® (manufactured by Takara Bio Inc.), and thereby a retrovirus preload plate was produced by centrifugation at 2000 g for 2 hours. A total of two plates was produced, and after the completion of centrifugation, the plates were washed with 1.5% BSA/PBS and stored at 4° C. until being used. On the third day of culture, activated cells were recovered from the plate and prepared as cell suspension ($1\times10^5$ cells/ml). A first retrovirus infection was performed by adding 1 ml per well of this cell suspension to the retrovirus preload plate, and culturing in a 5% $CO_2$ incubator at 37° C. for 24 hours in the presence of IL-2 (a final concentration of 200 IU/ml). On the next day (culture day 4), a second retrovirus infection was performed by transferring the cell solution of each well to a stored second virus preload plate, centrifuging at 500 g for 1 minute, and culturing at 37° C. for 4 hours. After 4 hours of culture at 37° C., 1 ml of the cell suspension of each well was transferred to a new 12-well cell culture plate, diluted 4-fold with a fresh culture solution (GT-T551) containing IL-2 (200 IU/ml), and cultured at 37° C. in a 5% $CO_2$ incubator. The culture was performed up to day 7 from the start day of culturing the peripheral blood mononuclear cells, and thereby T cells (anti-GM2 CAR-IL-7/CCL19-expressing T cells) into which the IL-7/CCL19 expressing-anti-GM2 CAR vector had been introduced were obtained (FIG. 1B). In addition, at the same time, as a CAR-negative cell control, non-transgenic cells, which activated peripheral blood mononuclear cells obtained from the same healthy human donor in the same manner but which were not infected with retrovirus, were produced.

[Example 2] CAR Expression Measurement by Flow Cytometry (Flow Cytometric Analysis)

Analysis of an expression level of CAR that recognizes GM2 as an antigen was performed by two-color flow cytometric analysis. The produced anti-GM2 CAR-IL-7/CCL19-expressing T cells were reacted with biotinylated protein L (manufactured by GenScript), allophycocyanin (APC)-labeled streptavidin (manufactured by Affymetrix), and APC-labeled anti-CD8 monoclonal antibody (manufactured by Affymetrix), and staining was performed. EC800

(manufactured by Sony) was used for Flow cytometry and FlowJo software (manufactured by Tree Star) was used for data analysis.

Figure 2:
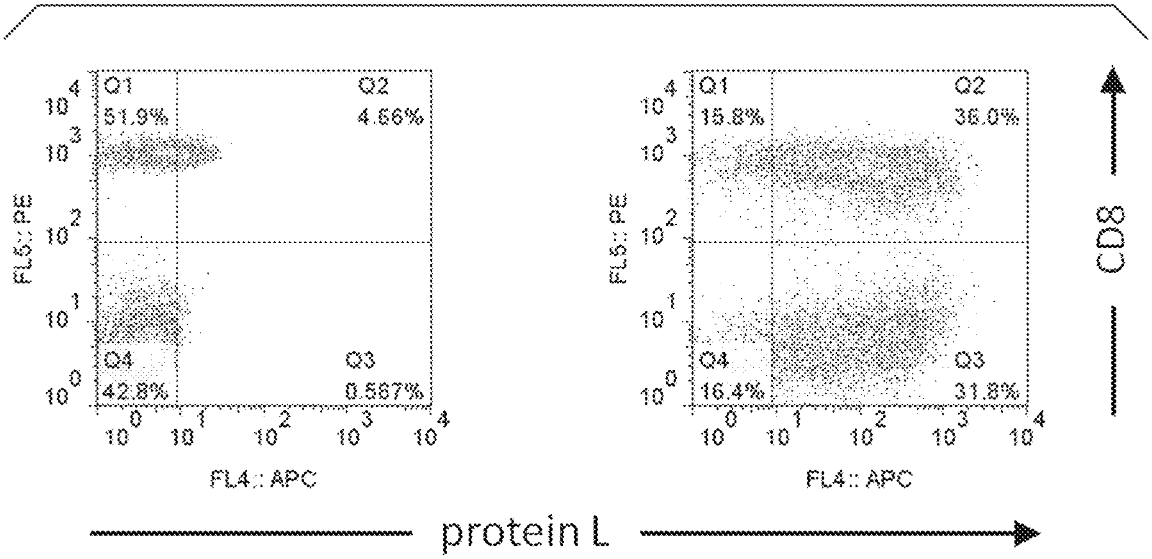
FIG. 2 shows results of checking an expression level of CAR in the anti-GM2 CAR-IL-7/CCL19-expressing T cells by flow cytometry. The left graph shows results of a non-transgenic T cell, and the right graph shows results of the anti-GM2 CAR-IL-7/CCL19-expressing T cell.

The results are shown in FIG. 2. The left graph shows results of cells into which no CAR gene was transfected and the right graph shows results of the anti-GM2 CAR-IL-7/CCL19-expressing T cells. The numerical values in the graphs represent percentages of the respective populations. As shown in FIG. 2, about 68% of CAR expression was confirmed in the anti-GM2 CAR-IL-7/CCL19-expressing T cells.

[Example 3] Production of IL-7 and CCL19

(Measurement of IL-7 and CCL19 Concentrations in Culture Supernatant of Anti-GM2 CAR-IL-7/CCL19-Expressing T Cells)

A culture supernatant of the anti-GM2 CAR-IL-7/CCL19-expressing T cells or non-transgenic cells on day 7 of the culture described above was recovered, and production of IL-7 and CCL19 by the anti-GM2 CAR-IL-7/CCL19-expressing T cells was examined using a commercially available ELISA kit (manufactured by Peprotech, and R & D systems, respectively).

[Results]

Figure 3:
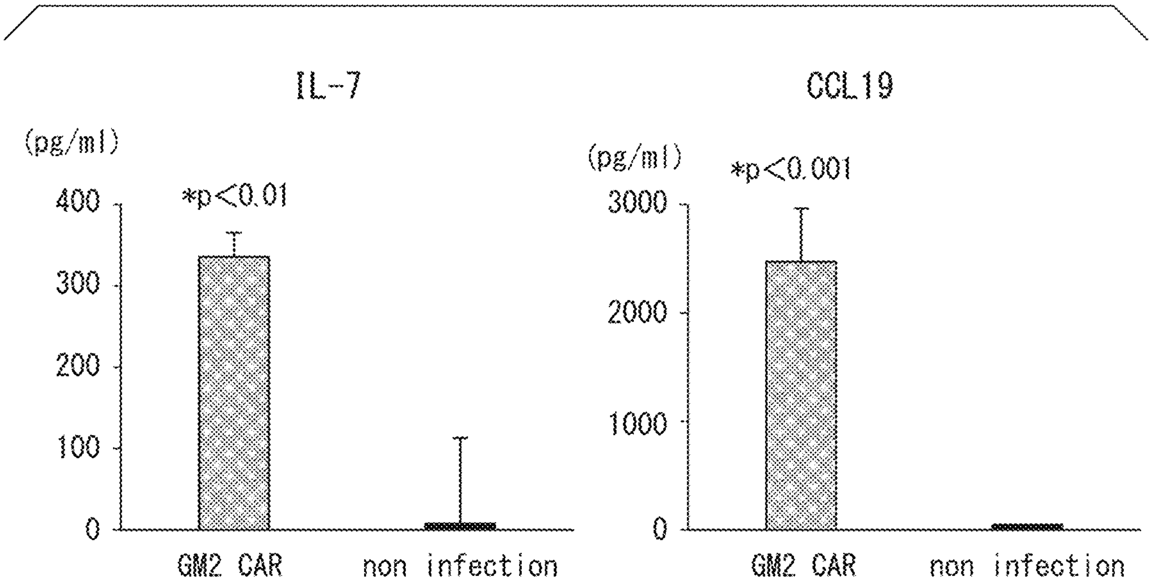
FIG. 3 shows results of measuring concentrations of IL-7 and CCL19 in a culture supernatant of an anti-GM2 CAR-expressing T cell by ELISA. In the graphs, the term "GM2 CAR" represents an anti-GM2 CAR-IL-7/CCL19-expressing T cell, and the term "non-infection" represents a non-transgenic T cell (the same applies in the subsequent drawings).

The results are shown in FIG. 3. As shown in FIG. 3, in the culture supernatant of the anti-GM2 CAR-IL-7/CCL19-expressing T cells (GM2 CAR), 300 pg/ml or more of IL-7 and 2000 pg/ml or more of CCL 19 were detected. Based on these results, it was confirmed that the anti-GM2 CAR-IL-7/CCL19-expressing T cells express IL-7 and CCL19, and the expressed IL-7 and CCL19 are extracellularly secreted. On the other hand, in the culture supernatant (non infection) of the control non-transgenic T cells, amounts of both IL-7 and CCL19 were below a detection limit (Not detected).

[Example 4] GM2 Expression in Each Tumor Cell (Flow Cytometric Analysis)

Malignant mesothelioma cell lines Y-meso8A and MSTO211H, myeloma cell line KMS-11, and colon cancer cell line SW480 were stained with an anti-GM2 antibody and a control anti-DNP antibody which were labeled with Alexa 488, and expression of GM2 in each tumor cell was measured by flow cytometric analysis. For both Alexa 488-labeled anti-GM2 antibody and Alexa 488-labeled anti-DNP antibody, the staining was performed at 10 μg/sample.

Expression of GM2 was not observed in the colon cancer cell line SW480, but expression of GM2 was confirmed in the malignant mesothelioma cell lines Y-meso8A and MSTO211H, and myeloma cell lines KMS-11 and KMS-28 PE.

[Example 5] Cytotoxicity Assays ($^{51}$Cr Release Assay 1 by Anti-GM2 CAR-IL-7/CCL19-Expressing T Cells)

Figure 4:
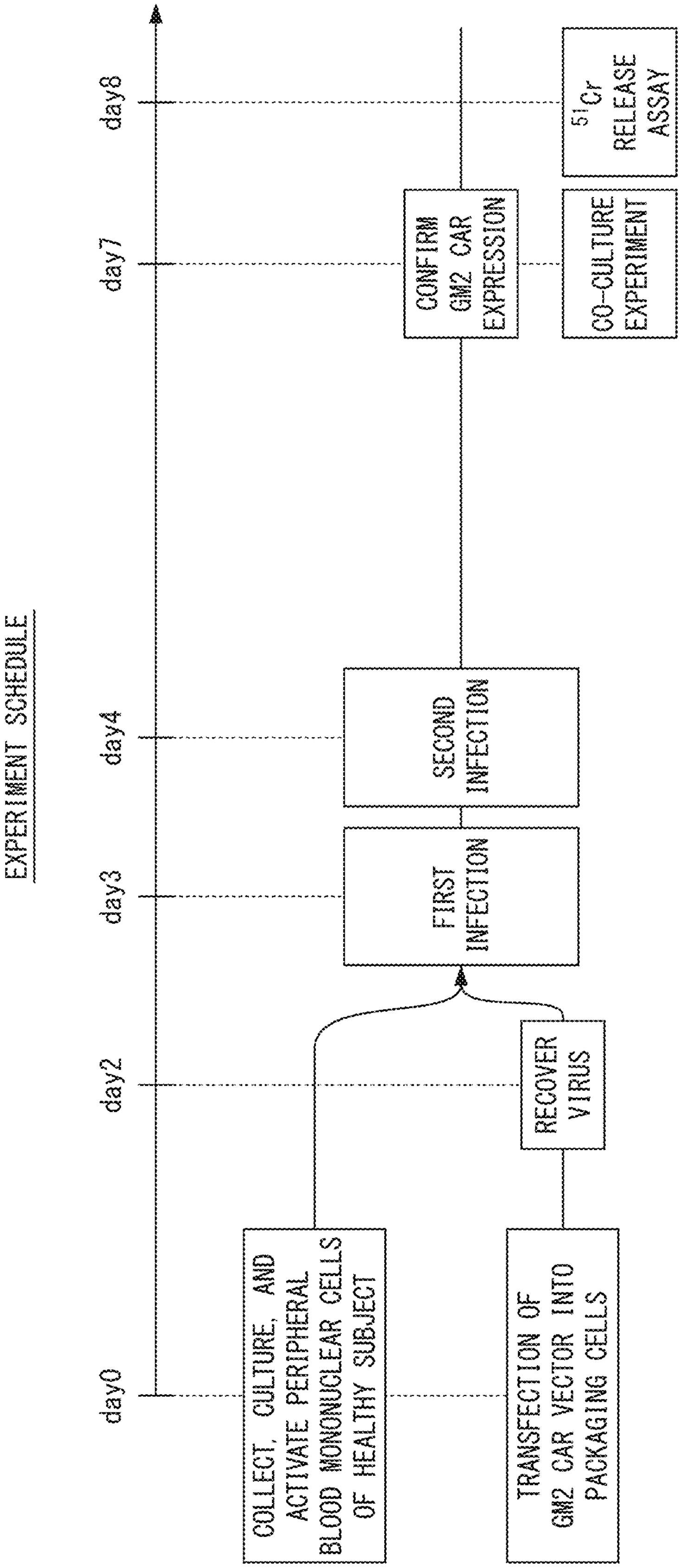
FIG. 4 shows assay schedules of a tumor cytotoxicity assay and a co-culture assay using anti-GM2 CAR-IL-7/CCL19-expressing T cells.

FIG. 4 shows test schedules of production of anti-GM2 CAR-IL-7/CCL19-expressing T cells, a tumor cytotoxicity assay, and a co-culture assay. As shown in FIG. 4, the CAR-IL-7/CCL19-expressing T cells were recovered on day 8, and cytotoxic activity of the CAR-IL-7/CCL19 expressing-T cells against tumor cells was evaluated by using a standard 4 hour $^{51}$Cr release assay.

Various tumor cells expressing human GM2 were used as target cells. The tumor cell line was cultured at 37° C. for 1 hour in the presence of 100 μCi $Na_2{}^{51}CrO_4$, and then washed 3 times, and $5\times10^3$ cells per well were added to a 96 well V-bottom plate (manufactured by Nunc®). Thereafter, as effector T cells, four types of anti-GM2 CAR-IL-7/CCL19-expressing T cells with different combinations of VH and VL, and a linker in scFv of anti-GM2 CAR, or non-transgenic T cells were added, and co-culture was performed with the target cells at 37° C. for 4 hours. An effector/target ratio (E/T ratio) was adjusted within a range of 2.5, 5, 10, 20, and 40. Maximum release and spontaneous release of the target cells were measured by culturing the target cells in a 10% TRITON™ (non-ionic surfactant/detergent) (manufactured by Sigma-Aldrich®)-containing culture solution, or in only a culture solution. $^{51}$Cr release of the supernatant was measured with a TOPCOUNT® scintillation counter (manufactured by PerkinElmer®). A percentage of cytotoxic activity was calculated by the equation: cytotoxic activity (%)=[(assay release−spontaneous release)/(maximum release−spontaneous release)]×100.

[Results]

Figure 5A:
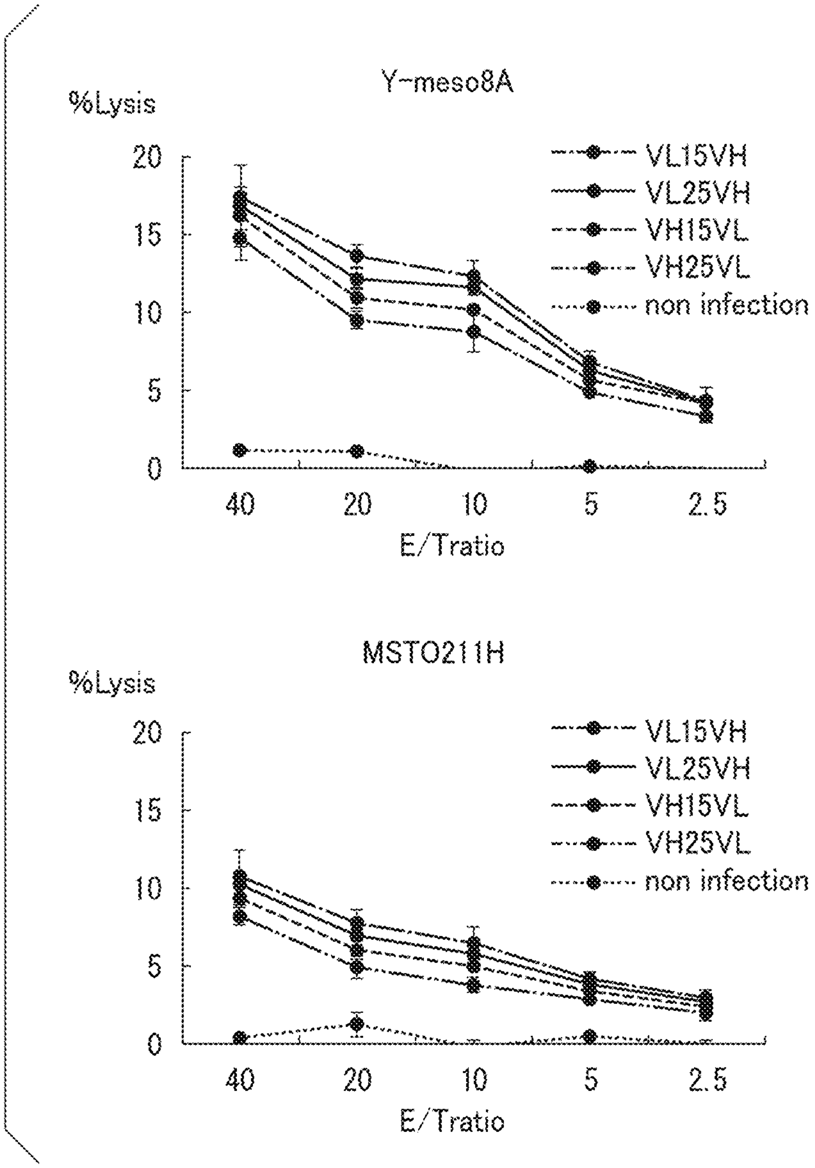
FIG. 5A shows results of a chromium release assay using four types of anti-GM2 CAR-IL-7/CCL19-expressing T cells.
Figure 5B:
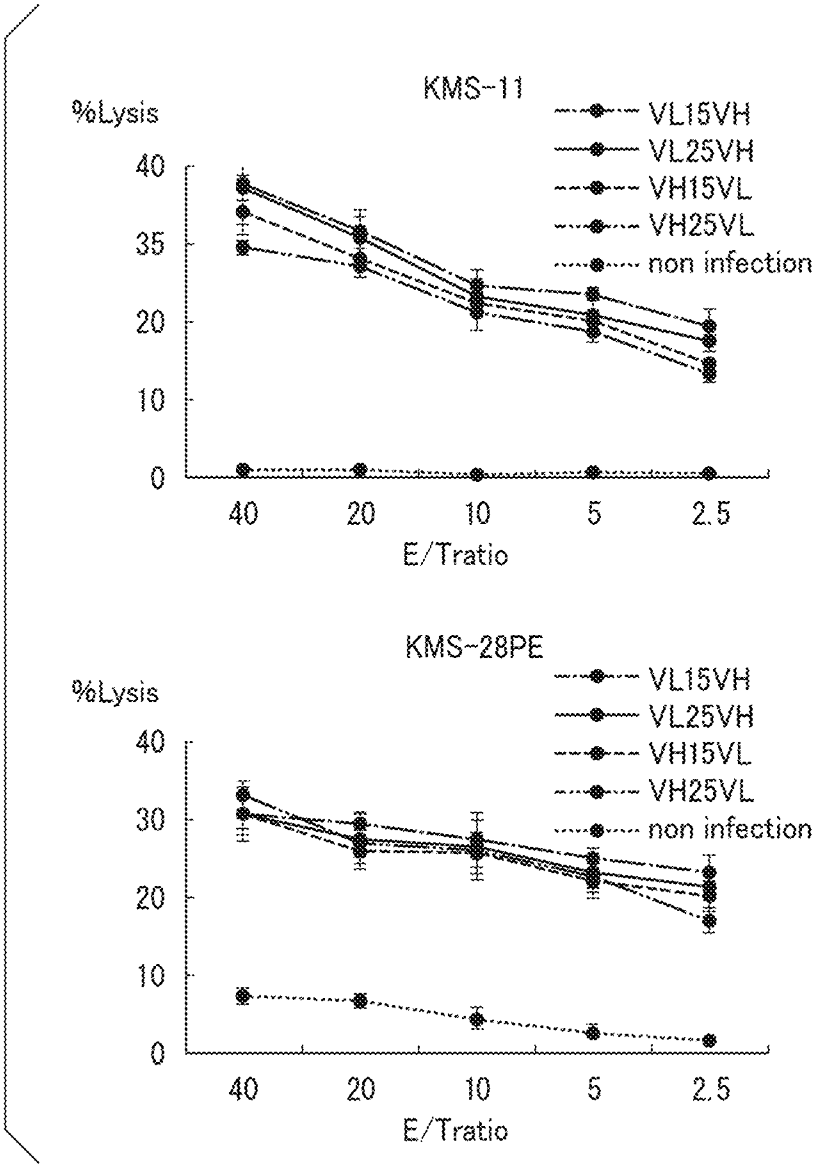
FIG. 5B shows results of a chromium release assay using four types of anti-GM2 CAR-IL-7/CCL19-expressing T cells.

The results are shown in FIGS. 5A and 5B. FIG. 5A shows the results in which malignant mesothelioma cell lines (Y-meso8A and MSTO211H) were used as target cells, and FIG. 5B shows the results in which myeloma cell lines (KMS-11 and KMS-28PE) were used as target cells. In the graphs, each of "VL15VH," "VL25VH," "VH15VL," and "VH25VL" represents the anti-GM2 CAR-IL-7/CCL19-expressing T cells including the corresponding sequences as scFv sequences of anti-GM2 CAR. As shown in FIGS. 5A and B, the anti-GM2 CAR-IL-7/CCL19-expressing T cells exhibited cytotoxicity against the tumor cell lines by any combination of VH, VL, and a linker. On the other hand, the control non-transgenic T cells (non infection) showed almost no cytotoxic activity against the tumor cell lines. In FIGS. 5A and 5B, a lateral axis of the graphs represents a ratio of effector (T cell) to target (tumor cell) in an E/T ratio, and a vertical axis represents cytotoxic activity (%).

($^{51}$Cr Release Assay 2 by Anti-GM2 CAR-IL-7/CCL19-Expressing T Cells)

To examine GM2 specificity of cytotoxic activity by the anti-GM2 CAR-IL-7/CCL19-expressing T cells, using the anti-GM2 CAR-IL-7/CCL19-expressing T cells, anti-FITC CAR-T cells that recognize FITC as a control for CAR-T cells, and non-transgenic T cells, cytotoxic activity of each cell against a GM2-positive tumor cell line and a GM2-negative tumor cell line was compared and examined. For the anti-GM2 CAR-IL-7/CCL19-expressing T cells, cells containing VL15VH as scFv sequence were used.

[Results]

Figure 6A:
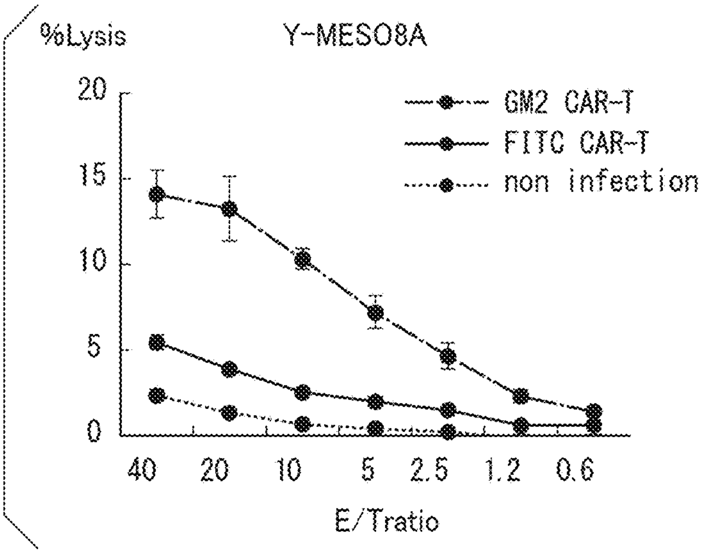
FIG. 6A shows comparison results of chromium release assays of an anti-GM2 CAR-IL-7/CCL19-expressing T cell and a control CAR-T cell.
Figure 6B:
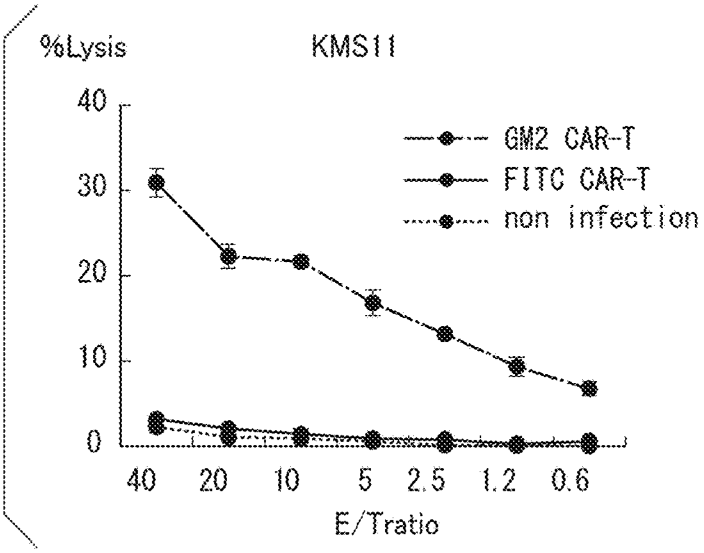
FIG. 6B shows comparison results of chromium release assays of an anti-GM2 CAR-IL-7/CCL19-expressing T cell and a control CAR-T cell.
Figure 6C:
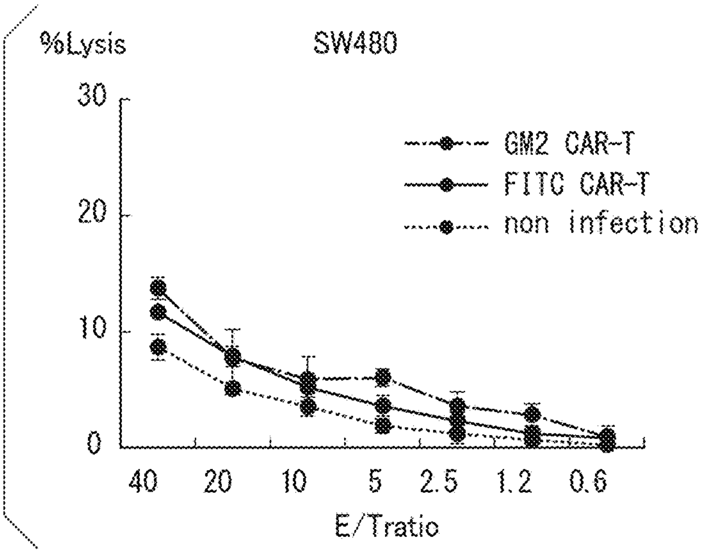
FIG. 6C shows comparison results of chromium release assays of an anti-GM2 CAR-IL-7/CCL19-expressing T cell and a control CAR-T cell.

The results are shown in FIGS. 6A to 6C. FIG. 6A shows the results in which the malignant mesothelioma cell line (Y-MESO8A) was used as a target cell, FIG. 6B shows the results in which the myeloma cell line (KMS11) was used as a target cell, and FIG. 6C shows the results in which the colon cancer cell line (SW480) was used as a target cell. As shown in FIGS. 6A to 6C, no significant cytotoxic activity of anti-FITC CAR-T cells (FITC CAR-T) was recognized against any target cells, which was almost the same level of that of the non-transgenic T cells (non infection). On the other hand, anti-GM2 CAR-IL-7/CCL19-expressing T cells (GM2 CAR-T) exhibited cytotoxicity against GM2-expressing cells (Y-MESO8A and KMS11), but did not exhibit cytotoxicity against cells not expressing GM2 (SW480). Based on the above description, it was confirmed that anti-GM2 CAR-IL-7/CCL19-expressing T cells induce cytotoxic activity specifically against GM2. In FIGS. 6A to 6C, a lateral axis of the graphs represents a ratio of effector (T cell) to target (tumor cell) in an E/T ratio, and a vertical axis represents cytotoxic activity (%).

(Co-Culture Assay)

As shown in FIG. 4, anti-GM2 CAR-IL-7/CCL19-expressing T cells were recovered on day 7, and, on a 24-well cell culture plate, were co-cultured with a GM2-positive negative tumor cell line or a GM2-negative tumor cell line in a 37° C. incubator after adjusting an effector:tumor cell ratio to 1:1 to 1:3. Cytotoxic activity was observed microscopically 2 or 3 days after the start of co-culture, and IFN-γ produced in the culture supernatant was measured using a commercially available IFN-γ ELISA kit (manufactured by BioLegend). As controls for anti-GM2 CAR-IL-7/CCL19-expressing T cells, anti-FITC CAR-expressing T cells and non-transgenic T cells were used.

[Results]

Figure 7:
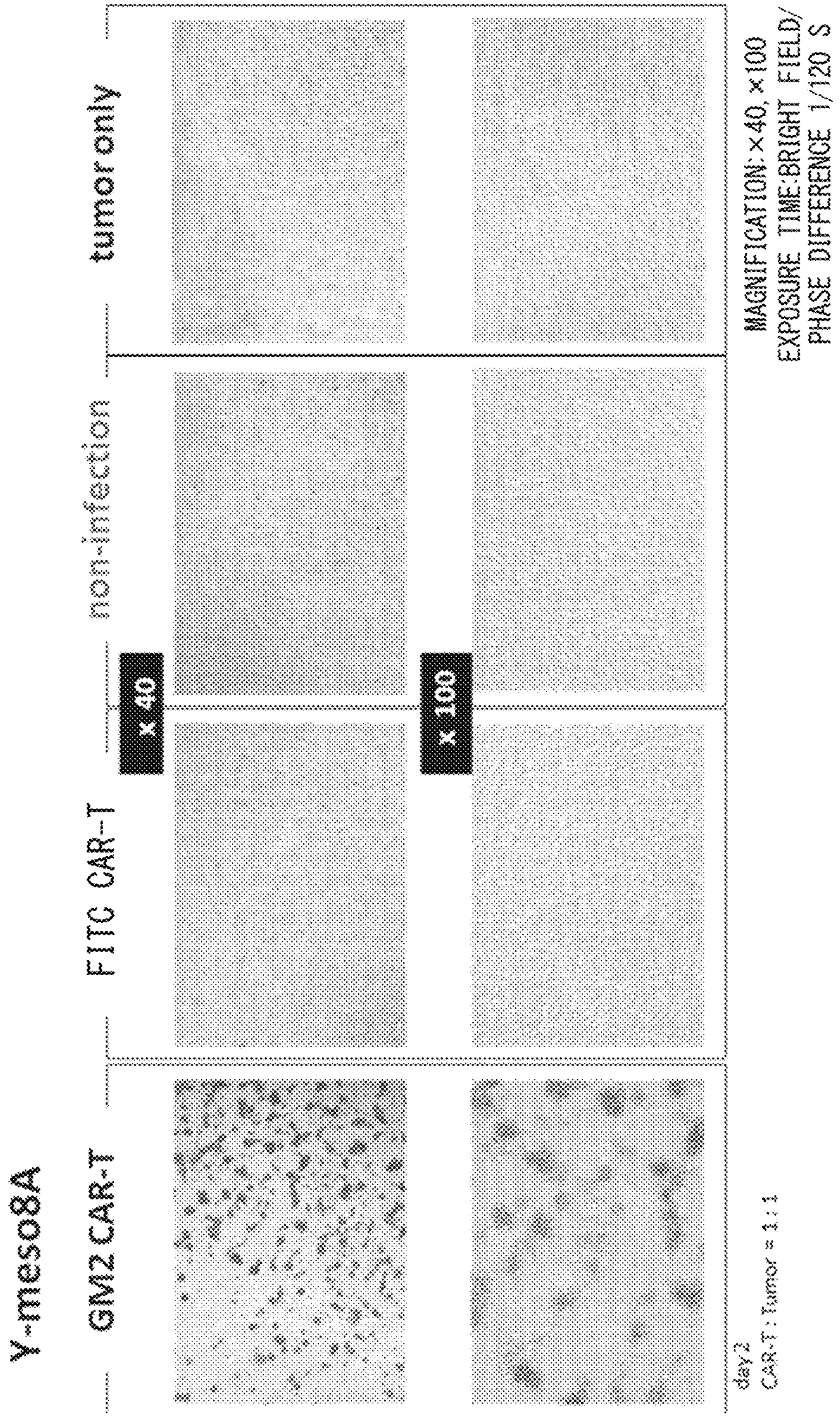
FIG. 7 shows results of a co-culture assay of a GM2-positive malignant mesothelioma cell line (Y-meso8A) with anti-GM2 CAR-IL-7/CCL19-expressing T cells or control cells. In the figure, the term "tumor only" indicates that only tumor cells are cultured (the same applies in the subsequent drawings).
Figure 8:
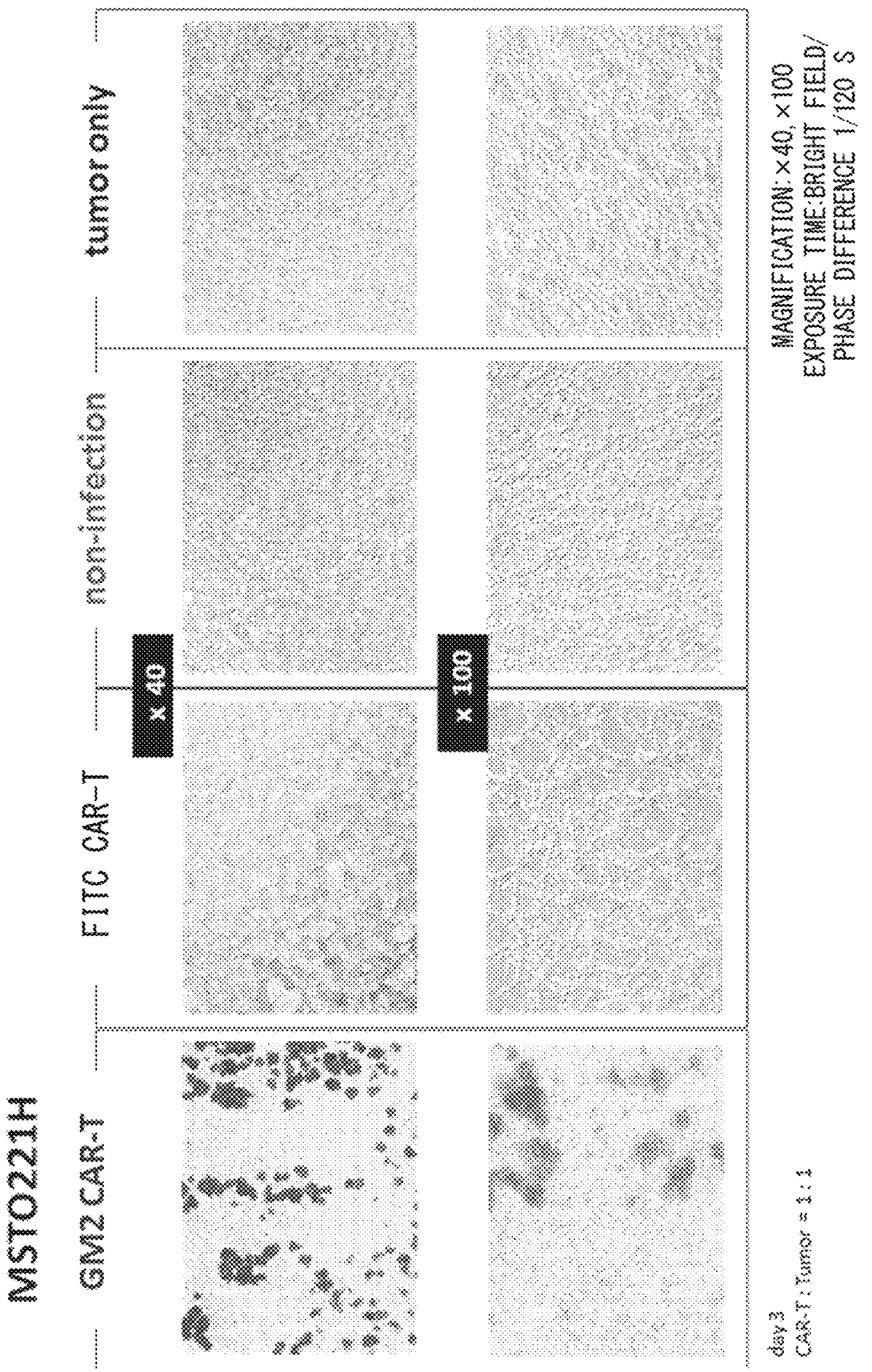
FIG. 8 shows results of a co-culture assay of a GM2-positive malignant mesothelioma cell line (MSTO221H) with anti-GM2 CAR-IL-7/CCL19-expressing T cells or control cells.
Figure 9:
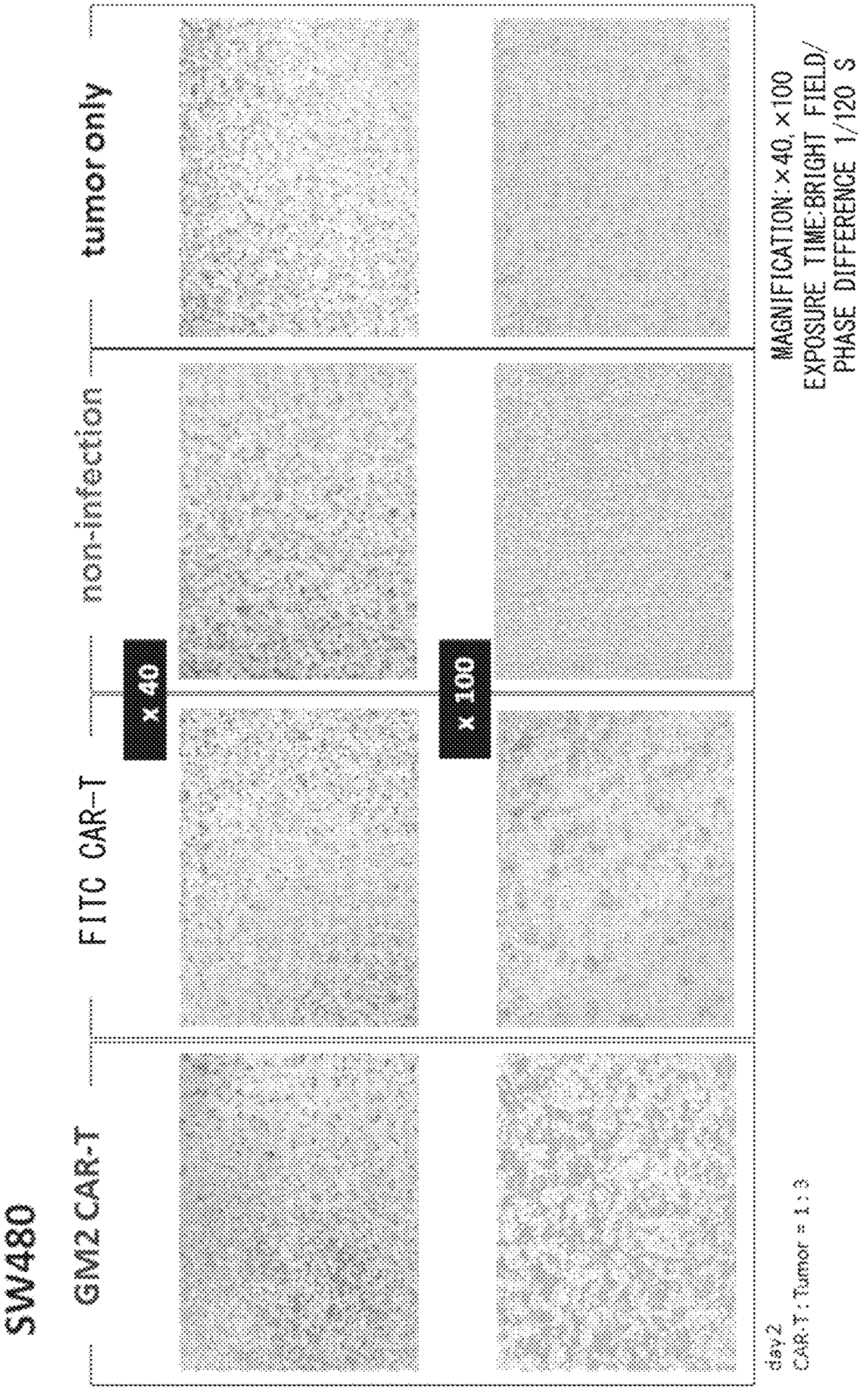
FIG. 9 shows results of a co-culture assay of a GM2-negative colon cancer cell line (SW480) with anti-GM2 CAR-IL-7/CCL19-expressing T cells or control cells.

The results are shown in FIGS. 7 to 9. FIGS. 7 and 8 show the results in which the malignant mesothelioma cell line (Y-meso8A, MSTO221H) was used as a target cell, and FIG. 9 shows the results in which the colon cancer cell line (SW480) was used as a target cell. As shown in FIGS. 7 to 9, in co-culture of the control anti-FITC CAR-expressing T cells (FITC CAR-T) or non-transgenic T cells (non-infection) with target tumor cells, all target tumor cells were observed to grow by the same level as in tumor-only wells.

On the other hand, in the anti-GM2 CAR-IL-7/CCL19-expressing T cells (GM2 CAR-T), differences in tumor growth were observed depending on the type of target tumor cell. In co-culture with GM2-negative target cells (SW 480: FIG. 9), target tumor cells grew by the same level as in tumor-only wells. On the other hand, when co-cultured with GM2-positive tumor cells (Y-meso8A: FIG. 7 and MSTO221H: FIG. 8), the number of tumor cells clearly decreased as compared to the tumor-only wells and the wells of co-culture with control cells.

Figure 10:
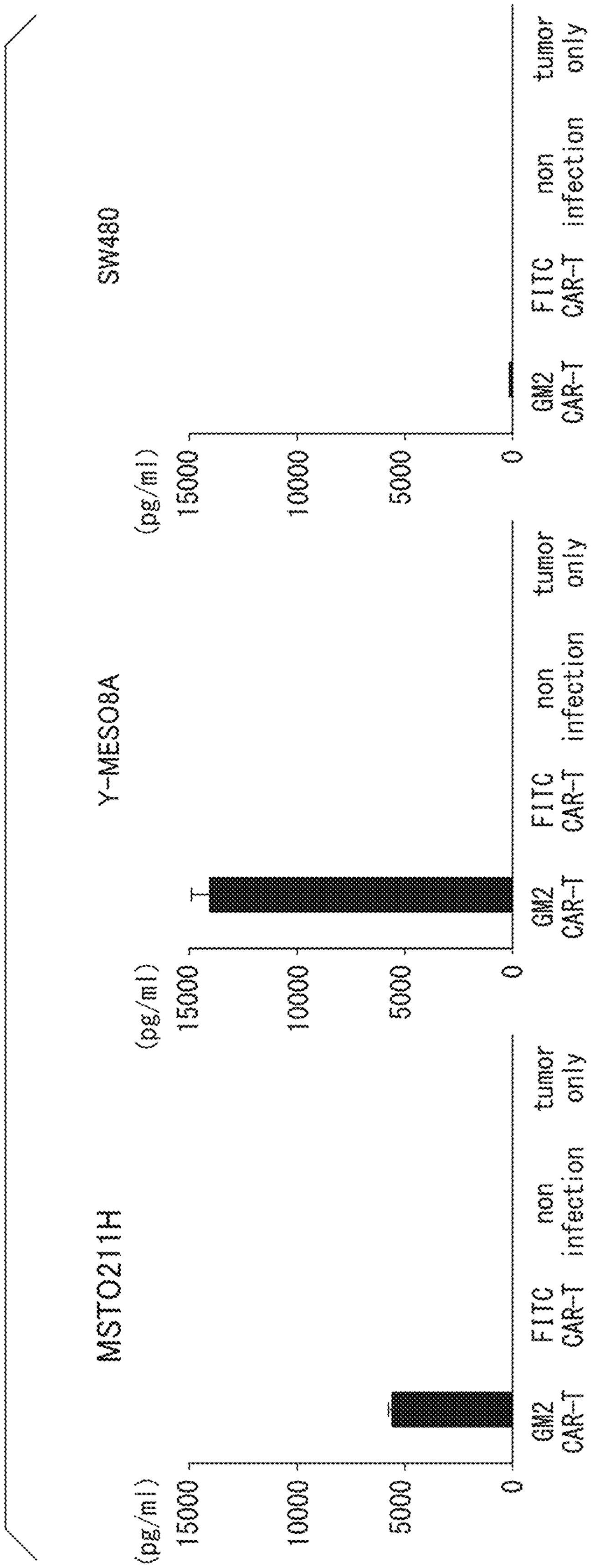
FIG. 10 shows results of measuring IFN-γ in a culture supernatant of a co-culture assay of each tumor cell line with anti-GM2 CAR-IL-7/CCL19-expressing T cells or control cells by ELISA.

Based on these results, it was confirmed that anti-GM2 CAR-IL-7/CCL19-expressing T cells damages tumor cells in an antigen-specific manner, as in the $^{51}$Cr release assay. In addition, as shown in FIG. 10, in IFN-γ ELISA using a supernatant after co-culture, production of IFN-γ was confirmed only in the co-culture supernatant of the anti-GM2 CAR-IL-7/CCL19-expressing T cells and the GM2-positive target cells (MSTO221H and Y-meso8A).

[Example 6] Therapeutic Effect in Tumor Model (Administration of Anti-GM2 CAR-IL-7/CCL19-Expressing T Cells to X-Ray Irradiated Mice)

NOD/SCID/IL2rgKO (NSG) mice, which are immunodeficient mice, were irradiated with 2 Gy X-ray, and then inoculated with $1\times1^{04}$ luciferase-expressing MSTO211H intraperitoneally or intrathoracically. After one day, $2.5\times10^7$ anti-GM2 CAR-IL-7/CCL19-expressing T cells ($1\times10^7$ cells for cells in which CAR expression was confirmed) or the same number of non-transgenic T cells as a control were administered intravenously to this intraperitoneally tumor model group (n=2) or intrathoracic tumor model group (n=3). The day of cell administration was considered day 0, and a tumor volume (=luminescence intensity due to luciferase activity) was evaluated over time using IVIS imaging system (manufactured by Perkin Elmer).

[Results]

Figure 11A:
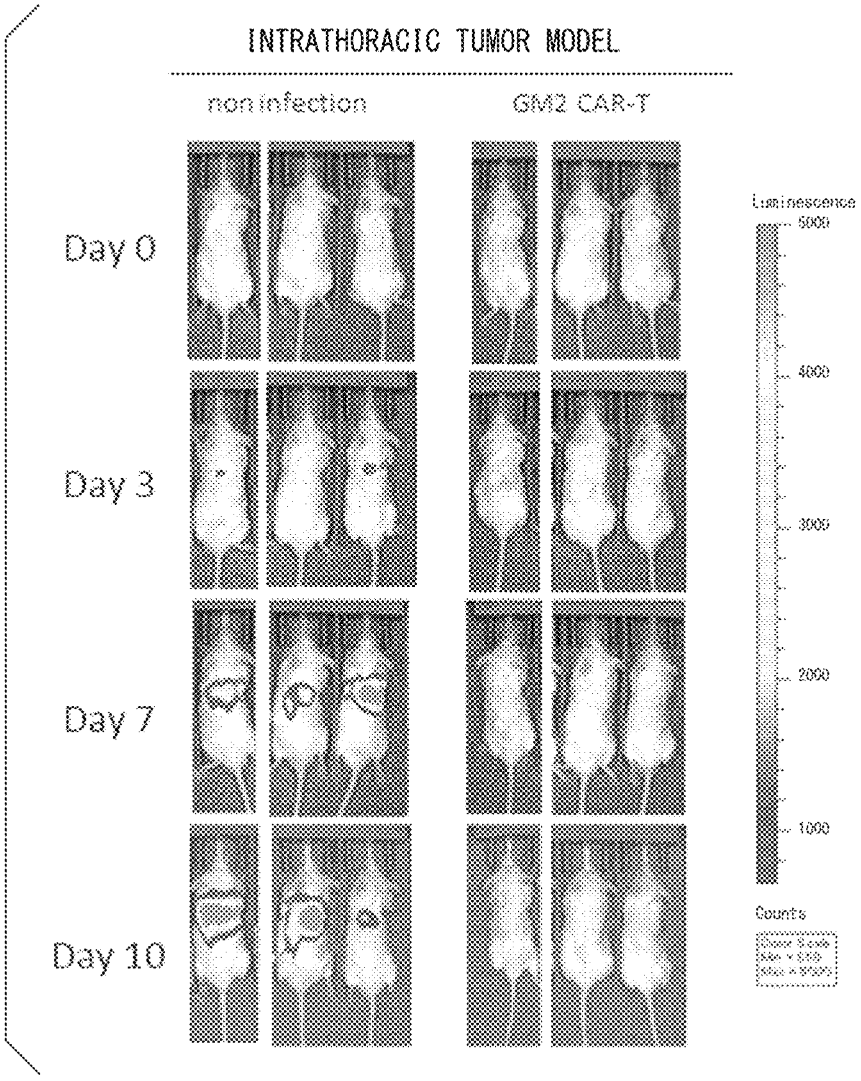
FIG. 11A shows progression of tumor growth when anti-GM2 CAR-IL-7/CCL19-expressing T cells or non-transgenic T cells are administered to immunodeficient mice to which MSTO211H expressing Luciferase has been intrathoracically administered.
Figure 11B:
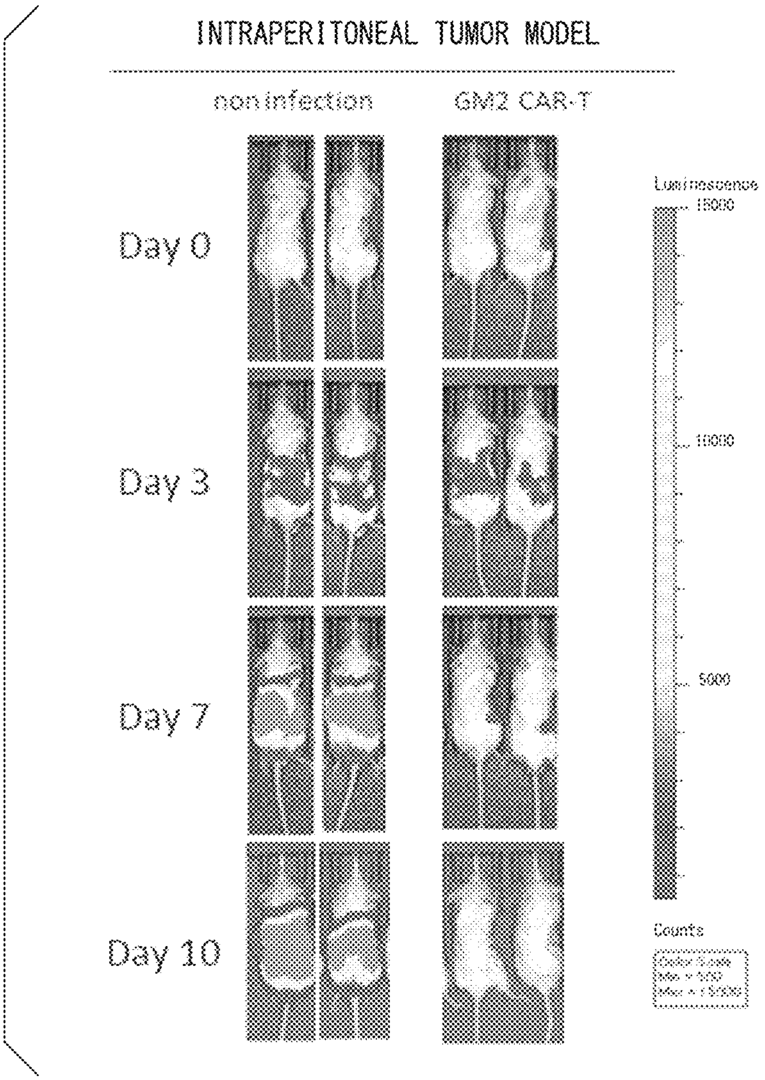
FIG. 11B shows progression of tumor growth when anti-GM2 CAR-IL-7/CCL19-expressing T cells or non-transgenic T cells are administered to immunodeficient mice to which MSTO211H expressing Luciferase has been intraperitoneally administered.

Results of changes in tumor volume of mice are shown in FIGS. 11A and 11B. FIG. 11A shows a result in an intrathoracic tumor model, and FIG. 11B shows a result in an intraperitoneal tumor model. As shown in FIG. 11A, in the intrathoracic tumor model, tumor growth was confirmed in the group (non infection) to which non-transgenic T cells were administered, but no apparent tumor growth was confirmed in the group (GM2 CAR-T) to which anti-GM2 CAR-IL-7/CCL19-expressing T cells were administered. In addition, as shown in FIG. 11B, in the intraperitoneal tumor inoculation model, tumor growth was observed up to day 3 in the group (GM2 CAR-T) to which the anti-GM2 CAR-IL-7/CCL19-expressing T cells were administered, but the tumor gradually shrank from the subsequent day. Based on these results, it became clear that the anti-GM2 CAR-IL-7/CCL19-expressing T cells exhibited excellent antitumor activity in both the intrathoracic tumor model and the intraperitoneal tumor model.

(Administration of Anti-GM2 CAR-IL-7/CCL19-Expressing T Cells to X-Ray Non-Irradiated Mice)

Next, an antitumor effect on a model in which an NSG mouse was intrathoracically inoculated with a tumor without pretreatment of X-ray irradiation was examined. The thoracic cavity was inoculated with $1\times10^4$ luciferase-expressing MSTO211H, and on the next day, $1.6\times10^7$ anti-GM2 CAR-IL-7/CCL19-expressing T cells ($1\times10^7$ cells for a case of CAR-expressing cells) or the same number of non-transgenic T cells as a control were administered intravenously (the group to which the anti-GM2 CAR-IL-7/CCL19-expressing T cells were administered: n=6, and the group to which the non-transgenic T cells were administered: n=5). The day of cell administration was considered day 0, and tumor growth was evaluated over time using the IVIS imaging system as described above.

[Results]

Figure 12:
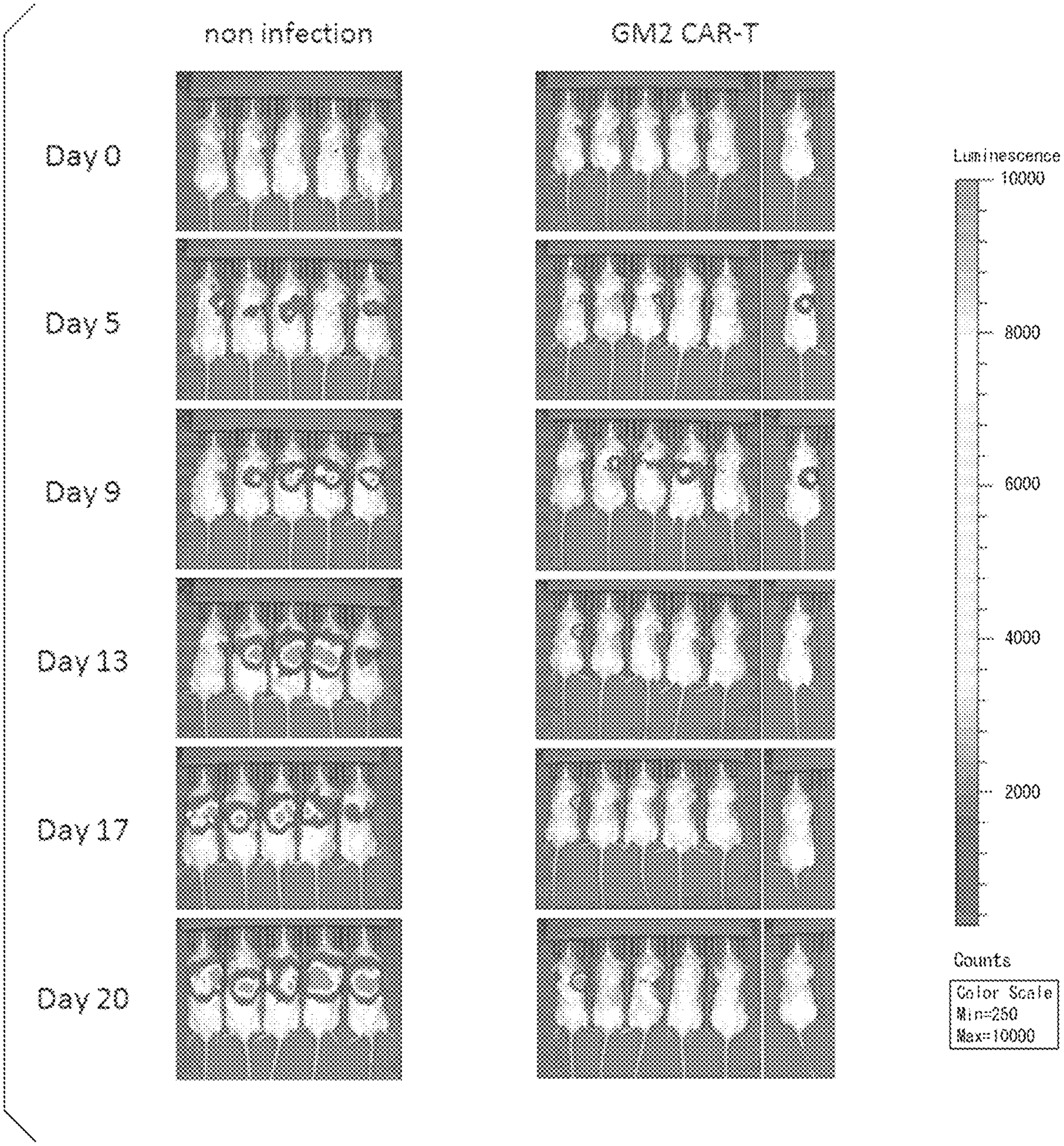
FIG. 12 shows analysis results of progression of tumor growth when anti-GM2 CAR-IL-7/CCL19-expressing T cells or non-transgenic T cells are administered to immunodeficient mice to which MSTO211H expressing Luciferase has been intrathoracically administered.

Results of changes in tumor volume of mice are shown in FIG. 12. As shown in FIG. 12, in the group (non infection) to which the non-transgenic T cells were administered, tumors gradually grew. On the other hand, in the group (GM2 CAR-T) to which the anti-GM2 CAR-IL-7/CCL19-expressing T cells were administered, tumors showed a tendency to grow until day 9, but from the subsequent day, the tumors did not grow except for one mouse and disappeared. It was confirmed that the anti-GM2 CAR-IL-7/CCL19-expressing T cells induce an excellent antitumor effect, as in the above-mentioned model subjected to X-ray irradiation pretreatment.

[Example 7] Therapeutic Effect in Tumor Model (Production of Anti-GM2 CAR-Expressing T Cells)

An anti-GM2 CAR-expressing vector was produced with the same configuration as the IL-7/CCL19 expressing-anti-GM2 CAR vector except that no IL-7-F2A-CCL19 DNA fragment was contained. This anti-GM2 CAR-expressing vector was transduced into T cells in the same manner as in Example 1, and thereby anti-GM2 CAR-expressing T cells were obtained.

(Administration of Anti-GM2 CAR-IL-7/CCL19-Expressing T Cells or Anti-GM2 CAR-Expressing T Cells to Mice)

NOD/SCID/IL2rgKO (NSG) mice, which are immunodeficient mice, were inoculated with $1\times10^4$ luciferase-expressing MSTO211H intrathoracically. After one day, $2.2\times10^6$ anti-GM2 CAR-IL-7/CCL19-expressing T cells ($1\times10^6$ cells for cells in which CAR expression was confirmed), the same number of anti-GM2 CAR-expressing T cells ($1\times10^6$ cells for cells in which CAR expression was confirmed), or the same number of non-transgenic T cells as a control were administered intravenously to this intrathoracic tumor model group. The day of cell administration was considered day 1, and a tumor volume (=luminescence intensity due to luciferase activity) was evaluated over time using IVIS imaging system (manufactured by Perkin Elmer).

[Results]

Figure 13:
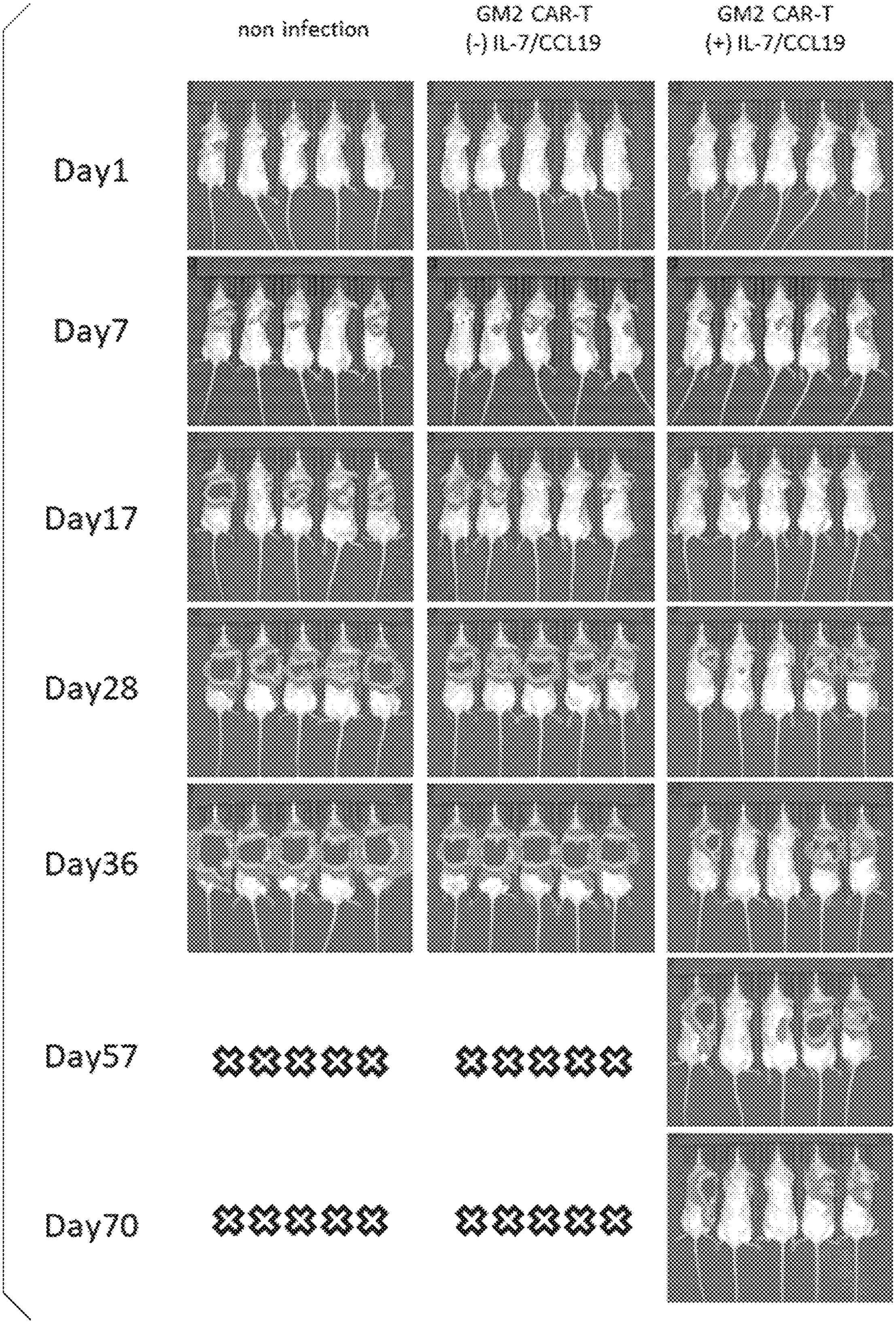
FIG. 13 shows analysis results of progression of tumor growth when anti-GM2 CAR-IL-7/CCL19-expressing T cells, anti-GM2 CAR-expressing T cells, or non-transgenic T cells are administered to immunodeficient mice to which MSTO211H expressing Luciferase has been intrathoracically administered. In the figure, "x" indicates that a mouse died.

Results of changes in tumor volume of mice are shown in FIG. 13. In FIG. 13, "x" indicates that a mouse died. As shown in FIG. 13, in the intrathoracic tumor model, tumor growth was confirmed over time in the group (non infection) to which non-transgenic T cells were administered, and no mice survived at day 57. Even in the group (GM2 CAR-T (−) IL-7/CCL19) to which the anti-GM2 CAR-expressing T cells were administered, tumors grew over time, but suppression in tumor growth was observed as compared to the group to which the non-transgenic T cells were administered. On the other hand, in the group (GM2 CAR-T (+) IL-7/CCL19) to which the anti-GM2 CAR-IL-7/CCL19-expressing T cells were administered, tumor growth was suppressed as compared to the other groups, and mice survived even after day 70.

Figure 14:
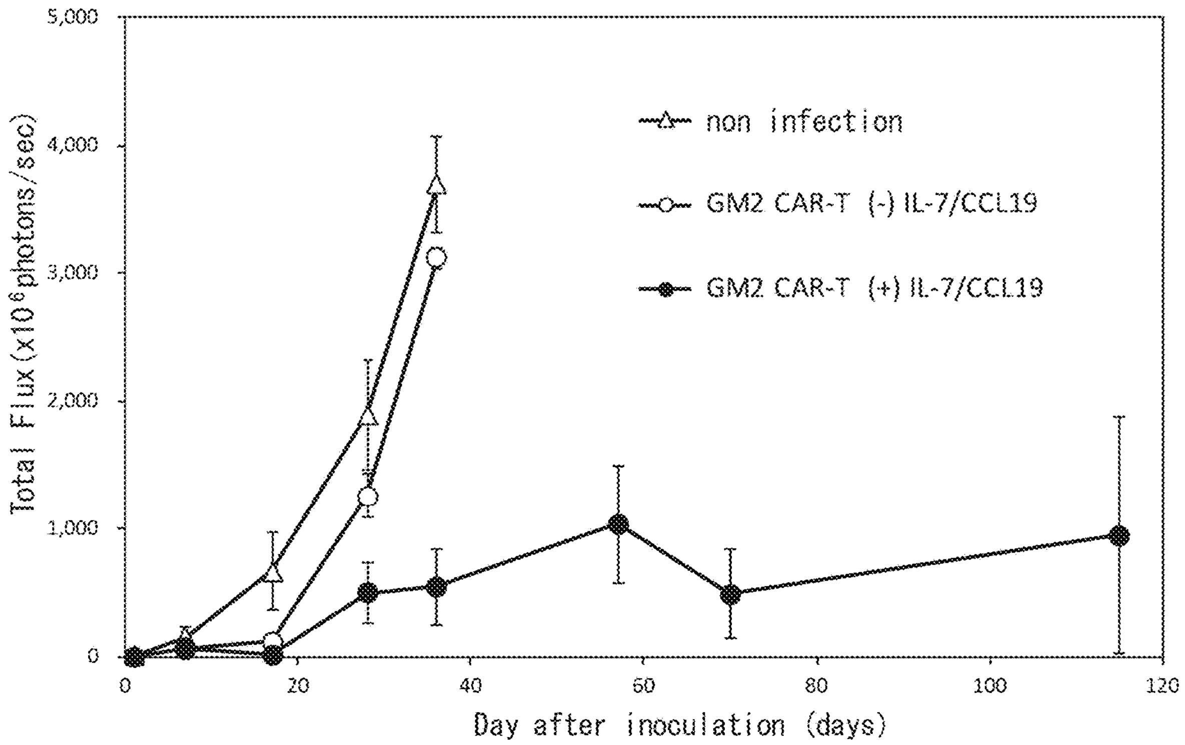
FIG. 14 shows results of analyzing effects on progression of tumor growth when anti-GM2 CAR-IL-7/CCL19-expressing T cells, anti-GM2 CAR-expressing T cells, or non-transgenic T cells are administered to immunodeficient mice to which MSTO211H expressing Luciferase has been intrathoracically administered.

FIG. 14 is a graph showing changes in luminescence intensity in FIG. 13. In the graph of FIG. 14, a lateral axis indicates the number of days elapsed since intrathoracical inoculation of tumor cells into the mouse, and a vertical axis indicates the luminescence intensity ($\times 10^6$ photons/sec) from the tumor cells. In the group (non-infection) to which the non-transgenic T cells were administered and the group (GM2 CAR-T (−) IL-7/CCL19) to which the anti-GM2 CAR-expressing T cells were administered, no mice survived at day 57, and there were no subsequent plots. In FIG. 14, it can be confirmed that tumor growth is slightly suppressed in the group (GM2 CAR-T (−) IL-7/CCL19) to which the anti-GM2 CAR-expressing T cells were administered as compared to the group (non-infection) to which the non-transgenic T cells were administered. On the other hand, in the group (GM2 CAR-T (+) IL-7/CCL19) to which the anti-GM2 CAR-IL-7/CCL19-expressing T cells were administered, tumor growth was suppressed within a substantially constant range.

Figure 15:
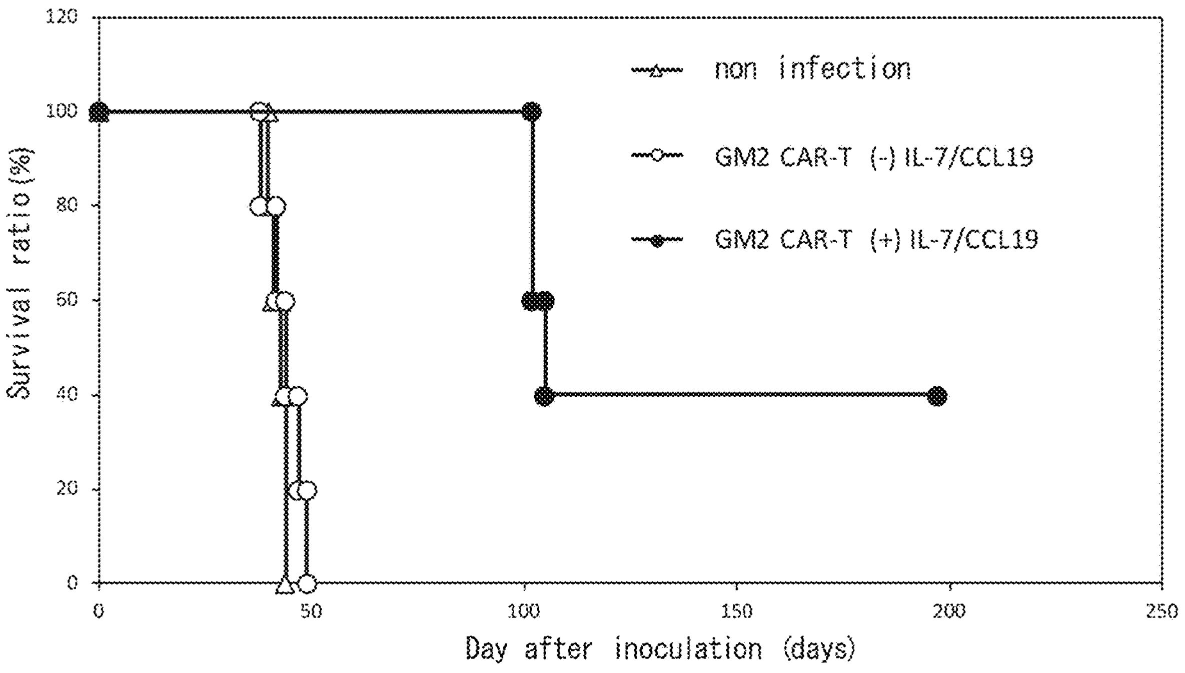
FIG. 15 shows results of analyzing effects on survival ratios of mice when anti-GM2 CAR-IL-7/CCL19-expressing T cells, anti-GM2 CAR-expressing T cells, or non-transgenic T cells are administered to immunodeficient mice to which MSTO211H expressing Luciferase has been intrathoracically administered.

In addition, FIG. 15 is a graph which shows transition in a survival ratio of mice. In the graph of FIG. 15, a lateral axis indicates the number of days elapsed since intrathoracical inoculation of tumor cells into the mouse, and a vertical axis indicates a survival ratio (%) of mice. As shown in FIG. 15, it was confirmed that, in group (GM2 CAR-T (−) IL-7/CCL19) to which the anti-GM2 CAR-expressing T cells were administered, a survival period tended to slightly extend as compared to the group (non infection) to which the non-transgenic T cells were administered. On the other hand, it was confirmed that, in the group (GM2 CAR-T (+) IL-7/CCL19) to which the anti-GM2 CAR-IL-7/CCL19-expressing T cells were administered, the survival ratio was improved (an effect of extending a survival period) as compared to the group to which the non-transgenic T cells were administered and the group to which the anti-GM2 CAR-expressing T cells were administered.

Based on these results, it became clear that the anti-GM2 CAR-IL-7/CCL19-expressing T cells had excellent antitumor activity.

INDUSTRIAL APPLICABILITY

According to the present invention, a novel CAR that targets a solid tumor antigen as a target antigen, and a CAR-T cell that is effective against solid tumors are provided. The CAR-T cells of the present invention can be applied to treatment or prevention of solid tumors expressing GM2, such as lung cancer, neuroblastoma, glioma, melanoma, malignant mesothelioma, and myeloma.

The present application is based on Japanese Patent Application No. 2017-61461 filed on Mar. 27, 2017, the content of which is incorporated in the present specification by reference in its entirety.

```
                          SEQUENCE LISTING


Sequence total quantity: 68
SEQ ID NO: 1           moltype = DNA  length = 360
FEATURE                Location/Qualifiers
misc_feature           1..360
                       note = VH region of anti-GM2 antibody for VL15VH
source                 1..360
                       mol_type = other DNA
                       organism = synthetic construct
SEQUENCE: 1
gaagtgcagc tggtgcagtc cggagccgag gtgaaaaagc ctggcgcctc cgtcaaggtg  60
agctgcaagg ccagcggcta tacattcacc gactataaca tggactgggt gaagcagagc  120
cccggccagg gactggagtg gatgggctac atctacccca ataacggcgg caccggctac  180
aaccagaagt tcaagtccaa ggtgaccatc accgtggaca ccagcaccag caccgcctac  240
atggaactgc acagcctcag aagcgaagac accgctgtgt actactgcgc cacctacggc  300
cactactacg gctacatgtt cgcctactgg ggacagggca ccctggtgac cgtcagcagc  360

SEQ ID NO: 2           moltype = AA  length = 120
FEATURE                Location/Qualifiers
REGION                 1..120
                       note = VH region of anti-GM2 antibody
source                 1..120
                       mol_type = protein
                       organism = synthetic construct
SEQUENCE: 2
EVQLVQSGAE VKKPGASVKV SCKASGYTFT DYNMDWVKQS PGQGLEWMGY IYPNNGGTGY  60
NQKFKSKVTI TVDTSTSTAY MELHSLRSED TAVYYCATYG HYYGYMFAYW GQGTLVTVSS  120

SEQ ID NO: 3           moltype = DNA  length = 318
FEATURE                Location/Qualifiers
misc_feature           1..318
                       note = VL region of anti-GM2 antibody for VL15VH
source                 1..318
                       mol_type = other DNA
```

```
                       organism = synthetic construct
SEQUENCE: 3
gacatccagc tgacccagtc ccctagcagc ctgtccgcta gccccggaga cagagtgacc  60
atcacctgtt ccgccagctc cagcgtgagc tacatgcact ggttccagca gaagcccggc  120
aaggccccca agctgtggat ctacagcacc agcaacctgg cttccggcgt gcctgccaga  180
ttttccggct ccggcagcgg cacaagctac tccctgacca tcagcagact gcagcccgaa  240
gacatcgcca cctactactg tcagcagagg agcagctacc cctacacctt cggcggcggc  300
accaaggtgg agatcaag                                                318

SEQ ID NO: 4           moltype = AA  length = 106
FEATURE                Location/Qualifiers
REGION                 1..106
                       note = VL region of anti-GM2 antibody
source                 1..106
                       mol_type = protein
                       organism = synthetic construct
SEQUENCE: 4
DIQLTQSPSS LSASPGDRVT ITCSASSSVS YMHWFQQKPG KAPKLWIYST SNLASGVPAR  60
FSGSGSGTSY SLTISRLQPE DIATYYCQQR SSYPYTFGGG TKVEIK                 106

SEQ ID NO: 5           moltype = DNA  length = 45
FEATURE                Location/Qualifiers
misc_feature           1..45
                       note = Linker 15 for VL15VH
source                 1..45
                       mol_type = other DNA
                       organism = synthetic construct
SEQUENCE: 5
ggcggcggcg gaagcggagg cggcggcagc ggcggaggcg gaagc                  45

SEQ ID NO: 6           moltype = AA  length = 15
FEATURE                Location/Qualifiers
REGION                 1..15
                       note = Linker 15
source                 1..15
                       mol_type = protein
                       organism = synthetic construct
SEQUENCE: 6
GGGGSGGGGS GGGGS                                                   15

SEQ ID NO: 7           moltype = DNA  length = 75
FEATURE                Location/Qualifiers
misc_feature           1..75
                       note = Linker 25 for VL25VH
source                 1..75
                       mol_type = other DNA
                       organism = synthetic construct
SEQUENCE: 7
agctccgctg acgacgctaa gaaggacgct gccaagaagg acgacgccaa gaaggatgac  60
gccaaaaaag acggc                                                   75

SEQ ID NO: 8           moltype = AA  length = 25
FEATURE                Location/Qualifiers
REGION                 1..25
                       note = Linker 25
source                 1..25
                       mol_type = protein
                       organism = synthetic construct
SEQUENCE: 8
SSADDAKKDA AKKDDAKKDD AKKDG                                        25

SEQ ID NO: 9           moltype = DNA  length = 723
FEATURE                Location/Qualifiers
misc_feature           1..723
                       note = anti-GM2scFv (VL15VH)
source                 1..723
                       mol_type = other DNA
                       organism = synthetic construct
SEQUENCE: 9
gacatccagc tgacccagtc ccctagcagc ctgtccgcta gccccggaga cagagtgacc  60
atcacctgtt ccgccagctc cagcgtgagc tacatgcact ggttccagca gaagcccggc  120
aaggccccca agctgtggat ctacagcacc agcaacctgg cttccggcgt gcctgccaga  180
ttttccggct ccggcagcgg cacaagctac tccctgacca tcagcagact gcagcccgaa  240
gacatcgcca cctactactg tcagcagagg agcagctacc cctacacctt cggcggcggc  300
accaaggtgg agatcaaggg cggcggcgga agcggaggcg gcggcagcgg cggaggcgga  360
agcgaagtgc agctggtgca gtccggagcc gaggtgaaaa agcctggcgc ctccgtcaag  420
gtgagctgca aggccagcgg ctatacattc accgactata acatggactg ggtgaagcag  480
agccccggcc agggactgga gtggatgggc tacatctacc ccaataacgg cggcaccggc  540
tacaaccaga agttcaagtc caaggtgacc atcaccgtgg acaccagcac cagcaccgcc  600
```

```
tacatggaac tgcacagcct cagaagcgaa gacaccgctg tgtactactg cgccacctac  660
ggccactact acggctacat gttcgcctac tggggacagg gcaccctggt gaccgtcagc  720
agc                                                                723

SEQ ID NO: 10          moltype = AA  length = 241
FEATURE                Location/Qualifiers
REGION                 1..241
                       note = anti-GM2scFv (VL15VH)
source                 1..241
                       mol_type = protein
                       organism = synthetic construct
SEQUENCE: 10
DIQLTQSPSS LSASPGDRVT ITCSASSSVS YMHWFQQKPG KAPKLWIYST SNLASGVPAR  60
FSGSGSGTSY SLTISRLQPE DIATYYCQQR SSYPYTFGGG TKVEIKGGGG SGGGGSGGGG  120
SEVQLVQSGA EVKKPGASVK VSCKASGYTF TDYNMDWVKQ SPGQGLEWMG YIYPNNGGTG  180
YNQKFKSKVT ITVDTSTSTA YMELHSLRSE DTAVYYCATY GHYYGYMFAY WGQGTLVTVS  240
S                                                                  241

SEQ ID NO: 11          moltype = DNA  length = 753
FEATURE                Location/Qualifiers
misc_feature           1..753
                       note = anti-GM2scFv (VL25VH)
source                 1..753
                       mol_type = other DNA
                       organism = synthetic construct
SEQUENCE: 11
gatatccaac tgacccagtc cccttccagc ctgagcgctt cccccggaga cagggtgaca  60
attacctgca gcgccagctc ctccgtgagc tacatgcact ggttccagca gaagcccggc  120
aaggccccca agctgtggat ctactccaca agcaacctgg cctccggcgt gcctgccaga  180
tttagcggaa gcggcagcgg cacatcctac agcctgacca tctccaggct gcagcccgag  240
gacatcgcca catactactg ccagcagagg tccagctacc cttacacatt cggaggcggc  300
accaaggtgg agatcaagag ctccgctgac gacgctaaga aggacgctgc caagaaggac  360
gacgccaaga aggatgacgc caaaaaagac ggcgaagtcc agctggtgca gagcggcgct  420
gaggtgaaga agcctggcgc cagcgtcaag gtgagctgta aggcctccgg ctacaccttc  480
accgactaca acatggattg ggtgaagcag agcccccggac agggcctgga gtggatgggc  540
tacatctacc ccaacaacgg cggcaccggc tacaaccaga aattcaagtc caaggtgacc  600
atcaccgtgg acaccagcac atccaccgcc tacatggaac tgcacagcct gaggtccgag  660
gacacagccg tgtactactg cgctacctac ggccactact acggctacat gttcgcttac  720
tggggacagg gcaccctggt gaccgtgagc tcc                               753

SEQ ID NO: 12          moltype = AA  length = 251
FEATURE                Location/Qualifiers
REGION                 1..251
                       note = anti-GM2scFv (VL25VH)
source                 1..251
                       mol_type = protein
                       organism = synthetic construct
SEQUENCE: 12
DIQLTQSPSS LSASPGDRVT ITCSASSSVS YMHWFQQKPG KAPKLWIYST SNLASGVPAR  60
FSGSGSGTSY SLTISRLQPE DIATYYCQQR SSYPYTFGGG TKVEIKSSAD DAKKDAAKKD  120
DAKKDDAKKD GEVQLVQSGA EVKKPGASVK VSCKASGYTF TDYNMDWVKQ SPGQGLEWMG  180
YIYPNNGGTG YNQKFKSKVT ITVDTSTSTA YMELHSLRSE DTAVYYCATY GHYYGYMFAY  240
WGQGTLVTVS S                                                       251

SEQ ID NO: 13          moltype = DNA  length = 723
FEATURE                Location/Qualifiers
misc_feature           1..723
                       note = anti-GM2scFv (VH15VL)
source                 1..723
                       mol_type = other DNA
                       organism = synthetic construct
SEQUENCE: 13
gaggtgcagc tggtgcagtc cggagccgag gtgaagaagc ctggcgccag cgtgaaggtg  60
agctgtaagg cctccggcta caccttcacc gactacaaca tggactgggt caagcagagc  120
cctggccagg gcctggagtg gatgggctat atctacccca acaacggcgg caccggctac  180
aaccagaagt tcaagagcaa ggtcaccatc accgtggaca cctccacctc cacagcctac  240
atggagctgc acagcctgag gagcgaggat accgccgtgt actactgcgc tacctacggc  300
cattactacg gatacatgtt cgcctactgg ggccagggaa ccctggtcac cgtgtcctcc  360
ggaggaggag gaagcggagg cggcggctcc ggcggaggcg gatccgacat ccagctgaca  420
caatccccca gcagcctgag cgctagcccc ggcgataggg tgacaattac ctgcagcgcc  480
tccagctccg tgtcctacat gcactggttt cagcaaaagc ccggcaaggc ccctaagctg  540
tggatctaca gcaccagcaa cctggccagc ggagtgcctg ccagatttag cggcagcggc  600
agcggcacca gctacagcct gaccatcagc agactgcagc ccgaggatat cgccacctac  660
tactgccagc agaggagctc ctacccctac acattcggcg gcggaaccaa ggtggagatc  720
aag                                                                723

SEQ ID NO: 14          moltype = AA  length = 241
FEATURE                Location/Qualifiers
REGION                 1..241
```

```
                        note = anti-GM2scFv (VH15VL)
source                  1..241
                        mol_type = protein
                        organism = synthetic construct
SEQUENCE: 14
EVQLVQSGAE VKKPGASVKV SCKASGYTFT DYNMDWVKQS PGQGLEWMGY IYPNNGGTGY  60
NQKFKSKVTI TVDTSTSTAY MELHSLRSED TAVYYCATYG HYYGYMFAYW GQGTLVTVSS  120
GGGGSGGGGS GGGGSDIQLT QSPSSLSASP GDRVTITCSA SSSVSYMHWF QQKPGKAPKL  180
WIYSTSNLAS GVPARFSGSG SGTSYSLTIS RLQPEDIATY YCQQRSSYPY TFGGGTKVEI  240
K                                                                  241

SEQ ID NO: 15           moltype = DNA  length = 753
FEATURE                 Location/Qualifiers
misc_feature            1..753
                        note = anti-GM2scFv (VH25VL)
source                  1..753
                        mol_type = other DNA
                        organism = synthetic construct
SEQUENCE: 15
gaagtgcagc tggtgcagtc cggagctgag gtgaagaagc ccggcgccag cgtgaaggtc  60
agctgcaaag ccagcggcta taccttcacc gactacaaca tggactgggt gaagcagagc  120
cccggccaag gcctcgagtg gatgggatac atctacccca acaacggcgg caccggctac  180
aaccagaagt tcaagagcaa ggtgaccatc accgtggaca catccacaag caccgcctat  240
atggagctcc acagcctgag gagcgaggac accgccgtgt actactgcgc cacctacggc  300
cactactacg gctatatgtt cgcctactgg ggccagggca ccctggtgac agtgtcctcc  360
tccagcgccg atgatgccaa gaaggatgcc gccaaaaagg acgacgctaa gaaggatgac  420
gccaagaagg acggcgatat ccagctgaca cagagcccta gctccctgag cgctagccct  480
ggcgacagag tgaccatcac ctgcagcgcc agctccagcg tgagctacat gcactggttc  540
cagcagaaac ccggcaaggc ccccaagctg tggatctaca gcaccagcaa tctggctagc  600
ggcgtgcctg ccaggtttag cggatccggc agcggcacct cctactccct gacaatctcc  660
agactgcagc ccgaggacat cgccacctac tactgccaac agaggtcctc ctacccctac  720
accttcggcg gcggcaccaa agtggagatc aag                               753

SEQ ID NO: 16           moltype = AA  length = 251
FEATURE                 Location/Qualifiers
REGION                  1..251
                        note = anti-GM2scFv (VH25VL)
source                  1..251
                        mol_type = protein
                        organism = synthetic construct
SEQUENCE: 16
EVQLVQSGAE VKKPGASVKV SCKASGYTFT DYNMDWVKQS PGQGLEWMGY IYPNNGGTGY  60
NQKFKSKVTI TVDTSTSTAY MELHSLRSED TAVYYCATYG HYYGYMFAYW GQGTLVTVSS  120
SSADDAKKDA AKKDDAKKDD AKKDGDIQLT QSPSSLSASP GDRVTITCSA SSSVSYMHWF  180
QQKPGKAPKL WIYSTSNLAS GVPARFSGSG SGTSYSLTIS RLQPEDIATY YCQQRSSYPY  240
TFGGGTKVEI K                                                       251

SEQ ID NO: 17           moltype = DNA  length = 165
FEATURE                 Location/Qualifiers
source                  1..165
                        mol_type = genomic DNA
                        organism = Homo sapiens
SEQUENCE: 17
ttcgtgccgg tcttcctgcc agcgaagccc accacgacgc cagcgccgcg accaccaaca  60
ccggcgccca ccatcgcgtc gcagcccctg tccctgcgcc cagaggcgtg ccggccagcg  120
gcggggggcg cagtgcacac gagggggctg gacttcgcct gtgat                  165

SEQ ID NO: 18           moltype = AA  length = 55
FEATURE                 Location/Qualifiers
source                  1..55
                        mol_type = protein
                        organism = Homo sapiens
SEQUENCE: 18
FVPVFLPAKP TTTPAPRPPT PAPTIASQPL SLRPEACRPA AGGAVHTRGL DFACD       55

SEQ ID NO: 19           moltype = DNA  length = 63
FEATURE                 Location/Qualifiers
source                  1..63
                        mol_type = genomic DNA
                        organism = Homo sapiens
SEQUENCE: 19
atctacatct gggcgccctt ggccgggact tgtggggtcc ttctcctgtc actggttatc  60
acc                                                                63

SEQ ID NO: 20           moltype = AA  length = 21
FEATURE                 Location/Qualifiers
source                  1..21
                        mol_type = protein
                        organism = Homo sapiens
```

```
SEQUENCE: 20
IYIWAPLAGT CGVLLLSLVI T                                      21

SEQ ID NO: 21          moltype = DNA  length = 21
FEATURE                Location/Qualifiers
source                 1..21
                       mol_type = genomic DNA
                       organism = Homo sapiens
SEQUENCE: 21
ctttactgca accacaggaa c                                      21

SEQ ID NO: 22          moltype = AA  length = 7
FEATURE                Location/Qualifiers
source                 1..7
                       mol_type = protein
                       organism = Homo sapiens
SEQUENCE: 22
LYCNHRN                                                      7

SEQ ID NO: 23          moltype = DNA  length = 123
FEATURE                Location/Qualifiers
source                 1..123
                       mol_type = genomic DNA
                       organism = Homo sapiens
SEQUENCE: 23
aggagtaaga ggagcaggct cctgcacagt gactacatga acatgactcc ccgccgcccc  60
gggcccaccc gcaagcatta ccagccctat gccccaccac gcgacttcgc agcctatcgc  120
tcc                                                          123

SEQ ID NO: 24          moltype = AA  length = 41
FEATURE                Location/Qualifiers
source                 1..41
                       mol_type = protein
                       organism = Homo sapiens
SEQUENCE: 24
RSKRSRLLHS DYMNMTPRRP GPTRKHYQPY APPRDFAAYR S                41

SEQ ID NO: 25          moltype = DNA  length = 138
FEATURE                Location/Qualifiers
source                 1..138
                       mol_type = genomic DNA
                       organism = Homo sapiens
SEQUENCE: 25
cgtttctctg ttgttaaacg gggcagaaag aagctcctgt atatattcaa acaaccattt  60
atgagaccag tacaaactac tcaagaggaa gatggctgta gctgccgatt tccagaagaa  120
gaagaaggag gatgtgaa                                          138

SEQ ID NO: 26          moltype = AA  length = 46
FEATURE                Location/Qualifiers
source                 1..46
                       mol_type = protein
                       organism = Homo sapiens
SEQUENCE: 26
RFSVVKRGRK KLLYIFKQPF MRPVQTTQEE DGCSCRFPEE EEGGCE           46

SEQ ID NO: 27          moltype = DNA  length = 339
FEATURE                Location/Qualifiers
source                 1..339
                       mol_type = genomic DNA
                       organism = Homo sapiens
SEQUENCE: 27
ctgagagtga agttcagcag gagcgcagac gcccccgcgt accagcaggg ccagaaccag  60
ctctataacg agctcaatct aggacgaaga gaggagtacg atgttttgga caagagacgt  120
ggccgggacc ctgagatggg gggaaagccg agaaggaaga accctcagga aggcctgtac  180
aatgaactgc agaaagataa gatggcggag gcctacagtg agattgggat gaaaggcgag  240
cgccggaggg gcaaggggca cgatggcctt taccagggtc tcagtacagc caccaaggac  300
acctacgacg cccttcacat gcaggccctg ccccctcgc                   339

SEQ ID NO: 28          moltype = AA  length = 113
FEATURE                Location/Qualifiers
source                 1..113
                       mol_type = protein
                       organism = Homo sapiens
SEQUENCE: 28
LRVKFSRSAD APAYQQGQNQ LYNELNLGRR EEYDVLDKRR GRDPEMGGKP RRKNPQEGLY  60
NELQKDKMAE AYSEIGMKGE RRRGKGHDGL YQGLSTATKD TYDALHMQAL PPR         113

SEQ ID NO: 29          moltype = DNA  length = 849
FEATURE                Location/Qualifiers
```

```
misc_feature           1..849
                       note = CD8 (hinge)_CD8 (transmembrane)_CD28
                        (signaling)_4-1BB (signaling)_CD3z (signaling)
source                 1..849
                       mol_type = other DNA
                       organism = synthetic construct
SEQUENCE: 29
ttcgtgccgg tcttcctgcc agcgaagccc accacgacgc cagcgccgcg accaccaaca  60
ccggcgccca ccatcgcgtc gcagcccctg tccctgcgcc cagaggcgtg ccggccagcg  120
gcggggggcg cagtgcacac gagggggctg gacttcgcct gtgatatcta catctgggcg  180
cccttggccg ggacttgtgg ggtccttctc ctgtcactgg ttatcaccct ttactgcaac  240
cacaggaaca ggagtaagag gagcaggctc ctgcacagtg actacatgaa catgactccc  300
cgccgccccg ggcccacccg caagcattac cagccctatg ccccaccacg cgacttcgca  360
gcctatcgct cccgtttctc tgttgttaaa cggggcagaa agaagctcct gtatatattc  420
aaacaaccat ttatgagacc agtacaaact actcaagagg aagatggctg tagctgccga  480
tttccagaag aagaagaagg aggatgtgaa ctgagagtga agttcagcag gagcgcagac  540
gcccccgcgt accagcaggg ccagaaccag ctctataacg agctcaatct aggacgaaga  600
gaggagtacg atgttttgga caagagacgt ggccgggacc ctgagatggg gggaaagccg  660
agaaggaaga accctcagga aggcctgtac aatgaactgc agaaagataa gatggcggag  720
gcctacagtg agattgggat gaaaggcgag cgccggaggg gcaaggggca cgatggcctt  780
taccagggtc tcagtacagc caccaaggac acctacgacg cccttcacat gcaggccctg  840
ccccctcgc                                                          849

SEQ ID NO: 30          moltype = AA  length = 283
FEATURE                Location/Qualifiers
REGION                 1..283
                       note = CD8 (hinge)_CD8 (transmembrane)_CD28
                        (signaling)_4-1BB (signaling)_CD3z (signaling)
source                 1..283
                       mol_type = protein
                       organism = synthetic construct
SEQUENCE: 30
FVPVFLPAKP TTTPAPRPPT PAPTIASQPL SLRPEACRPA AGGAVHTRGL DFACDIYIWA  60
PLAGTCGVLL LSLVITLYCN HRNRSKRSRL LHSDYMNMTP RRPGPTRKHY QPYAPPRDFA  120
AYRSRFSVVK RGRKKLLYIF KQPFMRPVQT TQEEDGCSCR FPEEEEGGCE LRVKFSRSAD  180
APAYQQGQNQ LYNELNLGRR EEYDVLDKRR GRDPEMGGKP RRKNPQEGLY NELQKDKMAE  240
AYSEIGMKGE RRRGKGHDGL YQGLSTATKD TYDALHMQAL PPR                    283

SEQ ID NO: 31          moltype = DNA  length = 86
FEATURE                Location/Qualifiers
misc_feature           1..86
                       note = EcoRI_F2A-NsiI
source                 1..86
                       mol_type = other DNA
                       organism = synthetic construct
SEQUENCE: 31
gaattcggaa gcggagtgaa acagactttg aattttgacc ttctcaagtt ggcgggagac  60
gtggagtcca accctggacc atgcat                                       86

SEQ ID NO: 32          moltype = AA  length = 28
FEATURE                Location/Qualifiers
REGION                 1..28
                       note = EcoRI_F2A-NsiI
source                 1..28
                       mol_type = protein
                       organism = synthetic construct
SEQUENCE: 32
EFGSGVKQTL NFDLLKLAGD VESNPGPC                                     28

SEQ ID NO: 33          moltype = DNA  length = 909
FEATURE                Location/Qualifiers
misc_feature           1..909
                       note = IL7_F2A_CCL19_SalI
source                 1..909
                       mol_type = other DNA
                       organism = synthetic construct
SEQUENCE: 33
atgttccatg tttcttttag gtatatcttt ggacttcctc ccctgatcct tgttctgttg  60
ccagtagcat catctgattg tgatattgaa ggtaaagatg gcaaacaata tgagagtgtt  120
ctaatggtca gcatcgatca attattggac agcatgaaag aaattggtag caattgcctg  180
aataatgaat ttaacttttt taaaagacat atctgtgatg ctaataagga aggtatgttt  240
ttattccgtg ctgctcgcaa gttgaggcaa tttcttaaaa tgaatagcac tggtgatttt  300
gatctccact tattaaaagt ttcagaaggc acaacaatac tgttgaactg cactggccag  360
gttaaaggaa gaaaaccagc tgccctgggt gaagcccaac caacaaagag tttggaagaa  420
aataaatctt taaaggaaca gaaaaaactg aatgacttgt gtttcctaaa gagactatta  480
caagagataa aaacttgttg gaataaaatt ttgatgggca ctaaagaaca cggaagcgga  540
gtgaaacaga ctttgaattt tgaccttctc aagttggcgg gagacgtgga gtccaaccct  600
ggacctatgg ccctgctact ggccctcagc ctgctggttc tctggacttc cccagcccca  660
actctgagtg gcaccaatga tgctgaagac tgctgcctgt ctgtgaccca gaaacccatc  720
```

-continued

```
cctgggtaca tcgtgaggaa cttccactac cttctcatca aggatggctg cagggtgcct  780
gctgtagtgt tcaccacact gaggggccgc cagctctgtg cacccccaga ccagccctgg  840
gtagaacgca tcatccagag actgcagagg acctcagcca agatgaagcg ccgcagcagt  900
taagtcgac                                                          909

SEQ ID NO: 34          moltype = AA  length = 300
FEATURE                Location/Qualifiers
REGION                 1..300
                       note = IL7_F2A_CCL19_SalI
source                 1..300
                       mol_type = protein
                       organism = synthetic construct
SEQUENCE: 34
MFHVSFRYIF GLPPLILVLL PVASSDCDIE GKDGKQYESV LMVSIDQLLD SMKEIGSNCL  60
NNEFNFFKRH ICDANKEGMF LFRAARKLRQ FLKMNSTGDF DLHLLKVSEG TTILLNCTGQ  120
VKGRKPAALG EAQPTKSLEE NKSLKEQKKL NDLCFLKRLL QEIKTCWNKI LMGTKEHGSG  180
VKQTLNFDLL KLAGDVESNP GPMALLLALS LLVLWTSPAP TLSGTNDAED CCLSVTQKPI  240
PGYIVRNFHY LLIKDGCRVP AVVFTTLRGR QLCAPPDQPW VERIIQRLQR TSAKMKRRSS  300

SEQ ID NO: 35          moltype = DNA  length = 2112
FEATURE                Location/Qualifiers
misc_feature           1..2112
                       note = IL7_F2A_CCL19_HSVtK_SalI
source                 1..2112
                       mol_type = other DNA
                       organism = synthetic construct
SEQUENCE: 35
atgttccatg tgagcttcag gtacatcttc ggactgcctc ctctcatcct ggtcctcctc  60
cccgtggcca gctccgactg tgacatcgaa ggaaaggatg gcaagcagta cgaaagcgtg  120
ctgatggtga gcatcgatca gctcctggat tccatgaagg aaatcggctc caactgcctc  180
aacaatgagt tcaacttttt taagaggcat atctgcgacg ccaacaagga gggcatgttt  240
ctgttcaggg ccgccaggaa gctgagacag ttcctcaaga tgaatagcac cggcgacttc  300
gacctccatc tgctgaaggt gtccgaggga accaccatcc tgctgaactg caccggccaa  360
gtgaagggaa gaaaacctgc tgccctgggc gaggctcagc ctaccaagag cctcgaggag  420
aacaaaagcc tgaaggagca gaagaagctg aacgacctgt gcttcctcaa gaggctcctg  480
caggagatta agacctgttg gaacaagatc ctgatgggca caaaggagca cggatccggc  540
gtgaagcaga ccctgaactt tgacctgctc aaactggccg gcgacgtcga gtccaatcct  600
ggacctatgg ctctgctgct cgccctgagc ctgctcgtcc tctggacctc ccctgctcct  660
accctgagcg gcaccaatga cgctgaagac tgctgcctgt ccgtgaccca gaagcctatc  720
cccggatata tcgtgaggaa ttttcattac ctcctgatca aggacggctg tagagtgccc  780
gccgtcgtgt tcacaacact cagaggcagg cagctgtgtg ctcccccga ccagccttgg  840
gtggagagaa tcattcagag actgcaaagg acctccgcta agatgaagag gaggtccagc  900
ggcagcggag tgaagcagac actgaatttc gacctgctca agctggccgg cgatgtggag  960
agcaaccctg gacctatggc ttcctacccc ggacatcagc acgcttccgc cttcgaccag  1020
gccgctagaa gcagaggaca ctccaataga aggacagccc tgaggcctag gagacagcag  1080
gaggccaccg aggtgaggcc cgagcagaaa atgcccaccc tgctgagagt gtatattgat  1140
ggaccccacg gcatgggaaa aaccaccaca acccagctgc tggtggctct gggaagcagg  1200
gatgatattg tgtacgtccc cgaacctatg acatattgga gggtcctcgg cgcctccgag  1260
accatcgcca acatttacac cacccagcac aggctggatc agggagagat ctccgccggc  1320
gatgctgccg tggtgatgac cagcgcccag atcactatgg gtatgcctta tgccgtgacc  1380
gacgctgtgc tggctcctca cattggcggc gaagccggat cctcccatgc tccccctcct  1440
gccctcacac tgatctttga cagacatcct atcgccgctc tgctgtgcta ccccgccgct  1500
aggtacctga tgggcagcat gacccctcag gccgtgctgg cttttgtggc cctcattccc  1560
cccacactgc ctggcacaaa tatcgtgctc ggcgccctgc ctgaggacag gcacatcgat  1620
aggctggcta agagacagag acccggagag aggctggatc tcgctatgct ggccgccatc  1680
aggagggtgt acggcctgct ggccaacacc gtgagatatc tccagtgtgg cggatcctgg  1740
agggaagact ggggccaact gagcggcaca gctgtgcctc ctcaaggcgc tgagccccag  1800
agcaacgctg gacccagacc tcacatcggc gataccctgt tcaccctgtt tagagcccct  1860
gagctcctgg cccctaacgg cgacctgtac aatgtgttcg cttgggccct ggatgtgctc  1920
gccaagagac tcaggagcat gcacgtcttc attctggact acgaccagtc ccccgctggc  1980
tgcagagatg ccctgctcca gctgacctcc ggcatggtgc agacccacgt gaccacccct  2040
ggaagcatcc ccacaatctg cgacctggcc aggacctttg ccagagaaat gggagaagcc  2100
aactgagtcg ac                                                      2112

SEQ ID NO: 36          moltype = AA  length = 701
FEATURE                Location/Qualifiers
REGION                 1..701
                       note = IL7_F2A_CCL19_HSVtK_SalI
source                 1..701
                       mol_type = protein
                       organism = synthetic construct
SEQUENCE: 36
MFHVSFRYIF GLPPLILVLL PVASSDCDIE GKDGKQYESV LMVSIDQLLD SMKEIGSNCL  60
NNEFNFFKRH ICDANKEGMF LFRAARKLRQ FLKMNSTGDF DLHLLKVSEG TTILLNCTGQ  120
VKGRKPAALG EAQPTKSLEE NKSLKEQKKL NDLCFLKRLL QEIKTCWNKI LMGTKEHGSG  180
VKQTLNFDLL KLAGDVESNP GPMALLLALS LLVLWTSPAP TLSGTNDAED CCLSVTQKPI  240
PGYIVRNFHY LLIKDGCRVP AVVFTTLRGR QLCAPPDQPW VERIIQRLQR TSAKMKRRSS  300
GSGVKQTLNF DLLKLAGDVE SNPGPMASYP GHQHASAFDQ AARSRGHSNR RTALRPRRQQ  360
EATEVRPEQK MPTLLRVYID GPHGMGKTTT TQLLVALGSR DDIVYVPEPM TYWRVLGASE  420
```

-continued

```
TIANIYTTQH RLDQGEISAG DAAVVMTSAQ ITMGMPYAVT DAVLAPHIGG EAGSSHAPPP  480
ALTLIFDRHP IAALLCYPAA RYLMGSMTPQ AVLAFVALIP PTLPGTNIVL GALPEDRHID  540
RLAKRQRPGE RLDLAMLAAI RRVYGLLANT VRYLQCGGSW REDWGQLSGT AVPPQGAEPQ  600
SNAGPRPHIG DTLFTLFRAP ELLAPNGDLY NVFAWALDVL AKRLRSMHVF ILDYDQSPAG  660
CRDALLQLTS GMVQTHVTTP GSIPTICDLA RTFAREMGEA N                      701

SEQ ID NO: 37          moltype = DNA  length = 1641
FEATURE                Location/Qualifiers
misc_feature           1..1641
                       note = anti-hCD20 CAR
source                 1..1641
                       mol_type = other DNA
                       organism = synthetic construct
SEQUENCE: 37
atggattgga cctggaggat cctgtttctg gtggctgccg ccaccggagc ccattcccag  60
atcgtgctga gccagagccc tgccattctg agcgccagcc ccggcgaaaa ggtgaccatg  120
acctgcaggg ccagcagcag cgtgtcctac atccactggt tccagcagaa gcccggctcc  180
agccccaaac cctggatcta cgccaccagc aatctggcca gcggcgtgcc tgtgagattc  240
tccggcagcg gcagcggcac aagctatagc ctgaccatct ccagagtgga ggccgaggat  300
gccgccacct actactgcca gcagtggacc agcaaccccc ccacattcgg aggcggcacc  360
aagctggaga tcaaaggcgg aggcggcagc ggcggaggcg gcagcggagg cggaggaagc  420
caagtgcagc tgcagcagcc tggagctgag ctggtgaagc ctggcgcctc cgtcaagatg  480
agctgcaagg ccagcggcta cacattcacc agctacaaca tgcactgggt gaagcagacc  540
cccggaagag gcctggagtg gatcggagcc atctaccccg gcaacggcga taccagctat  600
aaccagaagt tcaagggcaa ggccaccctc accgccgaca agagcagcag caccgcctac  660
atgcagctga gcagcctgac ctccgaggac agcgccgtgt actactgcgc caggtccacc  720
tactatggcg gcgactggta cttcaacgtg tggggcgccg gaacaaccgt gaccgtgagc  780
gccgcggccg cattcgtgcc ggtcttcctg ccagcgaagc ccaccacgac gccagcgccg  840
cgaccaccaa caccggcgcc caccatcgcg tcgcagcccc tgtccctgcg cccagaggcg  900
tgccggccag cggcgggggg cgcagtgcac acgagggggc tggacttcgc ctgtgatatc  960
tacatctggg cgcccttggc cgggacttgt ggggtccttc tcctgtcact ggttatcacc  1020
ctttactgca accacaggaa caggagtaag aggagcaggc tcctgcacag tgactacatg  1080
aacatgactc cccgccgccc cgggcccacc cgcaagcatt accagcccta tgccccacca  1140
cgcgacttcg cagcctatcg ctcccgtttc tctgttgtta aacggggcag aaagaagctc  1200
ctgtatatat tcaaacaacc atttatgaga ccagtacaaa ctactcaaga ggaagatggc  1260
tgtagctgcc gatttccaga agaagaagaa ggaggatgtg aactgagagt gaagttcagc  1320
aggagcgcag acgcccccgc gtaccagcag ggccagaacc agctctataa cgagctcaat  1380
ctaggacgaa gagaggagta cgatgttttg gacaagagac gtggccggga ccctgagatg  1440
gggggaaagc cgagaaggaa gaaccctcag gaaggcctgt acaatgaact gcagaaagat  1500
aagatggcgg aggcctacag tgagattggg atgaaaggcg agcgccggag gggcaagggg  1560
cacgatggcc tttaccaggg tctcagtaca gccaccaagg acacctacga cgcccttcac  1620
atgcaggccc tgccccctcg c                                            1641

SEQ ID NO: 38          moltype = AA  length = 547
FEATURE                Location/Qualifiers
REGION                 1..547
                       note = anti-hCD20 CAR
source                 1..547
                       mol_type = protein
                       organism = synthetic construct
SEQUENCE: 38
MDWTWRILFL VAAATGAHSQ IVLSQSPAIL SASPGEKVTM TCRASSSVSY IHWFQQKPGS  60
SPKPWIYATS NLASGVPVRF SGSGSGTSYS LTISRVEAED AATYYCQQWT SNPPTFGGGT  120
KLEIKGGGGS GGGGSGGGGS QVQLQQPGAE LVKPGASVKM SCKASGYTFT SYNMHWVKQT  180
PGRGLEWIGA IYPGNGDTSY NQKFKGKATL TADKSSSTAY MQLSSLTSED SAVYYCARST  240
YYGGDWYFNV WGAGTTVTVS AAAAFVPVFL PAKPTTTPAP RPPTPAPTIA SQPLSLRPEA  300
CRPAAGGAVH TRGLDFACDI YIWAPLAGTC GVLLLSLVIT LYCNHRNRSK RSRLLHSDYM  360
NMTPRRPGPT RKHYQPYAPP RDFAAYRSRF SVVKRGRKKL LYIFKQPFMR PVQTTQEEDG  420
CSCRFPEEEE GGCELRVKFS RSADAPAYQQ GQNQLYNELN LGRREEYDVL DKRRGRDPEM  480
GGKPRRKNPQ EGLYNELQKD KMAEAYSEIG MKGERRRGKG HDGLYQGLST ATKDTYDALH  540
MQALPPR                                                            547

SEQ ID NO: 39          moltype = DNA  length = 2625
FEATURE                Location/Qualifiers
misc_feature           1..2625
                       note = anti-GM2 CAR (VL15VH)
source                 1..2625
                       mol_type = other DNA
                       organism = synthetic construct
SEQUENCE: 39
atggattgga cctggaggat tctgttcctg gtggctgctg ccacaggcgc ccattccgac  60
atccagctga cccagtcccc tagcagcctg tccgctagcc ccggagacag agtgaccatc  120
acctgttccg ccagctccag cgtgagctac atgcactggt tccagcagaa gcccggcaag  180
gcccccaagc tgtggatcta cagcaccagc aacctggctt ccggcgtgcc tgccagattt  240
tccggctccg gcagcggcac aagctactcc ctgaccatca gcagactgca gcccgaagac  300
atcgccacct actactgtca gcagaggagc agctacccct acaccttcgg cggcggcacc  360
aaggtggaga tcaagggcgg cggcggaagc ggaggcggcg gcagcggcgg aggcggaagc  420
gaagtgcagc tggtgcagtc cggagccgag gtgaaaaagc ctggcgcctc cgtcaaggtg  480
agctgcaagg ccagcggcta tacattcacc gactataaca tggactgggt gaagcagagc  540
```

-continued

```
cccggccagg gactggagtg gatgggctac atctacccca ataacggcgg caccggctac  600
aaccagaagt tcaagtccaa ggtgaccatc accgtggaca ccagcaccag caccgcctac  660
atggaactgc acagcctcag aagcgaagac accgctgtgt actactgcgc cacctacggc  720
cactactacg gctacatgtt cgcctactgg ggacagggca ccctggtgac cgtcagcagc  780
gcggccgcat tcgtgccggt cttcctgcca gcgaagccca ccacgacgcc agcgccgcga  840
ccaccaacac cggcgcccac catcgcgtcg cagcccctgt ccctgcgccc agaggcgtgc  900
cggccagcgg cggggggcgc agtgcacacg agggggctgg acttcgcctg tgatatctac  960
atctgggcgc ccttggccgg gacttgtggg gtccttctcc tgtcactggt tatcaccctt  1020
tactgcaacc acaggaacag gagtaagagg agcaggctcc tgcacagtga ctacatgaac  1080
atgactcccc gccgccccgg gcccacccgc aagcattacc agccctatgc cccaccacgc  1140
gacttcgcag cctatcgctc ccgtttctct gttgttaaac ggggcagaaa gaagctcctg  1200
tatatattca aacaaccatt tatgagacca gtacaaacta ctcaagagga agatggctgt  1260
agctgccgat ttccagaaga agaagaagga ggatgtgaac tgagagtgaa gttcagcagg  1320
agcgcagacg cccccgcgta ccagcagggc cagaaccagc tctataacga gctcaatcta  1380
ggacgaagag aggagtacga tgttttggac aagagacgtg gccgggaccc tgagatgggg  1440
ggaaagccga gaaggaagaa ccctcaggaa ggcctgtaca atgaactgca gaaagataag  1500
atggcggagg cctacagtga gattgggatg aaaggcgagc gccggagggg caaggggcac  1560
gatggccttt accagggtct cagtacagcc accaaggaca cctacgacgc ccttcacatg  1620
caggccctgc cccctcgcga attcggaagc ggagtgaaac agactttgaa ttttgacctt  1680
ctcaagttgg cgggagacgt ggagtccaac cctggaccat gcatgttcca tgtttctttt  1740
aggtatatct ttggacttcc tcccctgatc cttgttctgt tgccagtagc atcatctgat  1800
tgtgatattg aaggtaaaga tggcaaacaa tatgagagtg ttctaatggt cagcatcgat  1860
caattattgg acagcatgaa agaaattggt agcaattgcc tgaataatga atttaacttt  1920
tttaaaagac atatctgtga tgctaataag gaaggtatgt tttattccg tgctgctcgc  1980
aagttgaggc aatttcttaa aatgaatagc actggtgatt ttgatctcca cttattaaaa  2040
gtttcagaag gcacaacaat actgttgaac tgcactggcc aggttaaagg aagaaaacca  2100
gctgccctgg gtgaagccca accaacaaag agtttggaag aaaataaatc tttaaaggaa  2160
cagaaaaaac tgaatgactt gtgtttccta aagagactat tacaagagat aaaaacttgt  2220
tggaataaaa ttttgatggg cactaaagaa cacggaagcg gagtgaaaca gactttgaat  2280
tttgaccttc tcaagttggc gggagacgtg gagtccaacc ctggacctat ggccctgcta  2340
ctggccctca gcctgctggt tctctggact tccccagccc caactctgag tggcaccaat  2400
gatgctgaag actgctgcct gtctgtgacc cagaaaccca tccctgggta catcgtgagg  2460
aacttccact accttctcat caaggatggc tgcagggtgc ctgctgtagt gttcaccaca  2520
ctgaggggcc gccagctctg tgcaccccca gaccagccct gggtagaacg catcatccag  2580
agactgcaga ggacctcagc caagatgaag cgccgcagca gttaa                  2625
```

```
SEQ ID NO: 40           moltype = AA  length = 874
FEATURE                 Location/Qualifiers
REGION                  1..874
                        note = anti-GM2 CAR (VL15VH)
source                  1..874
                        mol_type = protein
                        organism = synthetic construct
SEQUENCE: 40
MDWTWRILFL VAAATGAHSD IQLTQSPSSL SASPGDRVTI TCSASSSVSY MHWFQQKPGK  60
APKLWIYSTS NLASGVPARF SGSGSGTSYS LTISRLQPED IATYYCQQRS SYPYTFGGGT  120
KVEIKGGGGS GGGGSGGGGS EVQLVQSGAE VKKPGASVKV SCKASGYTFT DYNMDWVKQS  180
PGQGLEWMGY IYPNNGGTGY NQKFKSKVTI TVDTSTSTAY MELHSLRSED TAVYYCATYG  240
HYYGYMFAYW GQGTLVTVSS AAAFVPVFLP AKPTTTPAPR PPTPAPTIAS QPLSLRPEAC  300
RPAAGGAVHT RGLDFACDIY IWAPLAGTCG VLLLSLVITL YCNHRNRSKR SRLLHSDYMN  360
MTPRRPGPTR KHYQPYAPPR DFAAYRSRFS VVKRGRKKLL YIFKQPFMRP VQTTQEEDGC  420
SCRFPEEEEG GCELRVKFSR SADAPAYQQG QNQLYNELNL GRREEYDVLD KRRGRDPEMG  480
GKPRRKNPQE GLYNELQKDK MAEAYSEIGM KGERRRGKGH DGLYQGLSTA TKDTYDALHM  540
QALPPREFGS GVKQTLNFDL LKLAGDVESN PGPCMFHVSF RYIFGLPPLI LVLLPVASSD  600
CDIEGKDGKQ YESVLMVSID QLLDSMKEIG SNCLNNEFNF FKRHICDANK EGMFLFRAAR  660
KLRQFLKMNS TGDFDLHLLK VSEGTTILLN CTGQVKGRKP AALGEAQPTK SLEENKSLKE  720
QKKLNDLCFL KRLLQEIKTC WNKILMGTKE HGSGVKQTLN FDLLKLAGDV ESNPGPMALL  780
LALSLLVLWT SPAPTLSGTN DAEDCCLSVT QKPIPGYIVR NFHYLLIKDG CRVPAVVFTT  840
LRGRQLCAPP DQPWVERIIQ RLQRTSAKMK RRSS                              874
```

```
SEQ ID NO: 41           moltype = DNA  length = 2655
FEATURE                 Location/Qualifiers
misc_feature            1..2655
                        note = anti-GM2 CAR (VL25VH)
source                  1..2655
                        mol_type = other DNA
                        organism = synthetic construct
SEQUENCE: 41
atggactgga cctggaggat cctctttctg gtggccgccg ctaccggcgc tcacagcgat  60
atccaactga cccagtcccc ttccagcctg agcgcttccc ccggagacag ggtgacaatt  120
acctgcagcg ccagctcctc cgtgagctac atgcactggt tccagcagaa gcccggcaag  180
gcccccaagc tgtggatcta ctccacaagc aacctggcct ccggcgtgcc tgccagattt  240
agcggaagcg gcagcggcac atcctacagc ctgaccatct ccaggctgca gcccgaggac  300
atcgccacat actactgcca gcagaggtcc agctaccctt acacattcgg aggcggcacc  360
aaggtggaga tcaagagctc cgctgacgac gctaagaagg acgctgccaa gaaggacgac  420
gccaagaagg atgacgccaa aaaagacggc gaagtccagc tggtgcagag cggcgctgag  480
gtgaagaagc ctggcgccag cgtcaaggtg agctgtaagg cctccggcta caccttcacc  540
gactacaaca tggattgggt gaagcagagc cccggacagg gcctggagtg gatgggctac  600
atctacccca acaacggcgg caccggctac aaccagaaat tcaagtccaa ggtgaccatc  660
```

```
accgtggaca ccagcacatc caccgcctac atggaactgc acagcctgag gtccgaggac  720
acagccgtgt actactgcgc tacctacggc cactactacg gctacatgtt cgcttactgg  780
ggacagggca ccctggtgac cgtgagctcc gcggccgcat tcgtgccggt cttcctgcca  840
gcgaagccca ccacgacgcc agcgccgcga ccaccaacac cggcgcccac catcgcgtcg  900
cagcccctgt ccctgcgccc agaggcgtgc cggccagcgg cggggggcgc agtgcacacg  960
agggggctgg acttcgcctg tgatatctac atctgggcgc ccttggccgg gacttgtggg  1020
gtccttctcc tgtcactggt tatcaccctt tactgcaacc acaggaacag gagtaagagg  1080
agcaggctcc tgcacagtga ctacatgaac atgactcccc gccgccccgg gcccacccgc  1140
aagcattacc agccctatgc cccaccacgc gacttcgcag cctatcgctc ccgtttctct  1200
gttgttaaac ggggcagaaa gaagctcctg tatatattca aacaaccatt tatgagacca  1260
gtacaaacta ctcaagagga agatggctgt agctgccgat ttccagaaga agaagaagga  1320
ggatgtgaac tgagagtgaa gttcagcagg agcgcagacg cccccgcgta ccagcagggc  1380
cagaaccagc tctataacga gctcaatcta ggacgaagag aggagtacga tgttttggac  1440
aagagacgtg gccgggaccc tgagatgggg ggaaagccga gaaggaagaa ccctcaggaa  1500
ggcctgtaca atgaactgca gaaagataag atggcggagg cctacagtga gattgggatg  1560
aaaggcgagc gccggagggg caaggggcac gatggccttt accagggtct cagtacagcc  1620
accaaggaca cctacgacgc ccttcacatg caggccctgc cccctcgcga attcggaagc  1680
ggagtgaaac agactttgaa ttttgacctt ctcaagttgg cgggagacgt ggagtccaac  1740
cctggaccat gcatgttcca tgtttctttt aggtatatct ttggacttcc tcccctgatc  1800
cttgttctgt tgccagtagc atcatctgat tgtgatattg aaggtaaaga tggcaaacaa  1860
tatgagagtg ttctaatggt cagcatcgat caattattgg acagcatgaa agaaattggt  1920
agcaattgcc tgaataatga atttaacttt tttaaaagac atatctgtga tgctaataag  1980
gaaggtatgt ttttattccg tgctgctcgc aagttgaggc aatttcttaa aatgaatagc  2040
actggtgatt ttgatctcca cttattaaaa gtttcagaag gcacaacaat actgttgaac  2100
tgcactggcc aggttaaagg aagaaaacca gctgccctgg gtgaagccca accaacaaag  2160
agtttggaag aaaataaatc tttaaaggaa cagaaaaaac tgaatgactt gtgtttccta  2220
aagagactat tacaagagat aaaaacttgt tggaataaaa ttttgatggg cactaaagaa  2280
cacggaagcg gagtgaaaca gactttgaat tttgaccttc tcaagttggc gggagacgtg  2340
gagtccaacc ctggacctat ggccctgcta ctggccctca gcctgctggt tctctggact  2400
tccccagccc caactctgag tggcaccaat gatgctgaag actgctgcct gtctgtgacc  2460
cagaaaccca tccctgggta catcgtgagg aacttccact accttctcat caaggatggc  2520
tgcagggtgc ctgctgtagt gttcaccaca ctgaggggcc gccagctctg tgcaccccca  2580
gaccagccct gggtagaacg catcatccag agactgcaga ggacctcagc caagatgaag  2640
cgccgcagca gttaa                                                   2655

SEQ ID NO: 42          moltype = AA  length = 884
FEATURE                Location/Qualifiers
REGION                 1..884
                       note = anti-GM2 CAR (VL25VH)
source                 1..884
                       mol_type = protein
                       organism = synthetic construct
SEQUENCE: 42
MDWTWRILFL VAAATGAHSD IQLTQSPSSL SASPGDRVTI TCSASSSVSY MHWFQQKPGK  60
APKLWIYSTS NLASGVPARF SGSGSGTSYS LTISRLQPED IATYYCQQRS SYPYTFGGGT  120
KVEIKSSADD AKKDAAKKDD AKKDDAKKDG EVQLVQSGAE VKKPGASVKV SCKASGYTFT  180
DYNMDWVKQS PGQGLEWMGY IYPNNGGTGY NQKFKSKVTI TVDTSTSTAY MELHSLRSED  240
TAVYYCATYG HYYGYMFAYW GQGTLVTVSS AAAFVPVFLP AKPTTTPAPR PPTPAPTIAS  300
QPLSLRPEAC RPAAGGAVHT RGLDFACDIY IWAPLAGTCG VLLLSLVITL YCNHRNRSKR  360
SRLLHSDYMN MTPRRPGPTR KHYQPYAPPR DFAAYRSRFS VVKRGRKKLL YIFKQPFMRP  420
VQTTQEEDGC SCRFPEEEEG GCELRVKFSR SADAPAYQQG QNQLYNELNL GRREEYDVLD  480
KRRGRDPEMG GKPRRKNPQE GLYNELQKDK MAEAYSEIGM KGERRRGKGH DGLYQGLSTA  540
TKDTYDALHM QALPPREFGS GVKQTLNFDL LKLAGDVESN PGPCMFHVSF RYIFGLPPLI  600
LVLLPVASSD CDIEGKDGKQ YESVLMVSID QLLDSMKEIG SNCLNNEFNF FKRHICDANK  660
EGMFLFRAAR KLRQFLKMNS TGDFDLHLLK VSEGTTILLN CTGQVKGRKP AALGEAQPTK  720
SLEENKSLKE QKKLNDLCFL KRLLQEIKTC WNKILMGTKE HGSGVKQTLN FDLLKLAGDV  780
ESNPGPMALL LALSLLVLWT SPAPTLSGTN DAEDCCLSVT QKPIPGYIVR NFHYLLIKDG  840
CRVPAVVFTT LRGRQLCAPP DQPWVERIIQ RLQRTSAKMK RRSS                  884

SEQ ID NO: 43          moltype = DNA  length = 2625
FEATURE                Location/Qualifiers
misc_feature           1..2625
                       note = anti-GM2 CAR (VH15VL)
source                 1..2625
                       mol_type = other DNA
                       organism = synthetic construct
SEQUENCE: 43
atggactgga cctggaggat cctcttcctg gtggctgctg ccacaggcgc ccattccgag  60
gtgcagctgg tgcagtccgg agccgaggtg aagaagcctg gcgccagcgt gaaggtgagc  120
tgtaaggcct ccggctacac cttcaccgac tacaacatgg actgggtcaa gcagagccct  180
ggccagggcc tggagtggat gggctatatc taccccaaca acggcggcac cggctacaac  240
cagaagttca agagcaaggt caccatcacc gtggacacct ccacctccac agcctacatg  300
gagctgcaca gcctgaggag cgaggatacc gccgtgtact actgcgctac ctacggccat  360
tactacggat acatgttcgc ctactggggc cagggaaccc tggtcaccgt gtcctccgga  420
ggaggaggaa gcggaggcgg cggctccggc ggaggcggat ccgacatcca gctgacacaa  480
tcccccagca gcctgagcgc tagccccggc gatagggtga caattacctg cagcgcctcc  540
agctccgtgt cctacatgca ctggtttcag caaaagcccg gcaaggcccc taagctgtgg  600
atctacagca ccagcaacct ggccagcgga gtgcctgcca gatttagcgg cagcggcagc  660
ggcaccagct acagcctgac catcagcaga ctgcagcccg aggatatcgc cacctactac  720
```

```
tgccagcaga ggagctccta cccctacaca ttcggcggcg gaaccaaggt ggagatcaag  780
gcggccgcat tcgtgccggt cttcctgcca gcgaagccca ccacgacgcc agcgccgcga  840
ccaccaacac cggcgcccac catcgcgtcg cagcccctgt ccctgcgccc agaggcgtgc  900
cggccagcgg cggggggcgc agtgcacacg agggggctgg acttcgcctg tgatatctac  960
atctgggcgc ccttggccgg gacttgtggg gtccttctcc tgtcactggt tatcaccctt  1020
tactgcaacc acaggaacag gagtaagagg agcaggctcc tgcacagtga ctacatgaac  1080
atgactcccc gccgccccgg gcccacccgc aagcattacc agccctatgc ccccaccacgc  1140
gacttcgcag cctatcgctc ccgtttctct gttgttaaac ggggcagaaa gaagctcctg  1200
tatatattca aacaaccatt tatgagacca gtacaaacta ctcaagagga agatggctgt  1260
agctgccgat ttccagaaga agaagaagga ggatgtgaac tgagagtgaa gttcagcagg  1320
agcgcagacg cccccgcgta ccagcagggc cagaaccagc tctataacga gctcaatcta  1380
ggacgaagag aggagtacga tgttttggac aagagacgtg gccgggaccc tgagatgggg  1440
ggaaagccga gaaggaagaa ccctcaggaa ggcctgtaca atgaactgca gaaagataag  1500
atggcggagg cctacagtga gattgggatg aaaggcgagc gccggagggg caaggggcac  1560
gatggccttt accagggtct cagtacagcc accaaggaca cctacgacgc ccttcacatg  1620
caggccctgc cccctcgcga attcggaagc ggagtgaaac agactttgaa ttttgacctt  1680
ctcaagttgg cgggagacgt ggagtccaac cctggaccat gcatgttcca tgtttctttt  1740
aggtatatct ttggacttcc tcccctgatc cttgttctgt tgccagtagc atcatctgat  1800
tgtgatattg aaggtaaaga tggcaaacaa tatgagagtg ttctaatggt cagcatcgat  1860
caattattgg acagcatgaa agaaattggt agcaattgcc tgaataatga atttaacttt  1920
tttaaaagac atatctgtga tgctaataag gaaggtatgt ttttattccg tgctgctcgc  1980
aagttgaggc aatttcttaa aatgaatagc actggtgatt ttgatctcca cttattaaaa  2040
gtttcagaag gcacaacaat actgttgaac tgcactggcc aggttaaagg aagaaaacca  2100
gctgccctgg gtgaagccca accaacaaag agtttggaag aaaataaatc tttaaaggaa  2160
cagaaaaaac tgaatgactt gtgtttccta aagagactat tacaagagat aaaaacttgt  2220
tggaataaaa ttttgatggg cactaaagaa cacggaagcg gagtgaaaca gactttgaat  2280
tttgaccttc tcaagttggc gggagacgtg gagtccaacc ctggacctat ggccctgcta  2340
ctggccctca gcctgctggt tctctggact tccccagccc caactctgag tggcaccaat  2400
gatgctgaag actgctgcct gtctgtgacc cagaaaccca tccctgggta catcgtgagg  2460
aacttccact accttctcat caaggatggc tgcagggtgc ctgctgtagt gttcaccaca  2520
ctgaggggcc gccagctctg tgcaccccca gaccagccct gggtagaacg catcatccag  2580
agactgcaga ggacctcagc caagatgaag cgccgcagca gttaa                 2625

SEQ ID NO: 44          moltype = AA  length = 874
FEATURE                Location/Qualifiers
REGION                 1..874
                       note = anti-GM2 CAR (VH15VL)
source                 1..874
                       mol_type = protein
                       organism = synthetic construct
SEQUENCE: 44
MDWTWRILFL VAAATGAHSE VQLVQSGAEV KKPGASVKVS CKASGYTFTD YNMDWVKQSP  60
GQGLEWMGYI YPNNGGTGYN QKFKSKVTIT VDTSTSTAYM ELHSLRSEDT AVYYCATYGH  120
YYGYMFAYWG QGTLVTVSSG GGGSGGGGSG GGGSDIQLTQ SPSSLSASPG DRVTITCSAS  180
SSVSYMHWFQ QKPGKAPKLW IYSTSNLASG VPARFSGSGS GTSYSLTISR LQPEDIATYY  240
CQQRSSYPYT FGGGTKVEIK AAAFVPVFLP AKPTTTPAPR PPTPAPTIAS QPLSLRPEAC  300
RPAAGGAVHT RGLDFACDIY IWAPLAGTCG VLLLSLVITL YCNHRNRSKR SRLLHSDYMN  360
MTPRRPGPTR KHYQPYAPPR DFAAYRSRFS VVKRGRKKLL YIFKQPFMRP VQTTQEEDGC  420
SCRFPEEEEG GCELRVKFSR SADAPAYQQG QNQLYNELNL GRREEYDVLD KRRGRDPEMG  480
GKPRRKNPQE GLYNELQKDK MAEAYSEIGM KGERRRGKGH DGLYQGLSTA TKDTYDALHM  540
QALPPREFGS GVKQTLNFDL LKLAGDVESN PGPCMFHVSF RYIFGLPPLI LVLLPVASSD  600
CDIEGKDGKQ YESVLMVSID QLLDSMKEIG SNCLNNEFNF FKRHICDANK EGMFLFRAAR  660
KLRQFLKMNS TGDFDLHLLK VSEGTTILLN CTGQVKGRKP AALGEAQPTK SLEENKSLKE  720
QKKLNDLCFL KRLLQEIKTC WNKILMGTKE HGSGVKQTLN FDLLKLAGDV ESNPGPMALL  780
LALSLLVLWT SPAPTLSGTN DAEDCCLSVT QKPIPGYIVR NFHYLLIKDG CRVPAVVFTT  840
LRGRQLCAPP DQPWVERIIQ RLQRTSAKMK RRSS                             874

SEQ ID NO: 45          moltype = DNA  length = 2655
FEATURE                Location/Qualifiers
misc_feature           1..2655
                       note = anti-GM2 CAR (VH25VL)
source                 1..2655
                       mol_type = other DNA
                       organism = synthetic construct
SEQUENCE: 45
atggactgga cctggaggat cctgttcctg gtggctgctg ccaccggagc ccactccgaa  60
gtgcagctgg tgcagtccgg agctgaggtg aagaagcccg gcgccagcgt gaaggtcagc  120
tgcaaagcca gcggctatac cttcaccgac tacaacatgg actgggtgaa gcagagcccc  180
ggccaaggcc tcgagtggat gggatacatc taccccaaca acggcggcac cggctacaac  240
cagaagttca agagcaaggt gaccatcacc gtggacacat ccacaagcac cgcctatatg  300
gagctccaca gcctgaggag cgaggacacc gccgtgtact actgcgccac ctacggccac  360
tactacggct atatgttcgc ctactggggc cagggcaccc tggtgacagt gtcctcctcc  420
agcgccgatg atgccaagaa ggatgccgcc aaaaaggacg acgctaagaa ggatgacgcc  480
aagaaggacg gcgatatcca gctgacacag agccctagct ccctgagcgc tagccctggc  540
gacagagtga ccatcacctg cagcgccagc tccagcgtga gctacatgca ctggttccag  600
cagaaacccg gcaaggcccc caagctgtgg atctacagca ccagcaatct ggctagcggc  660
gtgcctgcca ggtttagcgg atccggcagc ggcacctcct actccctgac aatctccaga  720
ctgcagcccg aggacatcgc cacctactac tgccaacaga ggtcctccta cccctacacc  780
ttcggcggcg gcaccaaagt ggagatcaag gcggccgcat tcgtgccggt cttcctgcca  840
```

gcgaagccca ccacgacgcc agcgccgcga ccaccaacac cggcgcccac catcgcgtcg 900
cagcccctgt ccctgcgccc agaggcgtgc cggccagcgg cggggggcgc agtgcacacg 960
agggggctgg acttcgcctg tgatatctac atctgggcgc ccttggccgg gacttgtggg 1020
gtccttctcc tgtcactggt tatcaccctt tactgcaacc acaggaacag gagtaagagg 1080
agcaggctcc tgcacagtga ctacatgaac atgactcccc gccgccccgg gcccacccgc 1140
aagcattacc agccctatgc cccaccacgc gacttcgcag cctatcgctc ccgtttctct 1200
gttgttaaac ggggcagaaa gaagctcctg tatatattca aacaaccatt tatgagacca 1260
gtacaaacta ctcaagagga agatggctgt agctgccgat ttccagaaga agaagaagga 1320
ggatgtgaac tgagagtgaa gttcagcagg agcgcagacg cccccgcgta ccagcagggc 1380
cagaaccagc tctataacga gctcaatcta ggacgaagag aggagtacga tgttttggac 1440
aagagacgtg gccgggaccc tgagatgggg ggaaagccga gaaggaagaa ccctcaggaa 1500
ggcctgtaca atgaactgca gaaagataag atggcggagg cctacagtga gattgggatg 1560
aaaggcgagc gccggagggg caaggggcac gatggccttt accagggtct cagtacagcc 1620
accaaggaca cctacgacgc ccttcacatg caggccctgc cccctcgcga attcggaagc 1680
ggagtgaaac agactttgaa ttttgacctt ctcaagttgg cgggagacgt ggagtccaac 1740
cctggaccat gcatgttcca tgtttctttt aggtatatct ttggacttcc tcccctgatc 1800
cttgttctgt tgccagtagc atcatctgat tgtgatattg aaggtaaaga tggcaaacaa 1860
tatgagagtg ttctaatggt cagcatcgat caattattgg acagcatgaa agaaattggt 1920
agcaattgcc tgaataatga atttaacttt tttaaaagac atatctgtga tgctaataag 1980
gaaggtatgt ttttattccg tgctgctcgc aagttgaggc aatttcttaa aatgaatagc 2040
actggtgatt ttgatctcca cttattaaaa gtttcagaag gcacaacaat actgttgaac 2100
tgcactggcc aggttaaagg aagaaaacca gctgccctgg gtgaagccca accaacaaag 2160
agtttggaag aaaataaatc tttaaaggaa cagaaaaaac tgaatgactt gtgtttccta 2220
aagagactat tacaagagat aaaaacttgt tggaataaaa ttttgatggg cactaaagaa 2280
cacggaagcg gagtgaaaca gactttgaat tttgaccttc tcaagttggc gggagacgtg 2340
gagtccaacc ctggacctat ggccctgcta ctggccctca gcctgctggt tctctggact 2400
tccccagccc caactctgag tggcaccaat gatgctgaag actgctgcct gtctgtgacc 2460
cagaaaccca tccctgggta catcgtgagg aacttccact accttctcat caaggatggc 2520
tgcagggtgc ctgctgtagt gttcaccaca ctgaggggcc gccagctctg tgcaccccca 2580
gaccagccct gggtagaacg catcatccag agactgcaga ggacctcagc caagatgaag 2640
cgccgcagca gttaa 2655

SEQ ID NO: 46 moltype = AA length = 884
FEATURE Location/Qualifiers
REGION 1..884
note = anti-GM2 CAR (VH25VL)
source 1..884
mol_type = protein
organism = synthetic construct
SEQUENCE: 46
MDWTWRILFL VAAATGAHSE VQLVQSGAEV KKPGASVKVS CKASGYTFTD YNMDWVKQSP 60
GQGLEWMGYI YPNNGGTGYN QKFKSKVTIT VDTSTSTAYM ELHSLRSEDT AVYYCATYGH 120
YYGYMFAYWG QGTLVTVSSS SADDAKKDAA KKDDAKKDDA KKDGDIQLTQ SPSSLSASPG 180
DRVTITCSAS SSVSYMHWFQ QKPGKAPKLW IYSTSNLASG VPARFSGSGS GTSYSLTISR 240
LQPEDIATYY CQQRSSYPYT FGGGTKVEIK AAAFVPVFLP AKPTTTPAPR PPTPAPTIAS 300
QPLSLRPEAC RPAAGGAVHT RGLDFACDIY IWAPLAGTCG VLLLSLVITL YCNHRNRSKR 360
SRLLHSDYMN MTPRRPGPTR KHYQPYAPPR DFAAYRSRFS VVKRGRKKLL YIFKQPFMRP 420
VQTTQEEDGC SCRFPEEEEG GCELRVKFSR SADAPAYQQG QNQLYNELNL GRREEYDVLD 480
KRRGRDPEMG GKPRRKNPQE GLYNELQKDK MAEAYSEIGM KGERRRGKGH DGLYQGLSTA 540
TKDTYDALHM QALPPREFGS GVKQTLNFDL LKLAGDVESN PGPCMFHVSF RYIFGLPPLI 600
LVLLPVASSD CDIEGKDGKQ YESVLMVSID QLLDSMKEIG SNCLNNEFNF FKRHICDANK 660
EGMFLFRAAR KLRQFLKMNS TGDFDLHLLK VSEGTTILLN CTGQVKGRKP AALGEAQPTK 720
SLEENKSLKE QKKLNDLCFL KRLLQEIKTC WNKILMGTKE HGSGVKQTLN FDLLKLAGDV 780
ESNPGPMALL LALSLLVLWT SPAPTLSGTN DAEDCCLSVT QKPIPGYIVR NFHYLLIKDG 840
CRVPAVVFTT LRGRQLCAPP DQPWVERIIQ RLQRTSAKMK RRSS 884

SEQ ID NO: 47 moltype = DNA length = 3825
FEATURE Location/Qualifiers
misc_feature 1..3825
note = anti-GM2 CAR (VL15VH)_HSV tk
source 1..3825
mol_type = other DNA
organism = synthetic construct
SEQUENCE: 47
atggattgga cctggaggat tctgttcctg gtggctgctg ccacaggcgc ccattccgac 60
atccagctga cccagtcccc tagcagcctg tccgctagcc ccggagacag agtgaccatc 120
acctgttccg ccagctccag cgtgagctac atgcactggt tccagcagaa gcccggcaag 180
gcccccaagc tgtggatcta cagcaccagc aacctggctt ccggcgtgcc tgccagattt 240
tccggctccg gcagcggcac aagctactcc ctgaccatca gcagactgca gcccgaagac 300
atcgccacct actactgtca gcagaggagc agctacccct acaccttcgg cggcggcacc 360
aaggtggaga tcaagggcgg cggcggaagc ggaggcggcg gcagcggcgg aggcggaagc 420
gaagtgcagc tggtgcagtc cggagccgag gtgaaaaagc ctggcgcctc cgtcaaggtg 480
agctgcaagg ccagcggcta tacattcacc gactataaca tggactgggt gaagcagagc 540
cccggccagg gactggagtg gatgggctac atctacccca ataacggcgg caccggctac 600
aaccagaagt tcaagtccaa ggtgaccatc accgtggaca ccagcaccag caccgcctac 660
atggaactgc acagcctcag aagcgaagac accgctgtgt actactgcgc cacctacggc 720
cactactacg gctacatgtt cgcctactgg ggacagggca ccctggtgac cgtcagcagc 780
gcggccgcat tcgtgccggt cttcctgcca gcgaagccca ccacgacgcc agcgccgcga 840
ccaccaacac cggcgcccac catcgcgtcg cagcccctgt ccctgcgccc agaggcgtgc 900

```
cggccagcgg cggggggcgc agtgcacacg agggggctgg acttcgcctg tgatatctac  960
atctgggcgc ccttggccgg gacttgtggg gtccttctcc tgtcactggt tatcaccctt  1020
tactgcaacc acaggaacag gagtaagagg agcaggctcc tgcacagtga ctacatgaac  1080
atgactcccc gccgccccgg gcccacccgc aagcattacc agccctatgc ccccaccacgc  1140
gacttcgcag cctatcgctc ccgtttctct gttgttaaac ggggcagaaa gaagctcctg  1200
tatatattca aacaaccatt tatgagacca gtacaaacta ctcaagagga agatggctgt  1260
agctgccgat ttccagaaga agaagaagga ggatgtgaac tgagagtgaa gttcagcagg  1320
agcgcagacg cccccgcgta ccagcagggc cagaaccagc tctataacga gctcaatcta  1380
ggacgaagag aggagtacga tgttttggac aagagacgtg gccgggaccc tgagatgggg  1440
ggaaagccga gaaggaagaa ccctcaggaa ggcctgtaca atgaactgca gaaagataag  1500
atggcggagg cctacagtga gattgggatg aaaggcgagc gccggagggg caaggggcac  1560
gatggccttt accagggtct cagtacagcc accaaggaca cctacgacgc ccttcacatg  1620
caggccctgc cccctcgcga attcggaagc ggagtgaaac agactttgaa ttttgacctt  1680
ctcaagttgg cgggagacgt ggagtccaac cctggaccat gcatgttcca tgtgagcttc  1740
aggtacatct tcggactgcc tcctctcatc ctggtcctcc tccccgtggc cagctccgac  1800
tgtgacatcg aaggaaagga tggcaagcag tacgaaagcg tgctgatggt gagcatcgat  1860
cagctcctgg attccatgaa ggaaatcggc tccaactgcc tcaacaatga gttcaacttt  1920
tttaagaggc atatctgcga cgccaacaag gagggcatgt ttctgttcag ggccgccagg  1980
aagctgagac agttcctcaa gatgaatagc accggcgact tcgacctcca tctgctgaag  2040
gtgtccgagg gaaccaccat cctgctgaac tgcaccggcc aagtgaaggg aagaaaacct  2100
gctgccctgg gcgaggctca gcctaccaag agcctcgagg agaacaaaag cctgaaggag  2160
cagaagaagc tgaacgacct gtgcttcctc aagaggctcc tgcaggagat taagacctgt  2220
tggaacaaga tcctgatggg cacaaaggag cacggatccg gcgtgaagca gaccctgaac  2280
tttgacctgc tcaaactggc cggcgacgtc gagtccaatc ctggacctat ggctctgctg  2340
ctcgccctga gcctgctcgt cctctggacc tcccctgctc ctaccctgag cggcaccaat  2400
gacgctgaag actgctgcct gtccgtgacc cagaagccta tccccggata tatcgtgagg  2460
aattttcatt acctcctgat caaggacggc tgtagagtgc ccgccgtcgt gttcacaaca  2520
ctcagaggca ggcagctgtg tgctccccc gaccagcctt gggtggagag aatcattcag  2580
agactgcaaa ggacctccgc taagatgaag aggaggtcca gcggcagcgg agtgaagcag  2640
acactgaatt tcgacctgct caagctggcc ggcgatgtgg agagcaaccc tggacctatg  2700
gcttcctacc ccggacatca gcacgcttcc gccttcgacc aggccgctag aagcagagga  2760
cactccaata gaaggacagc cctgaggcct aggagacagc aggaggccac cgaggtgagg  2820
cccgagcaga aaatgcccac cctgctgaga gtgtatattg atggacccca cggcatggga  2880
aaaaccacca caacccagct gctggtggct ctgggaagca gggatgatat tgtgtacgtc  2940
cccgaaccta tgacatattg gagggtcctc ggcgcctccg agaccatcgc caacatttac  3000
accacccagc acaggctgga tcagggagag atctccgccg gcgatgctgc cgtggtgatg  3060
accagcgccc agatcactat gggtatgcct tatgccgtga ccgacgctgt gctggctcct  3120
cacattggcg gcgaagccgg atcctcccat gctcccctc ctgccctcac actgatcttt  3180
gacagacatc ctatcgccgc tctgctgtgc taccccgccg ctaggtacct gatgggcagc  3240
atgacccctc aggccgtgct ggcttttgtg gccctcattc cccccacact gcctggcaca  3300
aatatcgtgc tcggcgccct gcctgaggac aggcacatcg ataggctggc taagagacag  3360
agacccggag agaggctgga tctcgctatg ctggccgcca tcaggagggt gtacggcctg  3420
ctggccaaca ccgtgagata tctccagtgt ggcggatcct ggagggaaga ctggggccaa  3480
ctgagcggca cagctgtgcc tcctcaaggc gctgagcccc agagcaacgc tggacccaga  3540
cctcacatcg gcgataccct gttcaccctg tttagagccc ctgagctcct ggcccctaac  3600
ggcgacctgt acaatgtgtt cgcttgggcc ctggatgtgc tcgccaagag actcaggagc  3660
atgcacgtct tcattctgga ctacgaccag tcccccgctg gctgcagaga tgccctgctc  3720
cagctgacct ccggcatggt gcagacccac gtgaccaccc ctggaagcat ccccacaatc  3780
tgcgacctgg ccaggacctt tgccagagaa atgggagaag ccaac                  3825

SEQ ID NO: 48           moltype = AA  length = 1275
FEATURE                 Location/Qualifiers
REGION                  1..1275
                        note = anti-GM2 CAR (VL15VH)_HSV tk
source                  1..1275
                        mol_type = protein
                        organism = synthetic construct
SEQUENCE: 48
MDWTWRILFL VAAATGAHSD IQLTQSPSSL SASPGDRVTI TCSASSSVSY MHWFQQKPGK  60
APKLWIYSTS NLASGVPARF SGSGSGTSYS LTISRLQPED IATYYCQQRS SYPYTFGGGT  120
KVEIKGGGGS GGGGSGGGGS EVQLVQSGAE VKKPGASVKV SCKASGYTFT DYNMDWVKQS  180
PGQGLEWMGY IYPNNGGTGY NQKFKSKVTI TVDTSTSTAY MELHSLRSED TAVYYCATYG  240
HYYGYMFAYW GQGTLVTVSS AAAFVPVFLP AKPTTTPAPR PPTPAPTIAS QPLSLRPEAC  300
RPAAGGAVHT RGLDFACDIY IWAPLAGTCG VLLLSLVITL YCNHRNRSKR SRLLHSDYMN  360
MTPRRPGPTR KHYQPYAPPR DFAAYRSRFS VVKRGRKKLL YIFKQPFMRP VQTTQEEDGC  420
SCRFPEEEEG GCELRVKFSR SADAPAYQQG QNQLYNELNL GRREEYDVLD KRRGRDPEMG  480
GKPRRKNPQE GLYNELQKDK MAEAYSEIGM KGERRRGKGH DGLYQGLSTA TKDTYDALHM  540
QALPPREFGS GVKQTLNFDL LKLAGDVESN PGPCMFHVSF RYIFGLPPLI LVLLPVASSD  600
CDIEGKDGKQ YESVLMVSID QLLDSMKEIG SNCLNNEFNF FKRHICDANK EGMFLFRAAR  660
KLRQFLKMNS TGDFDLHLLK VSEGTTILLN CTGQVKGRKP AALGEAQPTK SLEENKSLKE  720
QKKLNDLCFL KRLLQEIKTC WNKILMGTKE HGSGVKQTLN FDLLKLAGDV ESNPGPMALL  780
LALSLLVLWT SPAPTLSGTN DAEDCCLSVT QKPIPGYIVR NFHYLLIKDG CRVPAVVFTT  840
LRGRQLCAPP DQPWVERIIQ RLQRTSAKMK RRSSGSGVKQ TLNFDLLKLA GDVESNPGPM  900
ASYPGHQHAS AFDQAARSRG HSNRRTALRP RRQQEATEVR PEQKMPTLLR VYIDGPHGMG  960
KTTTTQLLVA LGSRDDIVYV PEPMTYWRVL GASETIANIY TTQHRLDQGE ISAGDAAVVM  1020
TSAQITMGMP YAVTDAVLAP HIGGEAGSSH APPPALTLIF DRHPIAALLC YPAARYLMGS  1080
MTPQAVLAFV ALIPPTLPGT NIVLGALPED RHIDRLAKRQ RPGERLDLAM LAAIRRVYGL  1140
LANTVRYLQC GGSWREDWGQ LSGTAVPPQG AEPQSNAGPR PHIGDTLFTL FRAPELLAPN  1200
GDLYNVFAWA LDVLAKRLRS MHVFILDYDQ SPAGCRDALL QLTSGMVQTH VTTPGSIPTI  1260
```

```
CDLARTFARE MGEAN                                                      1275

SEQ ID NO: 49          moltype = DNA  length = 360
FEATURE                Location/Qualifiers
misc_feature           1..360
                       note = VH region of anti-GM2 antibody for VL25VH
source                 1..360
                       mol_type = other DNA
                       organism = synthetic construct
SEQUENCE: 49
gaagtccagc tggtgcagag cggcgctgag gtgaagaagc ctggcgccag cgtcaaggtg  60
agctgtaagg cctccggcta caccttcacc gactacaaca tggattgggt gaagcagagc  120
cccggacagg gcctggagtg gatgggctac atctacccca acaacggcgg caccggctac  180
aaccagaaat tcaagtccaa ggtgaccatc accgtggaca ccagcacatc caccgcctac  240
atggaactgc acagcctgag gtccgaggac acagccgtgt actactgcgc tacctacggc  300
cactactacg gctacatgtt cgcttactgg ggacagggca ccctggtgac cgtgagctcc  360

SEQ ID NO: 50          moltype = DNA  length = 318
FEATURE                Location/Qualifiers
misc_feature           1..318
                       note = VL region of anti-GM2 antibody for VL25VH
source                 1..318
                       mol_type = other DNA
                       organism = synthetic construct
SEQUENCE: 50
gatatccaac tgacccagtc cccttccagc ctgagcgctt cccccggaga cagggtgaca  60
attacctgca gcgccagctc ctccgtgagc tacatgcact ggttccagca gaagcccggc  120
aaggccccca agctgtggat ctactccaca agcaacctgg cctccggcgt gcctgccaga  180
tttagcggaa gcggcagcgg cacatcctac agcctgacca tctccaggct gcagcccgag  240
gacatcgcca catactactg ccagcagagg tccagctacc cttacacatt cggaggcggc  300
accaaggtgg agatcaag                                               318

SEQ ID NO: 51          moltype = DNA  length = 360
FEATURE                Location/Qualifiers
misc_feature           1..360
                       note = VH region of anti-GM2 antibody for VH15VL
source                 1..360
                       mol_type = other DNA
                       organism = synthetic construct
SEQUENCE: 51
gaggtgcagc tggtgcagtc cggagccgag gtgaagaagc ctggcgccag cgtgaaggtg  60
agctgtaagg cctccggcta caccttcacc gactacaaca tggactgggt caagcagagc  120
cctggccagg gcctggagtg gatgggctat atctacccca acaacggcgg caccggctac  180
aaccagaagt tcaagagcaa ggtcaccatc accgtggaca cctccacctc cacagcctac  240
atggagctgc acagcctgag gagcgaggat accgccgtgt actactgcgc tacctacggc  300
cattactacg gatacatgtt cgcctactgg ggccagggaa ccctggtcac cgtgtcctcc  360

SEQ ID NO: 52          moltype = DNA  length = 318
FEATURE                Location/Qualifiers
misc_feature           1..318
                       note = VL region of anti-GM2 antibody for VH15VL
source                 1..318
                       mol_type = other DNA
                       organism = synthetic construct
SEQUENCE: 52
gacatccagc tgacacaatc cccagcagc ctgagcgcta gccccggcga tagggtgaca  60
attacctgca gcgcctccag ctccgtgtcc tacatgcact ggtttcagca aaagcccggc  120
aaggccccta agctgtggat ctacagcacc agcaacctgg ccagcggagt gcctgccaga  180
tttagcggca gcggcagcgg caccagctac agcctgacca tcagcagact gcagcccgag  240
gatatcgcca cctactactg ccagcagagg agctcctacc cctacacatt cggcggcgga  300
accaaggtgg agatcaag                                               318

SEQ ID NO: 53          moltype = DNA  length = 360
FEATURE                Location/Qualifiers
misc_feature           1..360
                       note = VH region of anti-GM2 antibody for VH25VL
source                 1..360
                       mol_type = other DNA
                       organism = synthetic construct
SEQUENCE: 53
gaagtgcagc tggtgcagtc cggagctgag gtgaagaagc ccggcgccag cgtgaaggtc  60
agctgcaaag ccagcggcta taccttcacc gactacaaca tggactgggt gaagcagagc  120
cccggccaag gcctcgagtg gatgggatac atctacccca acaacggcgg caccggctac  180
aaccagaagt tcaagagcaa ggtgaccatc accgtggaca catccacaag caccgcctat  240
atggagctcc acagcctgag gagcgaggac accgccgtgt actactgcgc cacctacggc  300
cactactacg gctatatgtt cgcctactgg ggccagggca ccctggtgac agtgtcctcc  360

SEQ ID NO: 54          moltype = DNA  length = 318
FEATURE                Location/Qualifiers
```

```
misc_feature           1..318
                       note = VL region of anti-GM2 antibody for VH25VL
source                 1..318
                       mol_type = other DNA
                       organism = synthetic construct
SEQUENCE: 54
gatatccagc tgacacagag ccctagctcc ctgagcgcta gccctggcga cagagtgacc  60
atcacctgca gcgccagctc cagcgtgagc tacatgcact ggttccagca gaaacccggc  120
aaggcccccca agctgtggat ctacagcacc agcaatctgg ctagcggcgt gcctgccagg  180
tttagcggat ccggcagcgg cacctcctac tccctgacaa tctccagact gcagcccgag  240
gacatcgcca cctactactg ccaacagagg tcctcctacc cctacacctt cggcggcggc  300
accaaagtgg agatcaag                                                 318

SEQ ID NO: 55          moltype = DNA  length = 45
FEATURE                Location/Qualifiers
misc_feature           1..45
                       note = linker 15 for VH15VL
source                 1..45
                       mol_type = other DNA
                       organism = synthetic construct
SEQUENCE: 55
ggaggaggag gaagcggagg cggcggctcc ggcggaggcg gatcc                  45

SEQ ID NO: 56          moltype = DNA  length = 75
FEATURE                Location/Qualifiers
misc_feature           1..75
                       note = linker 25 for VH25VL
source                 1..75
                       mol_type = other DNA
                       organism = synthetic construct
SEQUENCE: 56
tccagcgccg atgatgccaa gaaggatgcc gccaaaaagg acgacgctaa gaaggatgac  60
gccaagaagg acggc                                                    75

SEQ ID NO: 57          moltype = AA  length = 19
FEATURE                Location/Qualifiers
REGION                 1..19
                       note = signal peptide
source                 1..19
                       mol_type = protein
                       organism = synthetic construct
SEQUENCE: 57
MDWTWRILFL VAAATGAHS                                                19

SEQ ID NO: 58          moltype = DNA  length = 531
FEATURE                Location/Qualifiers
source                 1..531
                       mol_type = genomic DNA
                       organism = Homo sapiens
SEQUENCE: 58
atgttccatg tttcttttag gtatatcttt ggacttcctc ccctgatcct tgttctgttg  60
ccagtagcat catctgattg tgatattgaa ggtaaagatg gcaaacaata tgagagtgtt  120
ctaatggtca gcatcgatca attattggac agcatgaaag aaattggtag caattgcctg  180
aataatgaat ttaacttttt taaaagacat atctgtgatg ctaataagga aggtatgttt  240
ttattccgtg ctgctcgcaa gttgaggcaa tttcttaaaa tgaatagcac tggtgatttt  300
gatctccact tattaaaagt ttcagaaggc acaacaatac tgttgaactg cactggccag  360
gttaaaggaa gaaaaccagc tgccctgggt gaagcccaac caacaaagag tttggaagaa  420
aataaatctt taaaggaaca gaaaaaactg aatgacttgt gtttcctaaa gagactatta  480
caagagataa aaacttgttg gaataaaatt ttgatgggca ctaaagaaca c           531

SEQ ID NO: 59          moltype = AA  length = 177
FEATURE                Location/Qualifiers
source                 1..177
                       mol_type = protein
                       organism = Homo sapiens
SEQUENCE: 59
MFHVSFRYIF GLPPLILVLL PVASSDCDIE GKDGKQYESV LMVSIDQLLD SMKEIGSNCL  60
NNEFNFFKRH ICDANKEGMF LFRAARKLRQ FLKMNSTGDF DLHLLKVSEG TTILLNCTGQ  120
VKGRKPAALG EAQPTKSLEE NKSLKEQKKL NDLCFLKRLL QEIKTCWNKI LMGTKEH      177

SEQ ID NO: 60          moltype = DNA  length = 294
FEATURE                Location/Qualifiers
source                 1..294
                       mol_type = genomic DNA
                       organism = Homo sapiens
SEQUENCE: 60
atggccctgc tactggccct cagcctgctg gttctctgga cttccccagc cccaactctg  60
agtggcacca atgatgctga agactgctgc ctgtctgtga cccagaaacc catccctggg  120
tacatcgtga ggaacttcca ctaccttctc atcaaggatg gctgcagggt gcctgctgta  180
```

-continued

```
gtgttcacca cactgagggg ccgccagctc tgtgcacccc cagaccagcc ctgggtagaa  240
cgcatcatcc agagactgca gaggacctca gccaagatga agcgccgcag cagt        294

SEQ ID NO: 61          moltype = AA  length = 98
FEATURE                Location/Qualifiers
source                 1..98
                       mol_type = protein
                       organism = Homo sapiens
SEQUENCE: 61
MALLLALSLL VLWTSPAPTL SGTNDAEDCC LSVTQKPIPG YIVRNFHYLL IKDGCRVPAV  60
VFTTLRGRQL CAPPDQPWVE RIIQRLQRTS AKMKRRSS                          98

SEQ ID NO: 62          moltype = AA  length = 25
FEATURE                Location/Qualifiers
REGION                 1..25
                       note = F2A
source                 1..25
                       mol_type = protein
                       organism = synthetic construct
SEQUENCE: 62
GSGVKQTLNF DLLKLAGDVE SNPGP                                        25

SEQ ID NO: 63          moltype = AA  length = 5
FEATURE                Location/Qualifiers
REGION                 1..5
                       note = CDR1 of VH region of anti-GM2 antibody
source                 1..5
                       mol_type = protein
                       organism = synthetic construct
SEQUENCE: 63
DYNMD                                                              5

SEQ ID NO: 64          moltype = AA  length = 17
FEATURE                Location/Qualifiers
REGION                 1..17
                       note = CDR2 of VH region of anti-GM2 antibody
source                 1..17
                       mol_type = protein
                       organism = synthetic construct
SEQUENCE: 64
YIYPNNGGTG YNQKFKS                                                 17

SEQ ID NO: 65          moltype = AA  length = 11
FEATURE                Location/Qualifiers
REGION                 1..11
                       note = CDR3 of VH region of anti-GM2 antibody
source                 1..11
                       mol_type = protein
                       organism = synthetic construct
SEQUENCE: 65
YGHYYGYMFA Y                                                       11

SEQ ID NO: 66          moltype = AA  length = 10
FEATURE                Location/Qualifiers
REGION                 1..10
                       note = CDR1 of VL region of anti-GM2 antibody
source                 1..10
                       mol_type = protein
                       organism = synthetic construct
SEQUENCE: 66
SASSSVSYMH                                                         10

SEQ ID NO: 67          moltype = AA  length = 7
FEATURE                Location/Qualifiers
REGION                 1..7
                       note = CDR2 of VL region of anti-GM2 antibody
source                 1..7
                       mol_type = protein
                       organism = synthetic construct
SEQUENCE: 67
STSNLAS                                                            7
```

-continued

```
SEQ ID NO: 68           moltype = AA  length = 9
FEATURE                 Location/Qualifiers
REGION                  1..9
                        note = CDR3 of VL region of anti-GM2 antibody
source                  1..9
                        mol_type = protein
                        organism = synthetic construct
SEQUENCE: 68
QQRSSYPYT                                                         9
```

The invention claimed is:

1. A composition comprising a therapeutically effective amount of isolated immune cells expressing a receptor, interleukin-7, and chemokine (C—C motif) ligand 19, wherein the receptor comprises a target antigen-binding region that includes a heavy-chain variable region and a light-chain variable region of an anti-ganglioside GM2 antibody, and wherein the anti-ganglioside GM2 antibody is comprising a first sequence having at least 95% sequence identity to SEQ ID NO: 2 and a second sequence having at least 95% sequence identity to SEQ ID NO: 4, and wherein the therapeutically effective amount is $1\times10^{4}$ cells or more to $1\times10^{10}$ cells or less.

2. The composition according to claim 1, wherein the first sequence has at least 96% sequence identity to SEQ ID NO: 2.

3. The composition according to claim 1, wherein the first sequence has at least 97% sequence identity to SEQ ID NO: 2.

4. The composition according to claim 1, wherein the first sequence has at least 98% sequence identity to SEQ ID NO: 2.

5. The composition according to claim 1, wherein the first sequence has at least 99% sequence identity to SEQ ID NO: 2.

6. The composition according to claim 1, wherein the first sequence comprises SEQ ID NO: 2.

7. The composition according to claim 1, wherein the second sequence has at least 96% sequence identity to SEQ ID NO: 4.

8. The composition according to claim 1, wherein the second sequence has at least 97% sequence identity to SEQ ID NO: 4.

9. The composition according to claim 1, wherein the second sequence has at least 98% sequence identity to SEQ ID NO: 4.

10. The composition according to claim 1, wherein the second sequence has at least 99% sequence identity to SEQ ID NO: 4.

11. The composition according to claim 1, wherein the second sequence comprises SEQ ID NO: 4.

12. The composition according to claim 1 wherein the anti-ganglioside GM2 antibody comprises SEQ ID NO: 2 and SEQ ID NO: 4.

13. The composition according to claim 1, wherein when mutations are present, the mutations in the heavy chain variable region and the light chain variable region are located in regions other than CDR1, CDR2, and CDR3.

14. The composition according to claim 1, wherein the heavy chain comprises amino acid sequences of SEQ ID NO: 63, SEQ ID NO: 64, and SEQ ID NO: 65, and wherein the light chain comprises amino acid sequences of SEQ ID NO: 66, SEQ ID NO: 67, and SEQ ID NO: 68.

15. The composition according to claim 1, wherein the immune cells are selected from the group consisting of T cells, natural killer cells (NK cells), B cells, monocytes, macrophages, dendritic cells, neutrophils, eosinophils, basophils, and mast cells.

16. The composition according to claim 1, wherein the receptor comprises a chimeric antigen receptor.

17. A method for producing the composition of claim 1, comprising introducing into immune cells a polynucleotide comprising a base sequence that encodes the receptor, a base sequence that encodes interleukin-7, and a base sequence that encodes chemokine (C—C motif) ligand 19, wherein the receptor comprises the target antigen-binding region that includes a heavy-chain variable region and a light-chain variable region of an anti-ganglioside GM2 antibody, and wherein the anti-ganglioside GM2 antibody is comprising a first sequence having at least 95% sequence identity to SEQ ID NO: 2 and a second sequence having at least 95% sequence identity to SEQ ID NO: 4.

18. The method according to claim 17, wherein the polynucleotide is introduced in a vector.

19. A method for treating or preventing a tumor expressing ganglioside GM2, comprising administering the composition according to claim 1 to a subject.

* * * * *